US008440391B2

(12) United States Patent
Chen et al.

(10) Patent No.: US 8,440,391 B2
(45) Date of Patent: May 14, 2013

(54) CONSTITUTIVELY ACTIVATED HUMAN G PROTEIN COUPLED RECEPTORS

(75) Inventors: Ruoping Chen, San Diego, CA (US);
Chen W. Liaw, San Diego, CA (US);
Kevin P. Lowitz, San Diego, CA (US);
Derek T. Chalmers, Riverside, CT (US);
Dominic P. Behan, San Diego, CA (US)

(73) Assignee: Arena Phamaceuticals, Inc., San Diego, CA (US)

( * ) Notice: Subject to any disclaimer, the term of this patent is extended or adjusted under 35 U.S.C. 154(b) by 2079 days.

(21) Appl. No.: 10/723,955

(22) Filed: Nov. 26, 2003

(65) Prior Publication Data

US 2004/0110238 A1 Jun. 10, 2004
US 2005/0227295 A9 Oct. 13, 2005

Related U.S. Application Data

(63) Continuation of application No. 10/417,820, filed on Apr. 16, 2003, now abandoned, which is a continuation of application No. 09/416,760, filed on Oct. 12, 1999, now abandoned.

(60) Provisional application No. 60/152,524, filed on Sep. 3, 1999, provisional application No. 60/151,114, filed on Aug. 27, 1999, provisional application No. 60/108,029, filed on Nov. 12, 1998.

(51) Int. Cl.
*C12Q 1/00* (2006.01)
*C12Q 1/68* (2006.01)
*C07K 14/435* (2006.01)

(52) U.S. Cl.
USPC .................................. 435/4; 435/6; 530/350

(58) Field of Classification Search ........................ None
See application file for complete search history.

(56) References Cited

U.S. PATENT DOCUMENTS

| | | | |
|---|---|---|---|
| 5,514,578 A | 5/1996 | Hogness et al. | 435/240.2 |
| 5,532,157 A | 7/1996 | Fink | 435/240.2 |
| 5,573,944 A | 11/1996 | Kirschner et al. | 435/252.3 |
| 5,639,616 A | 6/1997 | Liao et al. | 435/7.1 |
| 5,750,353 A | 5/1998 | Kopin et al. | 435/7.21 |
| 6,084,083 A | 7/2000 | Levinson | |
| 6,158,887 A | 12/2000 | Simpson | |
| 6,204,371 B1 | 3/2001 | Levinson | |
| 6,288,218 B1 | 9/2001 | Levinson | |
| 6,414,117 B1 | 7/2002 | Levinson | |
| 6,436,703 B1 | 8/2002 | Teng et al. | |
| 6,455,685 B1 | 9/2002 | Levinson | |
| 2002/0061567 A1 | 5/2002 | Teng et al. | |
| 2002/0106741 A1 | 8/2002 | Li et al. | |
| 2002/0146757 A1 | 10/2002 | Teng et al. | |

FOREIGN PATENT DOCUMENTS

| | | |
|---|---|---|
| WO | WO 98/32858 | 7/1998 |
| WO | WO 99/64436 A | 12/1999 |
| WO | WO02/057414 | 7/2002 |
| WO | WO02/061087 | 8/2002 |

OTHER PUBLICATIONS

Murdoch, C. et al . Blood, vol. 95, No. 10, pp. 3032-3043, 2000.*
Watson, S et al. The G-Protein Linked Receptor Facts Book, Academic Press, pp. 2-6 and 223-230, 1994.*
Kenakin, T. Pharmacological Reviews, vol. 48, No. 3, pp. 413-430 and 432-462, 1996.*
Bork, P. Nature Genetics, vol. 18, pp. 313-318, 1998.*
Karp, P. Bioinformatics, vol. 14, No. 9, pp. 753-754, 1998.*
Bork, P et al Current Opinion in Structural Biology, vol. 8, pp. 331-332, 1998.*
Vanti et al., Genomics vol. 82, pp. 531-536, 2003.*
Ta-Tung et al, Gene, vol. 278, pp. 41-45, 2001.*
Civelli et al, Pharmacology and Therapeutics, Nov. 8, pp. 1-8, 2005.*
Hancock, A.A., Biochemical Pharmacology, vol. 71, pp. 1103-1113, 2006.*
Feng et al., Kidney Research, May, vol. 67, Issue 5, pp. 1731-1738, 2005.*
Marchese et al., TIPS, vol. 20, pp. 370-375, Sep. 1999.*
Vanti et al., Biochemical and Biophysical Research Communications, vol. 35, pp. 67-71, 2003.*
Taylor et. al., Calcium signaling:IP3 rises . . . and again, Current Biology, vol. 11:R352-R353, 2001.*
Berridge et al, The versatility and universality of calcium signaling, Nature Reviews Molecular Cell Biology, vol. pp. 11-21, 2000.*
Feighner et al., "Receptor for Motilin Identified in the Human Gastrointestinal System," *Science*, vol. 284, No. 5423, Jun. 1999, pp. 2184-2188.
McKee et al., "Cloning and Characterization of Two Human G Protein-Coupled Receptor Genes (GPR38 and GPR39) Related to the Growth Hormone Secretagogue and Neurotesin Receptors," *Genomics*, vol. 46, No. 3, 1997, pp. 423-434.
Palyha et al., Ligand Activation Domain of Human Orphan Growth Hormone (GH) Secretagogue Receptor (GHS-R) Conserved From Pufferfish to Humans, *Molecular Endocrinology*, vol. 14, No. 1, 2000, pp. 160-169.
European Search Report Dated Aug. 20, 2004 for European Patent Application No. EP 99 95 0301.
Chen et al., "Identification of TDAG8 as a P2Y Purinergic Receptor," poster; Feb. 26-Mar. 3, 2000: Genome Tri Conference 2000, San Francisco, CA (1p.).
Scherr, et al "Constitutively Active G. Protein-Coupled Receptors: Potential Mechanisms of Receptor Activation," *Journal of Receptor and Signal Transduction Research* 17 (1-3): 57-73.
Kjelsberg, et al, "Constitutive activation of the alphaB-adrenergic receptor by all amino acid substitutions at a single site," *Journal of Biological Chemistry*, 287 (3): 1430-1433.
U.S. Appl. No. 09/170,496, filed Oct. 13, 1998, Liaw et al.

(Continued)

*Primary Examiner* — Ruixiang Li
(74) *Attorney, Agent, or Firm* — James S. Keddie; Bozicevic, Field & Francis, LLP

(57) ABSTRACT

The invention disclosed in this patent document relates to transmembrane receptors, more particularly to a human G protein-coupled receptor for which the endogenous ligand is unknown ("orphan GPCR receptors"), and most particularly to mutated (non-endogenous) versions of the human GPCRs for evidence of constitutive activity.

20 Claims, 9 Drawing Sheets

OTHER PUBLICATIONS

U.S. Appl. No. 09/364,425, filed Jul. 30, 1999, Behan et al.
U.S. Appl. No. 09/417,044, filed Oct. 12, 1999, Chen et al.
Kacinski et al., Apoptosis and cutaneous T cell lymphoma. Ann. NY Acad. Sci 2001;941:194-9.
Neurath et al., Regulation of T-cell apoptosis in inflammatory bowel disease: to die or not to die, that is the mucosal question. Trends Immunol. 2001;22(1):21-6.
Silvestris et al., Enhancement of T cell apoptosis correlates with increased serum levels of soluble Fas (CD95/Apo-1) in active lupus. Lupus 2003;12(1):8-14.
Zadina et al., Endorphins: Novel endogenous μ-opiate receptor agonists in regions of high μ-opiate receptor density. Ann. NY Acad. Sci. 1999;897:136-44.
Malone et al., The glucocorticoid-induced gene tdag8 encodes a pro-apoptotic G protein-coupled receptor whose activation promotes glucocorticoid-induced apoptosis. J. Biol. Chem. 2004;279(51):52850-9.
Radu et al., Normal Immune Development and Glucocorticoid-Induced Thymocyte Apoptosis in Mice Deficient for the T-Cell Death-Associated Gene 8 Receptor. Molecular and Cellular Biology. 2006; 26 (2):668-677.
Bonta et al. Prostaglandin E2 elevation of cyclic-AMP in granuloma macrophages at various stages of inflammation: relevance to anti-inflammatory and immunomodulatory functions. Prostaglandins 1981 22 95-103.
Brake et al. ATP receptors in sickness, pain and death. Chemistry and Biology 1996 3: 229-232.
Cronstein. Adenosine, an endogenous anti-inflammatory agent. J. Appl. Physiol. 1994 76: 5-13.
Deporter et al. Cyclic adenosine 3', 5'-monophosphate and the mechanism of action of three common anti-inflammatory drugs. Br. J. Pharmac. 1979 65: 163-165.
Deporter. Cyclic adenosine 3',5'-monophosphate and leucocyte chemotaxis in vivo. Br. J. Pharmac. 1977 60: 205-207.
Daval. Adenosine physiology and pharmacology: how about A2 receptors? Pharmacol. Ther. 1996 71: 325-335.
Moore et al. The role of cAMP regulation in controlling inflammation. Clin. Exp. Immunol. 1995 101:387-389.
Naik. Increased cyclic AMP-phosphodiesterase activity during inflammation and its inhibition by anti-inflammatory drugs. Eur. J. Pharmacology 1984 104: 253-259.
Missale et al., "*Dopamine receptors: from structure to function*" Physiol Rev. (1998) 78:189-225 (Review).
Sealfon et al., "*Functional domains of the gonadotropin-releasing hormone receptor*", Cell Mol Neurobiol. (1995) 15:25-42 (Review), Mar. 12, 2013.
Hebert et al., "*Structural and functional aspects of G protein-coupled receptor oligomerization*", Biochem Cell Biol. (1998) 76:1-11.
Leung et al., "Gonadotropin-releasing hormone receptor: gene structure, expression and regulation", *Biol Signals* (1996) 5:63-9.
Inglese et al., "Structure and mechanism of the G protein-coupled receptor kinases", J. Biol. Chem. (1993), 268:23735-8.
Ostrowski et al, Mutagenesis of the beta2-Adrenergic Receptor: How Structure Elucidates Function Annual Review of Pharmacology and Toxicology (1992), 32: 167-183.
Wong et al Chimeric muscarinic cholinergic: beta-adrenergic receptors that activate Gs in response to muscarinic agonists.J Biol Chem. (1990 ), 265:6219-24.
Wess et al., "Identification of a small intracellular region of the muscarinic m3 receptor as a determinant of selective coupling to PI turnover", FEBS Lett. (1989), 258:133-6.
Jackson T. Structure and function of G protein coupled receptors. Pharmacol. Ther. (1991), 50:425-42.
Yeagle et al., "*Structure of the G-protein-coupled receptor, rhodopsin: a domain approach*", Biochem Soc Trans. (1998), 26:520-31.
Filizola et al., "*BUNDLE: a program for building the transmembrane domains of G-protein-coupled receptors*", J Comput Aided Mol Des. (1998), 12:111-8.
Gouldson et al., "*Domain swapping in G-protein coupled receptor dimmers*", Protein Eng. (1998), 11:1181-93.
Eigler "Anti-inflammatory activities of cAMP-elevating agents:enhancement of IL-10 snthesis and concurrent suppression of TNF production", J. Leukocyte Biology (1998), 63: 101-107.
Moore et al., "The role of cAMP regulation in controlling inflammation", Clin. Exp. Immunol. (1995) 101: 387-389.
Benbemou et al, "Differential regulation of IFN-y, IL-10 and inducible n itric oxide synthase in human T cells by cyuclic AMP-dependent signal transduction pathyway", Immunology (1997) 91:361-368.

\* cited by examiner

TDAG8 Tissue Distribution

CONSTITUTIVELY ACTIVATED HUMAN G PROTEIN COUPLED RECEPTORS

This patent application is a continuation of U.S. Ser. No. 10/417,820, which is a continuation of U.S. Ser. No. 09/416,760, which is a continuation-in-part of U.S. Ser. No. 09/170,496, filed with the United States Patent and Trademark Office on Oct. 13, 1998. This application also claims the benefit of priority from the following provisional applications, all filed via U.S. Express Mail with the United States Patent and Trademark Office on the indicated dates: U.S. Provisional No. 60/110,060, filed Nov. 27, 1998; U.S. Provisional No. 60/120,416, filed Feb. 16, 1999; U.S. Provisional No. 60/121,852, filed Feb. 26, 1999 claiming benefit of U.S. Provisional No. 60/109,213, filed Nov. 20, 1998; U.S. Provisional No. 60/123,944, filed Mar. 12, 1999; U.S. Provisional No. 60/123,945, filed Mar. 12, 1999; U.S. Provisional No. 60/123,948, filed Mar. 12, 1999; U.S. Provisional No. 60/123,951, filed Mar. 12, 1999; U.S. Provisional No. 60/123,946, filed Mar. 12, 1999; U.S. Provisional No. 60/123,949, filed Mar. 12, 1999; U.S. Provisional No. 60/152,524, filed Sep. 3, 1999, claiming benefit of U.S. Provisional No. 60/151,114, filed Aug. 27, 1999 and U.S. Provisional No. 60/108,029, filed Nov. 12, 1998; U.S. Provisional No. 60/136,436, filed May 28, 1999; U.S. Provisional No. 60/136,439, filed May 28, 1999; U.S. Provisional No. 60/136,567, filed May 28, 1999; U.S. Provisional No. 60/137,127, filed May 28, 1999; U.S. Provisional No. 60/137,131, filed May 28, 1999; U.S. Provisional No. 60/141,448, filed Jun. 29, 1999 claiming benefit of U.S. Provisional No. 60/136,437, filed May 28, 1999; U.S. Provisional No. 60/156,633, filed Sep. 29, 1999; U.S. Provisional No. 60/156,555, filed Sep. 29, 1999; U.S. Provisional No. 60/156,634, filed Sep. 29, 1999;U.S. Provisional No. 60/156,653, filed Sep. 29, 1999; U.S. Provisional No. 60/157,280, filed Oct. 1, 1999; U.S. Provisional No. 60/157,924, filed Oct. 1, 1999; U.S. Provisional No. 60/157,281, filed Oct. 1, 1999; U.S. Provisional No. 60/157,293, filed Oct. 1, 1999; and U.S. Provisional No. 60/157,282, filed Oct. 1, 1999.

FIELD OF THE INVENTION

The invention disclosed in this patent document relates to transmembrane receptors, and more particularly to human G protein-coupled receptors, and specifically to GPCRs that have been altered to establish or enhance constitutive activity of the receptor. Preferably, the altered GPCRs are used for the direct identification of candidate compounds as receptor agonists, inverse agonists or partial agonists having potential applicability as therapeutic agents.

BACKGROUND OF THE INVENTION

Although a number of receptor classes exist in humans, by far the most abundant and therapeutically relevant is represented by the G protein-coupled receptor (GPCR or GPCRs) class. It is estimated that there are some 100,000 genes within the human genome, and of these, approximately 2%, or 2,000 genes, are estimated to code for GPCRs. Receptors, including GPCRs, for which the endogenous ligand has been identified are referred to as "known" receptors, while receptors for which the endogenous ligand has not been identified are referred to as "orphan" receptors. GPCRs represent an important area for the development of pharmaceutical products: from approximately 20 of the 100 known GPCRs, 60% of all prescription pharmaceuticals have been developed.

GPCRs share a common structural motif. All these receptors have seven sequences of between 22 to 24 hydrophobic amino acids that form seven alpha helices, each of which spans the membrane (each span is identified by number, i.e., transmembrane-1 (TM-1), transmembrane-2 (TM-2), etc.). The transmembrane helices are joined by strands of amino acids between transmembrane-2 and transmembrane-3, transmembrane-4 and transmembrane-5, and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when an endogenous ligand binds with the receptor (often referred to as "activation" of the receptor), there is a change in the conformation of the intracellular region that allows for coupling between the intracellular region and an intracellular "G-protein." It has been reported that GPCRs are "promiscuous" with respect to G proteins, i.e., that a GPCR can interact with more than one G protein. See, Kenakin, T., 43 Life Sciences 1095 (1988). Although other G proteins exist, currently, Gq, Gs, Gi, Gz and Go are G proteins that have been identified. Endogenous ligand-activated GPCR coupling with the G-protein begins a signaling cascade process (referred to as "signal transduction"). Under normal conditions, signal transduction ultimately results in cellular activation or cellular inhibition. It is thought that the IC-3 loop as well as the carboxy terminus of the receptor interact with the G protein.

Under physiological conditions, GPCRs exist in the cell membrane in equilibrium between two different conformations: an "inactive" state and an "active" state. A receptor in an inactive state is unable to link to the intracellular signaling transduction pathway to produce a biological response. Changing the receptor conformation to the active state allows linkage to the transduction pathway (via the G-protein) and produces a biological response.

A receptor may be stabilized in an active state by an endogenous ligand or a compound such as a drug. Recent discoveries, including but not exclusively limited to modifications to the amino acid sequence of the receptor, provide means other than endogenous ligands or drugs to promote and stabilize the receptor in the active state conformation. These means effectively stabilize the receptor in an active state by simulating the effect of an endogenous ligand binding to the receptor. Stabilization by such ligand-independent means is termed "constitutive receptor activation."

SUMMARY OF THE INVENTION

Disclosed herein are non-endogenous versions of endogenous, human GPCRs and uses thereof.

The present invention relates to a human T-cell death-associated gene receptor (TDAG8). The deletion of self-reactive immature T-cells in the thymus is mediated by apoptosis upon T-cell receptor interaction. Apoptosis is characterized by a rapid collapse of the nucleus, extreme chromatin condensation, DNA fragmentation, and shrinkage of cells, and it is often dependent on the synthesis of new sets of RNA and protein. (see, Choi et al., 168 Cellular Immun. 78 (1996)). There is a strong correlation between apoptosis and TDAG8; i.e., an increase in apoptosis results in an increase in the expression of TDAG8. Id. However, it is unknown whether an increase in TDAG8 expression causes T-cell mediated apoptosis, or if such expression is a result of such apoptosis.

The endogenous ligand for TDAG8 is unknown and is thus considered an orphan GPCR having an open reading frame of 1,011 bp encoding a 337 amino acid protein. (TDAG8 was cloned and sequenced in 1998. Kyaw, H. et al, 17 DNA Cell Biol. 493 (1998); see FIG. 1 of Kyaw for nucleic and deduced amino acid sequences.). Human TDAG8 is reported to be homologous to murine TDAG8. Human TDAG8 is expressed in the liver and in lymphoid tissues, including peripheral blood leukocytes, spleen, lymph nodes and thymus. TDAG8 is also reported to be localized to chromosome 14q31-32.1. Id.

BRIEF DESCRIPTION OF THE DRAWINGS

FIG. 4A shows ATP binding to "TDAG8 WT" at an EC50 value of 500 µM, while FIG. 4B shows ADP binding to "TDAG8 WT" at an EC50 value of 700 µM.

DETAILED DESCRIPTION

Figure 1:
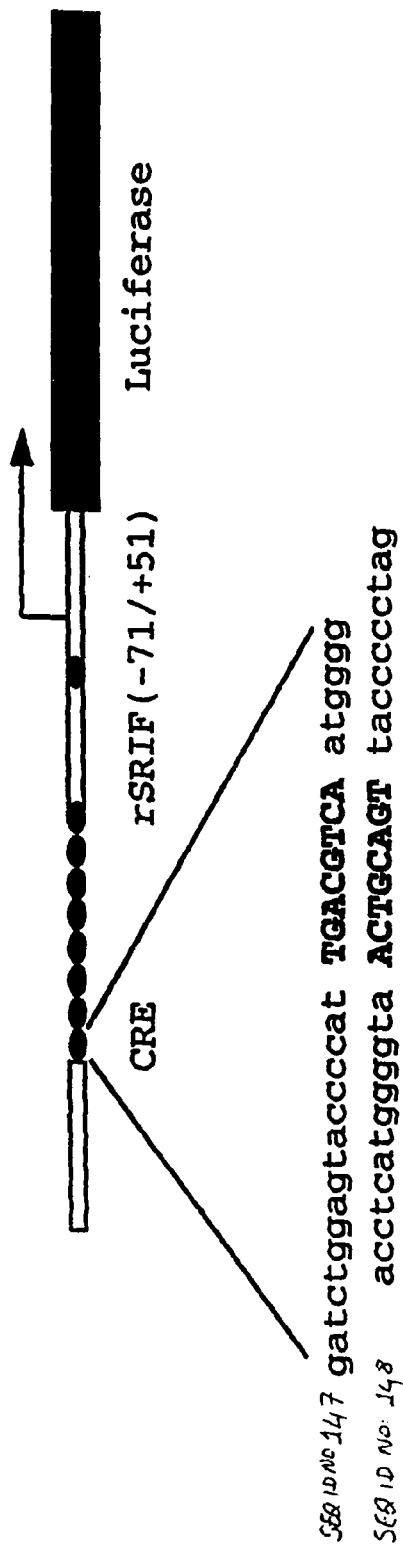
FIG. 1 is a representation of 8×CRE-Luc reporter plasmid (see, Example 4(c)3.)

The scientific literature that has evolved around receptors has adopted a number of terms to refer to ligands having various effects on receptors. For clarity and consistency, the following definitions will be used throughout this patent document. To the extent that these definitions conflict with other definitions for these terms, the following definitions shall control:

AGONISTS shall mean materials (e.g., ligands, candidate compounds) that activate the intracellular response when they bind to the receptor, or enhance GTP binding to membranes.

AMINO ACID ABBREVIATIONS used herein are set out in Table A:

TABLE A

AMINO ACID ABBREVIATIONS used herein are set out in Table A:

| ALANINE | ALA | A |
|---|---|---|
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |

TABLE A-continued

AMINO ACID ABBREVIATIONS used herein are set out in Table A:

| HISTIDINE | HIS | H |
|---|---|---|
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

PARTIAL AGONISTS shall mean materials (e.g., ligands, candidate compounds) that activate the intracellular response when they bind to the receptor to a lesser degree/extent than do agonists, or enhance GTP binding to membranes to a lesser degree/extent than do agonists.

ANTAGONIST shall mean materials (e.g., ligands, candidate compounds) that competitively bind to the receptor at the same site as the agonists but which do not activate the intracellular response initiated by the active form of the receptor, and can thereby inhibit the intracellular responses by agonists or partial agonists. ANTAGONISTS do not diminish the baseline intracellular response in the absence of an agonist or partial agonist.

CANDIDATE COMPOUND shall mean a molecule (for example, and not limitation, a chemical compound) that is amenable to a screening technique. Preferably, the phrase "candidate compound" does not include compounds which were publicly known to be compounds selected from the group consisting of inverse agonist, agonist or antagonist to a receptor, as previously determined by an indirect identification process ("indirectly identified compound"); more preferably, not including an indirectly identified compound which has previously been determined to have therapeutic efficacy in at least one mammal; and, most preferably, not including an indirectly identified compound which has previously been determined to have therapeutic utility in humans.

COMPOSITION means a material comprising at least one component; a "pharmaceutical composition" is an example of a composition.

COMPOUND EFFICACY shall mean a measurement of the ability of a compound to inhibit or stimulate receptor functionality, as opposed to receptor binding affinity. Exemplary means of detecting compound efficacy are disclosed in the Example section of this patent document.

CODON shall mean a grouping of three nucleotides (or equivalents to nucleotides) which generally comprise a nucleoside (adenosine (A), guanosine (G), cytidine (C), uridine (U) and thymidine (T)) coupled to a phosphate group and which, when translated, encodes an amino acid.

CONSTITUTIVELY ACTIVATED RECEPTOR shall mean a receptor subject to constitutive receptor activation. A constitutively activated receptor can be endogenous or non-endogenous.

CONSTITUTIVE RECEPTOR ACTIVATION shall mean stabilization of a receptor in the active state by means other than binding of the receptor with its endogenous ligand or a chemical equivalent thereof.

CONTACT or CONTACTING shall mean bringing at least two moieties together, whether in an in vitro system or an in vivo system.

DIRECTLY IDENTIFYING or DIRECTLY IDENTIFIED, in relationship to the phrase "candidate compound", shall mean the screening of a candidate compound against a constitutively activated receptor, preferably a constitutively activated orphan receptor, and most preferably against a constitutively activated G protein-coupled cell surface orphan receptor, and assessing the compound efficacy of such compound. This phrase is, under no circumstances, to be interpreted or understood to be encompassed by or to encompass the phrase "indirectly identifying" or "indirectly identified."

ENDOGENOUS shall mean a material that a mammal naturally produces. ENDOGENOUS in reference to, for example and not limitation, the term "receptor," shall mean that which is naturally produced by a mammal (for example, and not limitation, a human) or a virus. By contrast, the term NON-ENDOGENOUS in this context shall mean that which is not naturally produced by a mammal (for example, and not limitation, a human) or a virus. For example, and not limitation, a receptor which is not constitutively active in its endogenous form, but when manipulated becomes constitutively active, is most preferably referred to herein as a "non-endogenous, constitutively activated receptor." Both terms can be utilized to describe both "in vivo" and "in vitro" systems. For example, and not limitation, in a screening approach, the endogenous or non-endogenous receptor may be in reference to an in vitro screening system. As a further example and not limitation, where the genome of a mammal has been manipulated to include a non-endogenous constitutively activated receptor, screening of a candidate compound by means of an in vivo system is viable.

G PROTEIN COUPLED RECEPTOR FUSION PROTEIN and GPCR FUSION PROTEIN, in the context of the invention disclosed herein, each mean a non-endogenous protein comprising an endogenous, constitutively activate GPCR or a non-endogenous, constitutively activated GPCR fused to at least one G protein, most preferably the alpha ($\alpha$) subunit of such G protein (this being the subunit that binds GTP), with the G protein preferably being of the same type as the G protein that naturally couples with endogenous orphan GPCR. For example, and not limitation, in an endogenous state, if the G protein "Gs$\alpha$" is the predominate G protein that couples with the GPCR, a GPCR Fusion Protein based upon the specific GPCR would be a non-endogenous protein comprising the GPCR fused to Gs$\alpha$; in some circumstances, as will be set forth below, a non-predominant G protein can be fused to the GPCR. The G protein can be fused directly to the c-terminus of the constitutively active GPCR or there may be spacers between the two.

For example, and not limitation, in an endogenous state, the G protein "Gs$\alpha$" is the predominate G protein that couples with TDAG8 such that a GPCR Fusion Protein based upon TDAG8 would be a non-endogenous protein comprising TDAG8 fused to Gs$\alpha$. The G protein can be fused directly to the C-terminus of the endogenous, constitutively active orphan GPCR or there may be spacers between the two.

HOST CELL shall mean a cell capable of having a Plasmid and/or Vector incorporated therein. In the case of a prokaryotic Host Cell, a Plasmid is typically replicated as a autonomous molecule as the Host Cell replicates (generally, the Plasmid is thereafter isolated for introduction into a eukaryotic Host Cell); in the case of a eukaryotic Host Cell, a Plasmid is integrated into the cellular DNA of the Host Cell such that when the eukaryotic Host Cell replicates, the Plasmid replicates. Preferably, for the purposes of the invention disclosed herein, the Host Cell is eukaryotic, more preferably, mammalian, and most preferably selected from the group consisting of 293, 293T and COS-7 cells.

INDIRECTLY IDENTIFYING or INDIRECTLY IDENTIFIED means the traditional approach to the drug discovery process involving identification of an endogenous ligand specific for an endogenous receptor, screening of candidate compounds against the receptor for determination of those which interfere and/or compete with the ligand-receptor interaction, and assessing the efficacy of the compound for affecting at least one second messenger pathway associated with the activated receptor.

INHIBIT or INHIBITING, in relationship to the term "response" shall mean that a response is decreased or prevented in the presence of a compound as opposed to in the absence of the compound.

INVERSE AGONISTS shall mean materials (e.g., ligand, candidate compound) which bind to either the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

KNOWN RECEPTOR shall mean an endogenous receptor for which the endogenous ligand specific for that receptor has been identified.

LIGAND shall mean an endogenous, naturally occurring molecule specific for an endogenous, naturally occurring receptor.

MUTANT or MUTATION in reference to an endogenous receptor's nucleic acid and/or amino acid sequence shall mean a specified change or changes to such endogenous sequences such that a mutated form of an endogenous, non-constitutively activated receptor evidences constitutive activation of the receptor. In terms of equivalents to specific sequences, a subsequent mutated form of a human receptor is considered to be equivalent to a first mutation of the human receptor if (a) the level of constitutive activation of the subsequent mutated form of a human receptor is substantially the same as that evidenced by the first mutation of the receptor; and (b) the percent sequence (amino acid and/or nucleic acid) homology between the subsequent mutated form of the receptor and the first mutation of the receptor is at least about 80%, more preferably at least about 90% and most preferably at least 95%. Ideally, and owing to the fact that the most preferred cassettes disclosed herein for achieving constitutive activation includes a single amino acid and/or codon change between the endogenous and the non-endogenous forms of the GPCR, the percent sequence homology should be at least 98%.

NON-ORPHAN RECEPTOR shall mean an endogenous naturally occurring molecule specific for an endogenous naturally occurring ligand wherein the binding of a ligand to a receptor activates an intracellular signaling pathway.

ORPHAN RECEPTOR shall mean an endogenous receptor for which the endogenous ligand specific for that receptor has not been identified or is not known.

PHARMACEUTICAL COMPOSITION shall mean a composition comprising at least one active ingredient, whereby the composition is amenable to investigation for a specified, efficacious outcome in a mammal (for example, and not limitation, a human). Those of ordinary skill in the art will understand and appreciate the techniques appropriate for determining whether an active ingredient has a desired efficacious outcome based upon the needs of the artisan.

PLASMID shall mean the combination of a Vector and cDNA. Generally, a Plasmid is introduced into a Host Cell for the purposes of replication and/or expression of the cDNA as a protein.

STIMULATE or STIMULATING, in relationship to the term "response" shall mean that a response is increased in the presence of a compound as opposed to in the absence of the compound.

VECTOR in reference to cDNA shall mean a circular DNA capable of incorporating at least one cDNA and capable of incorporation into a Host Cell.

The order of the following sections is set forth for presentational efficiency and is not intended, nor should be construed, as a limitation on the disclosure or the claims to follow.

A. Introduction

The traditional study of receptors has always proceeded from the a priori assumption (historically based) that the endogenous ligand must first be identified before discovery could proceed to find antagonists and other molecules that could affect the receptor. Even in cases where an antagonist might have been known first, the search immediately extended to looking for the endogenous ligand. This mode of thinking has persisted in receptor research even after the discovery of constitutively activated receptors. What has not been heretofore recognized is that it is the active state of the receptor that is most useful for discovering agonists, partial agonists, and inverse agonists of the receptor. For those diseases which result from an overly active receptor or an underactive receptor, what is desired in a therapeutic drug is a compound, which acts to diminish the active state of a receptor or enhance the activity of the receptor, respectively, not necessarily a drug which is an antagonist to the endogenous ligand. This is because a compound that reduces or enhances the activity of the active receptor state need not bind at the same site as the endogenous ligand. Thus, as taught by a method of this invention, any search for therapeutic compounds should start by screening compounds against the ligand-independent active state.

This application is also related to U.S. Ser. No. 09/417,044, filed on Oct. 12, 1999 and U.S. Ser. No. 09/364,425, filed on Jul. 30, 1999, both incorporated herein by reference.

B. Identification of Human GPCRs

The efforts of the Human Genome project has led to the identification of a plethora of information regarding nucleic acid sequences located within the human genome; it has been the case in this endeavor that genetic sequence information has been made available without an understanding or recognition as to whether or not any particular genomic sequence does or may contain open-reading frame information that translate human proteins. Several methods of identifying nucleic acid sequences within the human genome are within the purview of those having ordinary skill in the art. For example, and not limitation, a variety of human GPCRs, disclosed herein, were discovered by reviewing the GenBank™ database, while other GPCRs were discovered by utilizing a nucleic acid sequence of a GPCR, previously sequenced, to conduct a BLAST™ search of the EST database. Table B, below, lists several endogenous GPCRs that we have discovered, along with a GPCR's respective homologous receptor.

TABLE B

| Disclosed Human Orphan GPCRs | Accession Number Identified | Open Reading Frame (Base Pairs) | Per Cent Homology To Designated GPCR | Reference To Homologous GPCR (Accession No.) |
|---|---|---|---|---|
| hARE-3 | AL033379 | 1,260 bp | 52.3% LPA-R | U92642 |
| hARE-4 | AC006087 | 1,119 bp | 36% P2Y5 | AF000546 |
| hARE-5 | AC006255 | 1,104 bp | 32% Oryzias latipes | D43633 |
| hGPR27 | AA775870 | 1,128 bp | | |
| hARE-1 | AI090920 | 999 bp | 43% KIAA0001 | D13626 |
| hARE-2 | AA359504 | 1,122 bp | 53% GPR27 | |
| hPPR1 | H67224 | 1,053 bp | 39% EBII | L31581 |
| hG2A | AA754702 | 1,113 bp | 31% GPR4 | L36148 |
| hRUP3 | AL035423 | 1,005 bp | 30% Drosophila melanogaster | 2133653 |
| hRUP4 | AI307658 | 1,296 bp | 32% pNPGPR 28% and 29% Zebra fish Ya and Yb, respectively | NP_004876 AAC41276 and AAB94616 |
| hRUP5 | AC005849 | 1,413 bp | 25% DEZ 23% FMLPR | Q99788 P21462 |
| hRUP6 | AC005871 | 1,245 bp | 48% GPR66 | NP_006047 |
| hRUP7 | AC007922 | 1,173 bp | 43% H3R | AF140538 |
| hCHN3 | EST 36581 | 1,113 bp | 53% GPR27 | |
| hCHN4 | AA804531 | 1,077 bp | 32% thrombin | 4503637 |
| hCHN6 | EST 2134670 | 1,503 bp | 36% edg-1 | NP_001391 |
| hCHN8 | EST 764455 | 1,029 bp | 47% KIAA0001 | D13626 |
| hCHN9 | EST 1541536 | 1,077 bp | 41% LTB4R | NM_000752 |
| hCHN10 | EST 1365839 | 1,055 bp | 35% P2Y | NM_002563 |

Receptor homology is useful in terms of gaining an appreciation of a role of the receptors within the human body. As the patent document progresses, we will disclose techniques for mutating these receptors to establish non-endogenous, constitutively activated versions of these receptors.

The techniques disclosed herein have also been applied to other human, orphan GPCRs known to the art, as will be apparent as the patent document progresses.

C. Receptor Screening

Screening candidate compounds against a non-endogenous, constitutively activated version of the human GPCRs disclosed herein allows for the direct identification of candidate compounds which act at this cell surface receptor, without requiring use of the receptor's endogenous ligand. By determining areas within the body where the endogenous version of human GPCRs disclosed herein is expressed and/or over-expressed, it is possible to determine related disease/disorder states which are associated with the expression and/or over-expression of the receptor; such an approach is disclosed in this patent document.

For example, screening candidate compounds against the endogenous, constitutively activated orphan receptor TDAG8, most preferably non-endogenous, constitutively activated orphan TDAG8, allows for the direct identification of candidate compounds which act at these orphan cell surface receptors, without requiring any prior knowledge or use of the receptor's endogenous ligand. By determining areas within the body where such receptors are expressed and/or over-expressed, it is possible to determine related disease/disorder states which are associated with the expression and/or over-expression of these receptors; such an approach is disclosed in this patent document.

With respect to creation of a mutation that may evidence constitutive activation of the human GPCR disclosed herein is based upon the distance from the proline residue at which is presumed to be located within TM6 of the GPCR; this algorithmic technique is disclosed in co-pending and commonly assigned patent document U.S. Ser. No. 09/170,496, incorporated herein by reference. The algorithmic technique is not predicated upon traditional sequence "alignment" but rather a specified distance from the aforementioned TM6 proline residue. By mutating the amino acid residue located 16 amino acid residues from this residue (presumably located in the IC3 region of the receptor) to, most preferably, a lysine residue, such activation may be obtained. Other amino acid residues may be useful in the mutation at this position to achieve this objective.

D. Disease/Disorder Identification and/or Selection

As will be set forth in greater detail below, most preferably inverse agonists to the non-endogenous, constitutively activated GPCR can be identified by the methodologies of this invention. Such inverse agonists are ideal candidates as lead compounds in drug discovery programs for treating diseases related to this receptor. Because of the ability to directly identify inverse agonists to the GPCR, thereby allowing for the development of pharmaceutical compositions, a search for diseases and disorders associated with the GPCR is relevant. For example, scanning both diseased and normal tissue samples for the presence of the GPCR now becomes more than an academic exercise or one which might be pursued along the path of identifying an endogenous ligand to the specific GPCR. Tissue scans can be conducted across a broad range of healthy and diseased tissues. Such tissue scans provide a preferred first step in associating a specific receptor with a disease and/or disorder. See, for example, co-pending application (docket number ARE-0050) for exemplary dot-blot and RT-PCR results of several of the GPCRs disclosed herein.

Preferably, the DNA sequence of the human GPCR is used to make a probe for (a) dot-blot analysis against tissue-mRNA, and/or (b) RT-PCR identification of the expression of the receptor in tissue samples. The presence of a receptor in a tissue source, or a diseased tissue, or the presence of the receptor at elevated concentrations in diseased tissue compared to a normal tissue, can be preferably utilized to identify a correlation with a treatment regimen, including but not limited to, a disease associated with that disease. Receptors can equally well be localized to regions of organs by this technique. Based on the known functions of the specific tissues to which the receptor is localized, the putative functional role of the receptor can be deduced.

More preferably, the DNA sequence of the TDAG8 receptor is used to make a probe for (a) dot-blot analysis against tissue-mRNA, and/or (b) RT-PCR identification of the expression of the receptor in tissue samples. The presence of a receptor in a tissue source, or a diseased tissue, or the presence of the receptor at elevated concentrations in diseased tissue compared to a normal tissue, can be preferably utilized to identify a correlation with a treatment regimen, including but not limited to, a disease associated with that disease. For example, TDAG8 is predominantly expressed in the lymphoid tissues, specifically the spleen, peripheral blood leukocytes and lymph nodes. Expression of TDAG8 has been reported to increase during activation of-induced death of T-cell hybridomas stimulated by glucocorticoids or anti-T-cell receptor antibodies (see, Choi J. W. et al. 168 Cell. Immunol. 78 (1996)). This report suggests that TDAG8 may play a role in immature thymocyte deletion and peripheral T-cell development. Thus, an inverse agonist to TDAG8 is intended to prevent the death of T-cells upon activation, which is an important role in the human immune system. Receptors can equally well be localized to regions of organs by this technique. Based on the known functions of the specific tissues to which the receptor is localized, the putative functional role of the receptor can be deduced.

E. Screening of Candidate Compounds

1. Generic GPCR Screening Assay Techniques

When a G protein receptor becomes constitutively active, it binds to a G protein (e.g., Gq, Gs, Gi, Gz, Go) and stimulates the binding of GTP to the G protein. The G protein then acts as a GTPase and slowly hydrolyzes the GTP to GDP, whereby the receptor, under normal conditions, becomes deactivated. However, constitutively activated receptors continue to exchange GDP to GTP. A non-hydrolyzable analog of GTP, [$^{35}$S]GTPγS, can be used to monitor enhanced binding to membranes which express constitutively activated receptors. It is reported that [$^{35}$S]GTPγS can be used to monitor G protein coupling to membranes in the absence and presence of ligand. An example of this monitoring, among other examples well-known and available to those in the art, was reported by Traynor and Nahorski in 1995. The preferred use of this assay system is for initial screening of candidate compounds because the system is generically applicable to all G protein-coupled receptors regardless of the particular G protein that interacts with the intracellular domain of the receptor.

2. Specific GPCR Screening Assay Techniques

Once candidate compounds are identified using the "generic" G protein-coupled receptor assay (i.e., an assay to select compounds that are agonists, partial agonists, or inverse agonists), further screening to confirm that the compounds have interacted at the receptor site is preferred. For example, a compound identified by the "generic" assay may not bind to the receptor, but may instead merely "uncouple" the G protein from the intracellular domain.

Gs, Gz and Gi

Gs stimulates the enzyme adenylyl cyclase. Gi (and Gz and Go), on the other hand, inhibit this enzyme. Adenylyl cyclase catalyzes the conversion of ATP to cAMP; thus, constitutively activated GPCRs that couple the Gs protein are associated with increased cellular levels of cAMP. On the other hand, constitutively activated GPCRs that couple Gi (or Gz, Go) protein are associated with decreased cellular levels of cAMP. See, generally, "Indirect Mechanisms of Synaptic Transmission," Chpt. 8, *From Neuron To Brain* ($3^{rd}$ Ed.) Nichols, J. G. et al eds. Sinauer Associates, Inc. (1992). Thus, assays that detect cAMP can be utilized to determine if a candidate compound is, e.g., an inverse agonist to the receptor (i.e., such a compound would decrease the levels of cAMP). A variety of approaches known in the art for measuring cAMP can be utilized; a most preferred approach relies upon the use of anti-cAMP antibodies in an ELISA-based format. Another type of assay that can be utilized is a whole cell second messenger reporter system assay. Promoters on genes drive the expression of the proteins that a particular gene encodes. Cyclic AMP drives gene expression by promoting the binding of a cAMP-responsive DNA binding protein or transcription factor (CREB) that then binds to the promoter at specific sites called cAMP response elements and drives the expression of the gene. Reporter systems can be constructed which have a promoter containing multiple cAMP response elements before the reporter gene, e.g., β-galactosidase or luciferase. Thus, a constitutively activated Gs-linked receptor causes the accumulation of cAMP that then activates the gene and expression of the reporter protein. The reporter protein such as β-galactosidase or luciferase can then be detected using standard biochemical assays (Chen et al. 1995).

b. Go and Gq

Gq and Go are associated with activation of the enzyme phospholipase C, which in turn hydrolyzes the phospholipid $PIP_2$, releasing two intracellular messengers: diacycloglycerol (DAG) and inistol 1,4,5-triphoisphate ($IP_3$). Increased accumulation of $IP_3$ is associated with activation of Gq- and Go-associated receptors. See, generally, "Indirect Mechanisms of Synaptic Transmission," Chpt. 8, *From Neuron To Brain* ($3^{rd}$ Ed.) Nichols, J. G. et al eds. Sinauer Associates, Inc. (1992). Assays that detect $IP_3$ accumulation can be utilized to determine if a candidate compound is, e.g., an inverse agonist to a Gq- or Go-associated receptor (i.e., such a compound would decrease the levels of $IP_3$). Gq-associated receptors can also been examined using an AP1 reporter assay in that Gq-dependent phospholipase C causes activation of genes containing AP1 elements; thus, activated Gq-associated receptors will evidence an increase in the expression of such genes, whereby inverse agonists thereto will evidence a decrease in such expression, and agonists will evidence an increase in such expression. Commercially available assays for such detection are available.

3. GPCR Fusion Protein

The use of an endogenous, constitutively activate orphan GPCR or a non-endogenous, constitutively activated orphan GPCR, for use in screening of candidate compounds for the direct identification of inverse agonists, agonists and partial agonists provide an interesting screening challenge in that, by definition, the receptor is active even in the absence of an endogenous ligand bound thereto. Thus, in order to differentiate between, e.g., the non-endogenous receptor in the presence of a candidate compound and the non-endogenous receptor in the absence of that compound, with an aim of such a differentiation to allow for an understanding as to whether such compound may be an inverse agonist, agonist, partial agonist or have no affect on such a receptor, it is preferred that an approach be utilized that can enhance such differentiation. A preferred approach is the use of a GPCR Fusion Protein.

Generally, once it is determined that a non-endogenous orphan GPCR has been constitutively activated using the assay techniques set forth above (as well as others), it is possible to determine the predominant G protein that couples with the endogenous GPCR. Coupling of the G protein to the GPCR provides a signaling pathway that can be assessed. Because it is most preferred that screening take place by use of a mammalian expression system, such a system will be expected to have endogenous G protein therein. Thus, by definition, in such a system, the non-endogenous, constitutively activated orphan GPCR will continuously signal. In this regard, it is preferred that this signal be enhanced such that in the presence of, e.g., an inverse agonist to the receptor, it is more likely that it will be able to more readily differentiate, particularly in the context of screening, between the receptor when it is contacted with the inverse agonist.

The GPCR Fusion Protein is intended to enhance the efficacy of G protein coupling with the non-endogenous GPCR. The GPCR Fusion Protein is preferred for screening with a non-endogenous, constitutively activated GPCR because such an approach increases the signal that is most preferably utilized in such screening techniques. This is important in facilitating a significant "signal to noise" ratio; such a significant ratio is import preferred for the screening of candidate compounds as disclosed herein.

The construction of a construct useful for expression of a GPCR Fusion Protein is within the purview of those having ordinary skill in the art. Commercially available expression vectors and systems offer a variety of approaches that can fit the particular needs of an investigator. The criteria of importance for such a GPCR Fusion Protein construct is that the endogenous GPCR sequence and the G protein sequence both be in-frame (preferably, the sequence for the endogenous GPCR is upstream of the G protein sequence) and that the "stop" codon of the GPCR must be deleted or replaced such that upon expression of the GPCR, the G protein can also be expressed. The GPCR can be linked directly to the G protein, or there can be spacer residues between the two (preferably, no more than about 12, although this number can be readily ascertained by one of ordinary skill in the art). We have a preference (based upon convenience) of use of a spacer in that some restriction sites that are not used will, effectively, upon expression, become a spacer. Most preferably, the G protein that couples to the non-endogenous GPCR will have been identified prior to the creation of the GPCR Fusion Protein construct. Because there are only a few G proteins that have been identified, it is preferred that a construct comprising the sequence of the G protein (i.e., a universal G protein construct) be available for insertion of an endogenous GPCR sequence therein; this provides for efficiency in the context of large-scale screening of a variety of different endogenous GPCRs having different sequences.

As noted above, constitutively activated GPCRs that couple to Gi, Gz and Go are expected to inhibit the formation of cAMP making assays based upon these types of GPCRs challenging (i.e., the cAMP signal decreases upon activation thus making the direct identification of, e.g, inverse agonists (which would further decrease this signal), interesting). As will be disclosed herein, we have ascertained that for these types of receptors, it is possible to create a GPCR Fusion Protein that is not based upon the endogenous GPCR's endogenous G protein, in an effort to establish a viable cyclase-based assay. Thus, for example, a Gz coupled receptor such as H9, a GPCR Fusion Protein can be established that utilizes a Gs fusion protein—we believe that such a fusion construct, upon expression, "drives" or "forces" the non-endogenous GPCR to couple with, e.g., Gs rather than the "natural" Gz protein, such that a cyclase-based assay can be established. Thus, for Gi, Gz and Go coupled receptors, we prefer that that when a GPCR Fusion Protein is used and the assay is based upon detection of adenyl cyclase activity, that the fusion construct be established with Gs (or an equivalent G protein that stimulates the formation of the enzyme adenylyl cyclase).

F. Medicinal Chemistry

Generally, but not always, direct identification of candidate compounds is preferably conducted in conjunction with compounds generated via combinatorial chemistry techniques, whereby thousands of compounds are randomly prepared for such analysis. Generally, the results of such screening will be compounds having unique core structures; thereafter, these compounds are preferably subjected to additional chemical modification around a preferred core structure(s) to further enhance the medicinal properties thereof. Such techniques are known to those in the art and will not be addressed in detail in this patent document.

G. Pharmaceutical Compositions

Candidate compounds selected for further development can be formulated into pharmaceutical compositions using techniques well known to those in the art. Suitable pharmaceutically-acceptable carriers are available to those in the art; for example, see Remington's Pharmaceutical Sciences, $16^{th}$ Edition, 1980, Mack Publishing Co., (Oslo et al., eds.)

H. Other Utility

Although a preferred use of the non-endogenous versions the human GPCRs disclosed herein may be for the direct identification of candidate compounds as inverse agonists, agonists or partial agonists (preferably for use as pharmaceutical agents), these versions of human GPCRs can also be utilized in research settings. For example, in vitro and in vivo systems incorporating GPCRs can be utilized to further elucidate and understand the roles these receptors play in the human condition, both normal and diseased, as well as understanding the role of constitutive activation as it applies to understanding the signaling cascade. The value in non-endogenous human GPCRs is that their utility as a research tool is enhanced in that, because of their unique features, non-endogenous human GPCRs can be used to understand the role of these receptors in the human body before the endogenous ligand therefor is identified. Other uses of the disclosed receptors will become apparent to those in the art based upon, inter alia, a review of this patent document.

I. cAMP Detection Assay

TDAG8 has been discovered to contain a conserved motif commonly found in purinergic receptors (e.g., human P2Y). Purinoceptors contain conserved residues with positively charged amino acids (e.g., His and Arg) and are preferentially activated by adenosine nucleotides (e.g., ATP and ADP). Communi et al., 272 Jo. of Biol. Chem. 31969 (1997). Thus, the binding of adenosine nucleotides to purinoceptors can be coupled to the stimulation of adenylyl cyclase. Although TDAG8 is not characterized as a purinoceptor, the common motif, located before the "DRY" region of a GPCR, led us to determine whether ATP and/or ADP are potential endogenous activators of TDAG8.

In the case of TDAG8, it has been determined that this receptor couples the G protein Gs. Gs is known to activate the enzyme adenylyl cyclase, which is necessary for catalyzing the conversion of ATP to cAMP. Although no known endogenous ligand has been identified for TDAG8, such that TDAG8 is considered an orphan GPCR, FIG. 2A evidences that ATP and ADP bind to TDAG8, resulting in an increase in cAMP. From this data, both of the adenosine nucleotides act as endogenous activators to TDAG8, and as endogenous activators, they increase the level of cAMP about 130% and about 110%, respectively.

EXAMPLES

The following examples are presented for purposes of elucidation, and not limitation, of the present invention. While specific nucleic acid and amino acid sequences are disclosed herein, those of ordinary skill in the art are credited with the ability to make minor modifications to these sequences while achieving the same or substantially similar results reported below. The traditional approach to application or understanding of sequence cassettes from one sequence to another (e.g. from rat receptor to human receptor or from human receptor A to human receptor B) is generally predicated upon sequence alignment techniques whereby the sequences are aligned in an effort to determine areas of commonality. The mutational approach disclosed herein does not rely upon this approach but is instead based upon an algorithmic approach and a positional distance from a conserved proline residue located within the TM6 region of human GPCRs. Once this approach is secured, those in the art are credited with the ability to make minor modifications thereto to achieve substantially the same results (i.e., constitutive activation) disclosed herein. Such modified approaches are considered within the purview of this disclosure.

Example 1

Endogenous Human G$_{PCRS}$

1. Identification of Human GPCRs

Certain of the disclosed endogenous human GPCRs were identified based upon a review of the GenBank™ database information. While searching the database, the following cDNA clones were identified as evidenced below (Table C).

TABLE C

| Disclosed Human Orphan GPCRs | Accession Number | Complete DNA Sequence (Base Pairs) | Open Reading Frame (Base Pairs) | Nucleic Acid SEQ. ID. NO. | Amino Acid SEQ. ID. NO. |
|---|---|---|---|---|---|
| hARE-3 | AL033379 | 111,389 bp | 1,260 bp | 1 | 2 |
| hARE-4 | AC006087 | 226,925 bp | 1,119 bp | 3 | 4 |
| hARE-5 | AC006255 | 127,605 bp | 1,104 bp | 5 | 6 |
| hRUP3 | AL035423 | 140,094 bp | 1,005 bp | 7 | 8 |
| hRUP5 | AC005849 | 169,144 bp | 1,413 bp | 9 | 10 |
| hRUP6 | AC005871 | 218,807 bp | 1,245 bp | 11 | 12 |
| hRUP7 | AC007922 | 158,858 bp | 1,173 bp | 13 | 14 |

Other disclosed endogenous human GPCRs were identified by conducting a BLAST™ search of EST database (dbest) using the following EST clones as query sequences. The following EST clones identified were then used as a probe to screen a human genomic library (Table D).

TABLE D

| Disclosed Human Orphan GPCRs | Query (Sequence) | EST Clone/ Accession No. Identified | Open Reading Frame (Base Pairs) | Nucleic Acid SEQ. ID. NO. | Amino Acid SEQ. ID. NO. |
|---|---|---|---|---|---|
| hGPCR27 | Mouse GPCR27 | AA775870 | 1,125 bp | 17 | 18 |
| hARE-1 | TDAG | 1689643 AI090920 | 999 bp | 19 | 20 |
| hARE-2 | GPCR27 | 68530 AA359504 | 1,122 bp | 21 | 22 |
| hPPR1 | Bovine PPR1 | 238667 H67224 | 1,053 bp | 23 | 24 |
| hG2A | Mouse 1179426 | See Example 2(a), below | 1,113 bp | 25 | 26 |
| hCHN3 | N.A. | EST 36581 (full length) | 1,113 bp | 27 | 28 |
| hCHN4 | TDAG | 1184934 AA804531 | 1,077 bp | 29 | 30 |
| hCHN6 | N.A. | EST 2134670 (full length) | 1,503 bp | 31 | 32 |
| hCHN8 | KIAA0001 | EST 764455 | 1,029 bp | 33 | 34 |

TABLE D-continued

| Disclosed Human Orphan GPCRs | Query (Sequence) | EST Clone/ Accession No. Identified | Open Reading Frame (Base Pairs) | Nucleic Acid SEQ. ID. NO. | Amino Acid SEQ. ID. NO. |
|---|---|---|---|---|---|
| hCHN 9 | 1365839 | EST 1541536 | 1,077 bp | 35 | 36 |
| hCHN10 | Mouse EST 1365839 | Human 1365839 | 1,005 bp | 37 | 38 |
| hRUP4 | N.A. | AI307658 | 1,296 bp | 39 | 40 |

N.A. = "not applicable".

2. Full Length Cloning a. Human G2A

Mouse EST clone 1179426 was used to obtain a human genomic clone containing all but three amino acid G2A coding sequences. The 5'of this coding sequence was obtained by using 5'RACE, and the template for PCR was Clontech's Human Spleen Marathon-Ready™ cDNA. The disclosed human G2A was amplified by PCR using the G2A cDNA specific primers for the first and second round PCR as shown in SEQ.ID.NO.: 41 and SEQ.ID.NO.:42 as follows:

5'-CTGTGTACAGCAGTTCGCAGAGTG-3' (SEQ.ID.NO.:41; $1_{st}$ round PCR)

5'-GAGTGCCAGGCAGAGCAGGTAGAC-3' (SEQ.ID.NO.:42; second round PCR)

PCR was performed using Advantage GC Polymerase Kit (Clontech; manufacturing instructions will be followed), at 94° C. for 30 sec followed by 5 cycles of 94° C. for 5 sec and 72° C. for 4 min; and 30 cycles of 94° for 5 sec and 70° for 4 min. An approximate 1.3 Kb PCR fragment was purified from agarose gel, digested with Hind III and Xba I and cloned into the expression vector pRC/CMV2 (Invitrogen). The cloned-insert was sequenced using the T7 Sequenase™ kit (USB Amersham; manufacturer instructions followed) and the sequence was compared with the presented sequence. Expression of the human G2A was detected by probing an RNA dot blot (Clontech; manufacturer instructions followed) with the $P^{32}$-labeled fragment.

b. CHN9

Sequencing of the EST clone 1541536 showed CHN9 to be a partial cDNA clone having only an initiation codon; i.e., the termination codon was missing. When CHN9 was used to blast against data base (nr), the 3' sequence of CHN9 was 100% homologous to the 5' untranslated region of the leukotriene B4 receptor cDNA, which contained a termination codon in the frame with CHN9 coding sequence. To determine whether the 5' untranslated region of LTB4R cDNA was the 3' sequence of CHN9, PCR was performed using primers based upon the 5' sequence flanking the initiation codon found in CHN9 and the 3' sequence around the termination codon found in the LTB4R 5' untranslated region. The 5' primer sequence utilized was as follows:

5'-CCCGAATTCCTGCTTGCTCCCAGCTTGGCCC-3' (SEQ.ID.NO.:43; sense) and

5'-TGTGGATCCTGCTGTCAAAGGTCCCATTCCGG-3' (SEQ.ID.NO.:44; antisense).

PCR was performed using thymus cDNA as a template and rTth polymerase (Perkin Elmer) with the buffer system provided by the manufacturer, 0.25 uM of each primer, and 0.2 mM of each 4 nucleotides. The cycle condition was 30 cycles of 94° C. for 1 min, 65° C. for 1 min and 72° C. for 1 min and 10 sec. A 1.1 kb fragment consistent with the predicted size was obtained from PCR. This PCR fragment was subcloned into pCMV (see below) and sequenced (see, SEQ.ID.NO.: 35).

c. RUP4

The full length RUP4 was cloned by RT-PCR with human brain cDNA (Clontech) as templates:

5'-TCACAATGCTAGGTGTGGTC-3' (SEQ.ID.NO.:45; sense) and

5'-TGCATAGACAATGGGATTACAG-3' (SEQ.ID.NO.:46; antisense).

PCR was performed using TaqPlus Precision™ polymerase (Stratagene; manufacturing instructions followed) by the following cycles: 94° C. for 2 min; 94° C. 30 sec; 55° C. for 30 sec, 72° C. for 45 sec, and 72° C. for 10 min. Cycles 2 through 4 were repeated 30 times.

The PCR products were separated on a 1% agarose gel and a 500 bp PCR fragment was isolated and cloned into the pCRII-TOPO™ vector (Invitrogen) and sequenced using the T7 DNA Sequenase™ kit (Amsham) and the SP6/T7 primers (Stratagene). Sequence analysis revealed that the PCR fragment was indeed an alternatively spliced form of AI307658 having a continuous open reading frame with similarity to other GPCRs. The completed sequence of this PCR fragment was as follows:

5'-TCACAATGCTAGGTGTGGTCGGCTG-GTGGCAGTCATCGTAGGATCACCCATGTGGCAC GTGCAACAACTTGAGATCAAATATGACT-TCTATATGAAAAGGAACACATCTGCT-GCTTAAGAGTG GACCAGCCCTGTGCACCAGAA-GATCTACACCACCTTCATCCTTGTCATCCTCTTCC-TCCTGCCTCTT ATGGTGATGCTTATTCTGTACG-TAAAATTGGTTATGAACTTTGGATAAA-GAAAAGAGTTGGGGATG GTTCAGTGCTTCGAAC-TATTCATGGAAAAGAAATGTCCAAAATAGCCAG-GAAGAAGAAACGAGCT GTCATTATGATGGTGA-CAGTGGTGGCTCTCTTTGCTGTGT-GCTGGGCACCATTCCATGTTGTCCATA TGATGAT-TGAATACAGTAATTTTGAAAAGGAATATGATGAT-GTCACAATCAAGATGATTTTTGCTA TCGTG-CAAATTATTGGATTTTCCAACTCCATCT-GTAATCCCATTGTCTATGCA-3' (SEQ.ID.NO.:47)

Based on the above sequence, two sense oligonucleotide primer sets:

5'-CTGCTTAGAAGAGTGGACCAG-3' (SEQ.ID.NO.:48; oligo 1)

5'-CTGTGCACCAGAAGATCTACAC-3' (SEQ.ID.NO.:49; oligo 2) and two antisense oligonucleotide primer sets:

5'-CAAGGATGAAGGTGGTGTAGA-3' (SEQ.ID.NO.:50; oligo 3)

5'-GTGTAGATCTTCTGGTGCACAGG-3' (SEQ.ID.NO.: 51; oligo 4)

were used for 3'- and 5'-RACE PCR with a human brain Marathon-Ready™ cDNA (Clontech, Cat#7400-1) as template, according to manufacture's instructions. DNA fragments generated by the RACE PCR were cloned into the pCRII-TOPO™ vector (Invitrogen) and sequenced using the SP6/T7 primers (Stratagene) and some internal primers. The 3' RACE product contained a poly(A) tail and a completed open reading frame ending at a TAA stop codon. The 5' RACE product contained an incomplete 5' end; i.e., the ATG initiation codon was not present.

Based on the new 5' sequence, oligo 3 and the following primer:

5'-GCAATGCAGGTCATAGTGAGC -3' (SEQ.ID.NO.: 52; oligo 5)

were used for the second round of 5' race PCR and the PCR products were analyzed as above. A third round of 5' race PCR was carried out utilizing antisense primers:

5'-TGGAGCATGGTGACGGGAATGCAGAAG-3' (SEQ.ID.NO.:53; oligo 6)

5'-GTGATGAGCAGGTCACTGAGCGCCAAG-3' (SEQ.ID.NO.:54; oligo 7).

The sequence of the 5' RACE PCR products revealed the presence of the initiation codon ATG, and further round of 5' race PCR did not generate any more 5' sequence. The completed 5' sequence was confirmed by RT-PCR using sense primer 5'-GCAATGCAGGCGCTTAACATTAC-3' (SEQ.ID.NO.: 55; oligo 8)

and oligo 4 as primers and sequence analysis of the 650 bp PCR product generated from human brain and heart cDNA templates (Clontech, Cat#7404-1). The completed 3' sequence was confirmed by RT-PCR using oligo 2 and the following antisense primer:

5'-TTGGGTTACAATCTGAAGGGCA-3' (SEQ.ID.NO.: 56; oligo 9)

and sequence analysis of the 670 bp PCR product generated from human brain and heart cDNA templates. (Clontech, Cat#7404-1).

d. RUP5

The full length RUP5 was cloned by RT-PCR using a sense primer upstream from ATG, the initiation codon (SEQ.ID.NO.:57), and an antisense primer containing TCA as the stop codon (SEQ.ID.NO.:58), which had the following sequences:

5'-ACTCCGTGTCCAGCAGGACTCTG-3' (SEQ.ID.NO.: 57)

5'-TGCGTCTTCCTGGACCCTCACGTG-3' (SEQ.ID.NO.: 58)

and human peripheral leukocyte cDNA (Clontech) as a template. Advantage™ cDNA polymerase (Clontech) was used for the amplification in a 50 ul reaction by the following cycle with step 2 through step 4 repeated 30 times: 94° C. for 30 sec; 94° for 15 sec; 69° for 40 sec; 72° C. for 3 min; and 72° C. fro 6 min. A 1.4 kb PCR fragment was isolated and cloned with the pCRII-TOPO™ vector (Invitrogen) and completely sequenced using the T7 DNA Sequenase™ kit (Amsham). See, SEQ.ID.NO.: 9.

e. RUP6

The full length RUP6 was cloned by RT-PCR using primers:

5'-CAGGCCTTGGATTTTAATGTCAGGGATGG-3' (SEQ.ID.NO.:59)

5'-GGAGAGTCAGCTCTGAAATAATTCAGG-3' (SEQ.ID.NO.:60);

and human thymus Marathon-Ready™ cDNA (Clontech) as a template. Advantage cDNA polymerase (Clontech, according to manufacturer's instructions) was used for the amplification in a 50 ul reaction by the following cycle: 94° C. for 30 sec; 94° C. for 5 sec; 66° C. for 40 sec; 72° C. for 2.5 sec and 72° C. for 7 min. Cycles 2 through 4 were repeated 30 times. A 1.3 Kb PCR fragment was isolated and cloned into the pCRII-TOPO™ vector (Invitrogen) and completely sequenced (see, SEQ.ID.NO.: 11) using the ABI Big Dye Terminator™ kit (P.E. Biosystem).

f. RUP7

The full length RUP7 was cloned by RT-PCR using primers:

5'-TGATGTGATGCCAGATACTAATAGCAC-3'(SEQ.ID.NO.:61; sense) and

5'-CCTGATTCATTTAGGTGAGATTGAGAC-3'(SEQ.ID.NO.:62; antisense)

and human peripheral leukocyte cDNA (Clontech) as a template. Advantage™ cDNA polymerase (Clontech) was used for the amplification in a 50 ul reaction by the following cycle with step 2 to step 4 repeated 30 times: 94° C. for 2 minutes; 94° C. for 15 seconds; 60° C. for 20 seconds; 72° C. for 2 minutes; 72° C. for 10 minutes. A 1.25 Kb PCR fragment was isolated and cloned into the pCRII-TOPO™ vector (Invitrogen) and completely sequenced using the ABI Big Dye Terminator™ kit (P.E. Biosystem). See, SEQ.ID.NO.: 13.

3. Angiotensin II Type 1 Receptor ("AT1")

The endogenous human angiotensin II type 1 receptor ("AT1") was obtained by PCR using genomic DNA as template and rTth polymerase (Perkin Elmer) with the buffer system provided by the manufacturer, 0.25 μM of each primer, and 0.2 mM of each 4 nucleotides. The cycle condition was 30 cycles of 94° C. for 1 min, 55° C. for 1 min and 72 ° C. for 1.5 min. The 5' PCR primer contains a HindIII site with the sequence:

5'-CCCAAGCTTCCCCAGGTGTATTTGAT-3' (SEQ.ID.NO.: 63)

and the 3' primer contains a BamHI site with the following sequence:

5'-GTTGGATCCACATAATGCATTTTCTC-3' (SEQ.ID.NO.: 64).

The resulting 1.3 kb PCR fragment was digested with HindIII and BamHI and cloned into HindIII-BamHI site of pCMV expression vector. The cDNA clone was fully sequenced. Nucleic acid (SEQ.ID.NO.: 65) and amino acid (SEQ.ID.NO.: 66) sequences for human AT1 were thereafter determined and verified.

4. GPR38

To obtain GPR38, PCR was performed by combining two PCR fragments, using human genomic cDNA as template and rTth poymerase (Perkin Elmer) with the buffer system provided by the manufacturer, 0.25 uM of each primer, and 0.2 mM of each 4 nucleotides. The cycle condition for each PCR reaction was 30 cycles of 94° C. for 1 min 62° C. for 1 min and 72° C. for 2 min.

The first fragment was amplified with the 5' PCR primer that contained an end site with the following sequence:

5'-ACCATGGGCAGCCCCTGGAACGGCAGC-3' (SEQ.ID.NO.:67)

and a 3' primer having the following sequence:

5'-AGAACCACCACCAGCAGGACGCGGACG-GTCTGCCGGTGG-3' (SEQ.ID.NO.:68).

The second PCR fragment was amplified with a 5' primer having the following sequence:

5'-GTCCGCGTCCTGCTGGTGGTGGTTCTG-GCATTTATAATT-3' (SEQ.ID.NO.: 69)

and a 3' primer that contained a BamHI site and having the following sequence:

5'-CCTGGATCCTTATCCCATCGTCTTCACGTTAGC-3' (SEQ.ID.NO.: 70).

The two fragments were used as templates to amplify GPR38, using SEQ.ID.NO.: 67 and SEQ.ID.NO.: 70 as primers (using the above-noted cycle conditions). The resulting 1.44 kb PCR fragment was digested with BamHI and cloned into Blunt-BamHI site of pCMV expression vector.

5. MC4

To obtain MC4, PCR was performed using human genomic cDNA as template and rTth poymerase (Perkin Elmer) with the buffer system provided by the manufacturer, 0.25 uM of each primer, and 0.2 mM of each 4 nucleotides. The cycle condition for each PCR reaction was 30 cycles of 94° C. for 1 min, 54° C. for 1 min and 72° C. for 1.5 min. The 5' PCR contained an EcoRI site with the sequence:
5'-CTGGAATTCTCCTGCCAGCATGGTGA-3' (SEQ.ID.NO.: 71)
and the 3' primer contained a BamHI site with the sequence:
5'-GCAGGATCCTATATTGCGTGCTCTGTCCCC'-3 (SEQ.ID.NO.: 72).

The 1.0 kb PCR fragment was digest with EcoRI and BamHI and cloned into EcoRI-BamHI site of pCMV expression vector. Nucleic acid (SEQ.ID.NO.: 73) and amino acid (SEQ.ID.NO.: 74) sequences for human MC4 were thereafter determined.

6. CCKB

To obtain CCKB, PCR was performed using human stomach cDNA as template and rTth poymerase (Perkin Elmer) with the buffer system provided by the manufacturer, 0.25 uM of each primer, and 0.2 mM of each 4 nucleotides. The cycle condition for each PCR reaction was 30 cycles of 94° C. for 1 min, 65° C. for 1 min and 72° C. for 1 min and 30 sec. The 5' PCR contained a HindIII site with the sequence:
5'-CCGAAGCTTCGAGCTGAGTAAGGCGGCGGGCT-3' (SEQ.ID.NO.: 75)
and the 3' primer contained an EcoRI site with the sequence:
5'-GTGGAATTCATTTGCCCTGCCTCAACCCCCA-3 (SEQ.ID.NO.: 76).

The resulting 1.44 kb PCR fragment was digest with HindIII and EcoRI and cloned into HindIII-EcoRI site of pCMV expression vector. Nucleic acid (SEQ.ID.NO.: 77) and amino acid (SEQ.ID.NO.: 78) sequences for human CCKB were thereafter determined.

7. TDAG8

To obtain TDAG8, PCR was performed using genomic DNA as template and rTth polymerase (Perkin Elmer) with the buffer system provided by the manufacturer, 0.25 µM of each primer, and 0.2 mM of each 4 nucleotides. The cycle condition was 30 cycles of 94° C. for 1 min, 56° C. for 1 min and 72° C. for 1 min and 20 sec. The 5' PCR primer contained a HindIII site with the following sequence:
5'-TGCAAGCTTAAAAAGGAAAAAATGAACAGC-3' (SEQ.ID.NO.: 79)
and the 3' primer contained a BamHI site with the following sequence:
5'-TAAGGATCCCTTCCCTTCAAAACATCCTTG -3' (SEQ.ID.NO.: 80).

The resulting 1.1 kb PCR fragment was digested with HindIII and BamHI and cloned into HindIII-BamHI site of pCMV expression vector. Three resulting clones sequenced contained three potential polymorphisms involving changes of amino acid 43 from Pro to Ala, amino acid 97 from Lys to Asn and amino acid 130 from Ile to Phe. Nucleic acid (SEQ.ID.NO.: 81) and amino acid (SEQ.ID.NO.: 82) sequences for human TDAG8 were thereafter determined.

8. H9

To obtain H9, PCR was performed using pituitary cDNA as template and rTth polymerase (Perkin Elmer) with the buffer system provided by the manufacturer, 0.25 µM of each primer, and 0.2 mM of each 4 nucleotides. The cycle condition was 30 cycles of 94° C. for 1 min, 62° C. for 1 min and 72° C. for 2 min. The 5' PCR primer contained a HindIII site with the following sequence:
5'-GGAAAGCTTAACGATCCCCAGGAGCAACAT-3' (SEQ.ID.NO.:15)
and the 3' primer contained a BamHI site with the following sequence:
5'-CTGGGATCCTACGAGAGCATTTTTCACACAG-3' (SEQ.ID.NO.:16).

The resulting 1.9 kb PCR fragment was digested with HindIII and BamHI and cloned into HindIII-BamHI site of pCMV expression vector. H9 contained three potential polymorphisms involving changes of amino acid P320S, S493N and amino acid G448A. Nucleic acid (SEQ.ID.NO.: 139) and amino acid (SEQ.ID.NO.: 140) sequences for human H9 were thereafter determined.

Example 2

Preparation of Non-Endogenous, Constitutively Activated GPCRs

Those skilled in the art are credited with the ability to select techniques for mutation of a nucleic acid sequence. Presented below are approaches utilized to create non-endogenous versions of several of the human GPCRs disclosed above. The mutations disclosed below are based upon an algorithmic approach whereby the 16$^{th}$ amino acid (located in the IC3 region of the GPCR) from a conserved proline residue (located in the TM6 region of the GPCR, near the TM6/IC3 interface) is mutated, most preferably to a lysine amino acid residue.

1. Tranformer Site-Directed™ Mutagenesis

Preparation of non-endogenous human GPCRs may be accomplished on human GPCRs using Transformer Site-Directed™ Mutagenesis Kit (Clontech) according to the manufacturer instructions. Two mutagenesis primers are utilized, most preferably a lysine mutagenesis oligonucleotide that creates the lysine mutation, and a selection marker oligonucleotide. For convenience, the codon mutation to be incorporated into the human GPCR is also noted, in standard form (Table E):

TABLE E

| Receptor Identifier | Codon Mutation |
|---|---|
| hARE-3 | F313K |
| hARE-4 | V233K |
| hARE-5 | A240K |
| hGPCR14 | L257K |
| hGPCR27 | C283K |
| hARE-1 | E232K |
| hARE-2 | G285K |
| hPPR1 | L239K |
| hG2A | K232A |
| hRUP3 | L224K |
| hRUP5 | A236K |
| hRUP6 | N267K |
| hRUP7 | A302K |
| hCHN4 | V236K |
| hMC4 | A244K |
| hCHN3 | S284K |
| hCHN6 | L352K |
| hCHN8 | N235K |
| hCHN9 | G223K |
| hCHN10 | L231K |
| hH9 | F236K |

The following GPCRs were mutated according with the above method using the designated sequence primers (Table F).

TABLE F

| Receptor Identifier | Codon Mutation | Lysine Mutagenesis (SEQ. ID. NO.) 5'-3' orientation, mutation sequence underlined | Selection Marker (SEQ. ID. NO.) 5'-3' orientation |
|---|---|---|---|
| hRUP4 | V272K | CAGGAAGAAG<u>AAA</u>CGAGC TGTCATTATGATGGTGACA GTG (83) | CACTGTCACCATCATAATG ACAGCTCGTTTCTTCTTCC TG (84) |
| hAT1 | see below | alternative approach; see below | alternative approach; see below |
| hGPR38 | V297K | GGCCACCGGCAGACC<u>AAA</u>C GCGTCCTGCTG (85) | CTCCTTCGGTCCTCCTATC GTTGTCAGAAGT (86) |
| hCCKB | V332K | alternative approach; see below | alternative approach; see below |
| hTDAG8 | I225K | GGAAAAGAAGAGAATCAA <u>AAA</u>ACTACTTGTCAGCATC (87) | CTCCTTCGGTCCTCCTATC GTTGTCAGAAGT (88) |
| hH9 | F236K | GCTGAGGTTCGCAAT<u>AAA</u>C TAACCATGTTTGTG (143) | CTCCTTCGGTCCTCCTATC GTTGTCAGAAGT (144) |
| hMC4 | A244K | GCCAATATGAAGGGA<u>AAA</u> ATTACCTTGACCATC (137) | CTCCTTCGGTCCTCCTATC GTTGTCAGAAGT (138) |

The non-endogenous human GPCRs were then sequenced and the derived and verified nucleic acid and amino acid sequences are listed in the accompanying "Sequence Listing" appendix to this patent document, as summarized in Table G below:

TABLE G

| Non Endogenous Human GPCR | Nucleic Acid Sequence Listing | Amino Acid Sequence Listing |
|---|---|---|
| hRUP4 (V272K) | SEQ. ID. NO.: 127 | SEQ.ID.NO.: 128 |
| hAT1 (see alternative approaches below) | (see alternative approaches below) | (see alternative approaches, below) |
| hGPR38 (V297K) | SEQ. ID. NO.: 129 | SEQ. ID. NO.: 130 |
| hCCKB (V332K) | SEQ. ID. NO.: 131 | SEQ. ID. NO.: 132 |
| HTDAG8 (I225K) | SEQ. ID. NO.: 133 | SEQ. ID. NO.: 134 |
| hH9 (F236K) | SEQ. ID. NO.: 141 | SEQ. ID. NO.: 142 |
| hMC4 (A244K) | SEQ. ID. NO.: 135 | SEQ. ID. NO.: 136 |

2. Alternative Approaches For Creation of Non-Endogenous Human GPCRs
   a. AT1
   1. F239K Mutation Preparation of a non-endogenous, constitutively activated human AT1 receptor was accomplished by creating an F239K mutation (see, SEQ.ID.NO.: 89 for nucleic acid sequence, and SEQ.ID.NO.: 90 for amino acid sequence). Mutagenesis was performed using Transformer Site-Directed Mutagenesis™ Kit (Clontech) according to the to manufacturer's instructions. The two mutagenesis primers were used, a lysine mutagenesis oligonucleotide (SEQ.ID.NO.: 91) and a selection marker oligonucleotide (SEQ.ID.NO.: 92), which had the following sequences:
5'-CCAAGAAATGATGATATTAAAAA-
   GATAATTATGGC-3' (SEQ.ID.NO.:91)
5'-CTCCTTCGGTCCTCCTATCGTTGTCAGAAGT-3'
   (SEQ.ID.NO.:92),
respectively.
//
   2. N111A Mutation Preparation of a non-endogenous human AT1 receptor was also accomplished by creating an N111A mutation (see, SEQ.ID.NO.:93 for nucleic acid sequence, and SEQ.ID.NO.: 94 for amino acid sequence). Two PCR reactions were performed using pfu polymerase (Stratagene) with the buffer system provided by the manufacturer, supplemented with 10% DMSO, 0.25 µM of each primer, and 0.5 mM of each 4 nucleotides. The 5' PCR sense primer used had the following sequence:
5'-CCCAAGCTTCCCCAGGTGTATTTGAT-3' (SEQ.ID.NO.: 95)
and the antisense primer had the following sequence:
5'-CCTGCAGGCGAAACTGACTCTGGCTGAAG-3' (SEQ.ID.NO.: 96).

The resulting 400 bp PCR fragment was digested with HindIII site and subcloned into HindIII-SmaI site of pCMV vector (5' construct). The 3' PCR sense primer used had the following sequence:
5'-CTGTACGCTAGTGTGTTTCTACTCACGT-
   GTCTCAGCATTGAT-3' (SEQ.ID.NO.: 97)
and the antisense primer had the following sequence:
5'-GTTGGATCCACATAATGCATTTTCTC-3' (SEQ.ID.NO.: 98)

The resulting 880 bp PCR fragment was digested with BamHI and inserted into Pst (blunted by T4 polymerase) and BamHI site of 5' construct to generated the full length N111A construct. The cycle condition was 25 cycles of 94° C. for 1 min, 60° C. for 1 min and 72° C. for 1 min (5' PCR) or 1.5 min (3' PCR).

3. AT2K255IC3 Mutation

Preparation of a non-endogenous, constitutively activated human AT1 was accomplished by creating an AT2K255IC3 "domain swap" mutation (see, SEQ.ID.NO.:99 for nucleic acid sequence, and SEQ.ID.NO.: 100 for amino acid sequence). Restriction sites flanking IC3 of AT1 were generated to facilitate replacement of the IC3 with corresponding IC3 from angiotensin II type 2 receptor (AT2). This was accomplished by performing two PCR reactions. A 5' PCR fragment (Fragment A) encoded from the 5' untranslated region to the beginning of IC3 was generated by utilizing SEQ.ID.NO.: 63 as sense primer and the following sequence:
5'-TCCGAATTCCAAAATAACTTGTAAGAAT-
   GATCAGAAA-3' (SEQ.ID.NO.: 101)
as antisense primer. A 3' PCR fragment (Fragment B) encoding from the end of IC3 to the 3' untranslated region was generated by using the following sequence:
5'-AGATCTTAAGAAGATAATTATGGCAATTGTGCT-3'
   (SEQ.ID.NO.: 102)
as sense primer and SEQ.ID.NO.: 64 as antisense primer. The PCR condition was 30 cycles of 94° C. for 1 min, 55° C. for 1 min and 72° C. for 1.5 min using endogenous AT1 cDNA clone as template and pfu polymerase (Stratagene), with the buffer systems provided by the manufacturer, supplemented with 10% DMSO, 0.25 µM of each primer, and 0.5 mM of each 4 nucleotides. Fragment A (720 bp) was digested with HindIII and EcoRI and subcloned. Fragment B was digested with BamHI and subcloned into pCMV vector with an EcoRI site 5' to the cloned PCR fragment.

The DNA fragment (Fragment C) encoding IC3 of AT2 with a L255K mutation and containing an EcoRI cohesive end at 5' and a AflII cohesive end at 3', was generated by annealing 2 synthetic oligonucleotides having the following sequences:
5'-AATTCGAAAACACTTACTGAAGACGAAT-AGCTATGGGAAGAACAGGATAACCCGT-GACCAAG-3' (sense; SEQ.ID.NO.:103)
5'-TTAACTTGGTCACGGGTTATCCTGTTCT-TCCCATAGCTATTCGTCTTCAGT AAGTGTTTTCG-3' (antisense; SEQ.ID.NO.:104)

Fragment C was inserted in front of Fragment B through EcoRI and AflII site. The resulting clone was then ligated with the Fragment A through the EcoRI site to generate AT1 with AT2K255IC3.
//

4. A243+ Mutation

Preparation of a non-endogenous human AT1 receptor was also accomplished by creating an A243+ mutation (see, SEQ.ID.NO.: 105 for nucleic acid sequence, and SEQ.ID.NO.: 106 for amino acid sequence). An A243+ mutation was constructed using the following PCR based strategy: Two PCR reactions was performed using pfu polymerase (Stratagene) with the buffer system provided by the manufacturer supplemented with 10% DMSO, 0.25 µM of each primer, and 0.5 mM of each 4 nucleotides. The 5' PCR sense primer utilized had the following sequence:
5'-CCCAAGCTTCCCCAGGTGTATTTGAT-3' (SEQ.ID.NO.: 107)
and the antisense primer had the following sequence:
5'-AAGCACAATTGCTGCATAATTATCT-TAAAAATATCATC-3' (SEQ.ID.NO.: 108).

The 3' PCR sense primer utilized had the following sequence:
5'-AAGATAATTATGGCAGCAATTGT-GCTTTTCTTTTTCTTT-3' (SEQ.ID.NO.: 109)
containing the Ala insertion and antisense primer:
5'-GTTGGATCCACATAATGCATTTTCTC-3' (SEQ.ID.NO.: 110).
The cycle condition was 25 cycles of 94° C. for 1 min, 54° C. for 1 min and 72° C. for 1.5 min. An aliquot of the 5' and 3' PCR were then used as co-template to perform secondary PCR using the 5' PCR sense primer and 3' PCR antisense primer. The PCR condition was the same as primary PCR except the extention time was 2.5 min. The resulting PCR fragment was digested with HindIII and BamHI and subcloned into pCMV vector. (See, SEQ.ID.NO.: 105)

4. CCKB

Preparation of the non-endogenous, constitutively activated human CCKB receptor was accomplished by creating a V322K mutation (see, SEQ.ID.NO.: 111 for nucleic acid sequence and SEQ.ID.NO.: 112 for amino acid sequence). Mutagenesis was performed by PCR via amplification using the wildtype CCKB from Example 1.

The first PCR fragment (1 kb) was amplified by using SEQ.ID.NO.: 75 and an antisense primer comprising a V322K mutation:
5'-CAGCAGCATGCGCTTCACGCGCTTCTTAGCCCAG-3' (SEQ.ID.NO.: 113).

The second PCR fragment (0.44 kb) was amplified by using a sense primer comprising the V322K mutation:
5'-AGAAGCGCGTGAAGCGCATGCTGCTGGT-GATCGTT-3' (SEQ.ID.NO.: 114) and SEQ.ID.NO.: 76.

The two resulting PCR fragments were then used as template for amplifying CCKB comprising V332K, using SEQ.ID.NO.: 75 and SEQ.ID.NO.: 76 and the above-noted system and conditions. The resulting 1.44 kb PCR fragment containing the V332K mutation was digested with HindIII and EcoRI and cloned into HindIII-EcoRI site of pCMV expression vector. (See, SEQ.ID.NO.: 111).

3. QuikChange™ Site-Directed™ Mutagenesis

Preparation of non-endogenous human GPCRs can also be accomplished by using QuikChange™ Site-Directed™ Mutagenesis Kit (Stratagene, according to manufacturer's instructions). Endogenous GPCR is preferably used as a template and two mutagenesis primers utilized, as well as, most preferably, a lysine mutagenesis oligonucleotide and a selection marker oligonucleotide (included in kit). For convenience, the codon mutation incorporated into the human GPCR and the respective oligonucleotides are noted, in standard form (Table H):

TABLE H

| Receptor Identifier | Codon Mutation | Lysine Mutagenesis (SEQ. ID. NO.) 5'-3' orientation, mutation underlined | Selection Marker (SEQ. ID. NO.) 5'-3' orientation |
|---|---|---|---|
| hCHN3 | S284K | ATGGAGAAAAGAATCAAAAGAATGTTCTATATA (115) | TATATAGAACATTCTTTTGATTCTTTTCTCCAT (116) |
| hCHN6 | L352K | CGCTCTCTGGCCTTGAAGCGCACGCTCAGC (117) | GCTGAGCGTGCGCTTCAAGGCCAGAGAGCG (118) |
| hCHN8 | N235K | CCCAGGAAAAAGGTGAAAGTCAAAGTTTTC (119) | GAAAACTTTGACTTTCACCTTTTTCCTGGG (120) |
| hCHN9 | G223K | GGGGCGCGGGTGAAACGGCTGGTGAGC (121) | GCTCACCAGCCGTTTCACCCGCGCCCC (122) |
| hCHN10 | L231K | CCCCTTGAAAAGCCTAAGAACTTGGTCATC (123) | GATGACCAAGTTCTTAGGCTTTTCAAGGGG (124) |

Example 3

Receptor Expression

Although a variety of cells are available to the art for the expression of proteins, it is most preferred that mammalian cells be utilized. The primary reason for this is predicated upon practicalities, i.e., utilization of, e.g., yeast cells for the expression of a GPCR, while possible, introduces into the protocol a non-mammalian cell which may not (indeed, in the case of yeast, does not) include the receptor-coupling, genetic-mechanism and secretary pathways that have evolved for mammalian systems—thus, results obtained in non-mammalian cells, while of potential use, are not as preferred as that obtained from mammalian cells. Of the mammalian cells, COS-7, 293 and 293T cells are particularly preferred, although the specific mammalian cell utilized can be predicated upon the particular needs of the artisan.

On day one, $1\times10^7$ 293T cells per 150 mm plate were plated out. On day two, two reaction tubes were prepared (the proportions to follow for each tube are per plate): tube A was prepared by mixing 20 µg DNA (e.g., pCMV vector; pCMV vector with receptor cDNA, etc.) in 1.2 ml serum free DMEM (Irvine Scientific, Irvine, Calif.); tube B was prepared by mixing 120 µl lipofectamine (Gibco BRL) in 1.2 ml serum free DMEM. Tubes A and B were admixed by inversions (several times), followed by incubation at room temperature for 30-45 min. The admixture is referred to as the "transfection mixture". Plated 293T cells were washed with 1×PBS, followed by addition of 10 ml serum free DMEM. 2.4 ml of the transfection mixture were added to the cells, followed by incubation for 4 hrs at 37° C./5% $CO_2$. The transfection mixture was removed by aspiration, followed by the addition of 25 ml of DMEM/10% Fetal Bovine Serum. Cells were incubated at 37° C./5% $CO_2$. After 72 hr incubation, cells were harvested and utilized for analysis.

Example 4

Assays for Determination of Constitutive Activity of Non-Endogenous GPCRs

A variety of approaches are available for assessment of constitutive activity of the non-endogenous human GPCRs. The following are illustrative; those of ordinary skill in the art are credited with the ability to determine those techniques that are preferentially beneficial for the needs of the artisan.

1. Membrane Binding Assays: [$^{35}$S]GTPγS Assay

When a G protein-coupled receptor is in its active state, either as a result of ligand binding or constitutive activation, the receptor couples to a G protein and stimulates the release of GDP and subsequent binding of GTP to the G protein. The alpha subunit of the G protein-receptor complex acts as a GTPase and slowly hydrolyzes the GTP to GDP, at which point the receptor normally is deactivated. Constitutively activated receptors continue to exchange GDP for GTP. The non-hydrolyzable GTP analog, [$^{35}$S]GTPγS, can be utilized to demonstrate enhanced binding of [$^{35}$S]GTPγS to membranes expressing constitutively activated receptors. The advantage of using [$^{35}$S]GTPγS binding to measure constitutive activation is that: (a) it is generically applicable to all G protein-coupled receptors; (b) it is proximal at the membrane surface making it less likely to pick-up molecules which affect the intracellular cascade.

The assay utilizes the ability of G protein coupled receptors to stimulate [$^{35}$S]GTPγS binding to membranes expressing the relevant receptors. The assay can, therefore, be used in the direct identification method to screen candidate compounds to known, orphan and constitutively activated G protein-coupled receptors. The assay is generic and has application to drug discovery at all G protein-coupled receptors.

The [$^{35}$S]GTPγS assay can be incubated in 20 mM HEPES and between 1 and about 20 mM $MgCl_2$ (this amount can be adjusted for optimization of results, although 20 mM is preferred) pH 7.4, binding buffer with between about 0.3 and about 1.2 nM [$^{35}$S]GTPγS (this amount can be adjusted for optimization of results, although 1.2 is preferred ) and 12.5 to 75 µg membrane protein (e.g, COS-7 cells expressing the receptor; this amount can be adjusted for optimization, although 75 µg is preferred) and 1 µM GDP (this amount can be changed for optimization) for 1 hour. Wheatgerm agglutinin beads (25 µl; Amersham) should then be added and the mixture incubated for another 30 minutes at room temperature. The tubes are then centrifuged at 1500×g for 5 minutes at room temperature and then counted in a scintillation counter.

A less costly but equally applicable alternative has been identified which also meets the needs of large scale screening. Flash plates™ and Wallac™ scintistrips may be utilized to format a high throughput [$^{35}$S]GTPγS binding assay. Furthermore, using this technique, the assay can be utilized for known GPCRs to simultaneously monitor tritiated ligand binding to the receptor at the same time as monitoring the efficacy via [$^{35}$S]GTPγS binding. This is possible because the Wallac beta counter can switch energy windows to look at both tritium and $^{35}$S-labeled probes. This assay may also be used to detect other types of membrane activation events resulting in receptor activation. For example, the assay may be used to monitor $^{32}$P phosphorylation of a variety of receptors (both G protein coupled and tyrosine kinase receptors). When the membranes are centrifuged to the bottom of the well, the bound [$^{35}$S]GTPγS or the $^{32}$P-phosphorylated receptor will activate the scintillant which is coated of the wells. Scinti® strips (Wallac) have been used to demonstrate this principle. In addition, the assay also has utility for measuring ligand binding to receptors using radioactively labeled ligands. In a similar manner, when the radiolabeled bound ligand is centrifuged to the bottom of the well, the scintistrip label comes into proximity with the radiolabeled ligand resulting in activation and detection.

2. Adenylyl Cyclase

A Flash Plate™ Adenylyl Cyclase kit (New England Nuclear; Cat. No. SMP004A) designed for cell-based assays can be modified for use with crude plasma membranes. The Flash Plate wells contain a scintillant coating which also contains a specific antibody recognizing cAMP. The cAMP generated in the wells was quantitated by a direct competition for binding of radioactive cAMP tracer to the cAMP antibody. The following serves as a brief protocol for the measurement of changes in cAMP levels in membranes that express the receptors.

Transfected cells are harvested approximately three days after transfection. Membranes were prepared by homogenization of suspended cells in buffer containing 20 mM HEPES, pH 7.4 and 10 mM $MgCl_2$. Homogenization is performed on ice using a Brinkman Polytron™ for approximately 10 seconds. The resulting homogenate is centrifuged at 49,000×g for 15 minutes at 4° C. The resulting pellet is then resuspended in buffer containing 20 mM HEPES, pH 7.4 and 0.1 mM EDTA, homogenized for 10 seconds, followed by centrifugation at 49,000×g for 15 minutes at 4° C. The resulting pellet can be stored at −80° C. until utilized. On the day of measurement, the membrane pellet is slowly thawed at room temperature, resuspended in buffer containing 20 mM HEPES, pH 7.4 and 10 mM $MgCL_2$ (these amounts can be optimized, although the values listed herein are preferred), to yield a final protein concentration of 0.60 mg/ml (the resuspended membranes were placed on ice until use).

cAMP standards and Detection Buffer (comprising 2 µCi of tracer [$^{125}$I cAMP (100 µl) to 11 ml Detection Buffer) are prepared and maintained in accordance with the manufacturer's instructions. Assay Buffer is prepared fresh for screening and contained 20 mM HEPES, pH 7.4, 10 mM $MgCl_2$, 20 mM (Sigma), 0.1 units/ml creatine phosphokinase (Sigma), 50 µM GTP (Sigma), and 0.2 mM ATP (Sigma); Assay Buffer can be stored on ice until utilized. The assay is initiated by addition of 50 ul of assay buffer followed by addition of 50 ul of membrane suspension to the NEN Flash Plate. The resultant assay mixture is incubated for 60 minutes at room temperature followed by addition of 100 ul of detection buffer. Plates are then incubated an additional 2-4 hours followed by counting in a Wallac MicroBeta™ scintillation counter. Values of cAMP/well are extrapolated from a standard cAMP curve that is contained within each assay plate.

C. Reporter-Based Assays

1. CREB Reporter Assay (Gs-Associated Receptors)

A method to detect Gs stimulation depends on the known property of the transcription factor CREB, which is activated in a cAMP-dependent manner. A PathDetect™ CREB trans-Reporting System (Stratagene, Catalogue #219010) can utilized to assay for Gs coupled activity in 293 or 293T cells. Cells are transfected with the plasmids components of this above system and the indicated expression plasmid encoding endogenous or mutant receptor using a Mammalian Transfection Kit (Stratagene, Catalogue #200285) according to the manufacturer's instructions. Briefly, 400 ng pFR-Luc (luciferase reporter plasmid containing Gal4 recognition sequences), 40 ng pFA2-CREB (Gal4-CREB fusion protein containing the Gal4 DNA-binding domain), 80 ng pCMV-receptor expression plasmid (comprising the receptor) and 20 ng CMV-SEAP (secreted alkaline phosphatase expression plasmid; alkaline phosphatase activity is measured in the media of transfected cells to control for variations in transfection efficiency between samples) are combined in a calcium phosphate precipitate as per the Kit's instructions. Half of the precipitate is equally distributed over 3 wells in a 96-well plate, kept on the cells overnight, and replaced with fresh medium the following morning. Forty-eight (48) hr after the start of the transfection, cells are treated and assayed for, e.g., luciferase activity 2. AP1 Reporter Assay (Gq-Associated Receptors)

A method to detect Gq stimulation depends on the known property of Gq-dependent phospholipase C to cause the activation of genes containing AP1 elements in their promoter. A Pathdetect™ AP-1 cis-Reporting System (Stratagene, Catalogue #219073) can be utilized following the protocol set forth above with respect to the CREB reporter assay, except that the components of the calcium phosphate precipitate were 410 ng pAP1-Luc, 80 ng pCMV-receptor expression plasmid, and 20 ng CMV-SEAP.

3. CRE-LUC Reporter Assay 293 and 293T cells are plated-out on 96 well plates at a density of $2 \times 10^4$ cells per well and were transfected using Lipofectamine Reagent (BRL) the following day according to manufacturer instructions. A DNA/lipid mixture is prepared for each 6-well transfection as follows: 260 ng of plasmid DNA in 100 µl of DMEM were gently mixed with 2 µl of lipid in 100 µl of DMEM (the 260 ng of plasmid DNA consisted of 200 ng of a 8×CRE-Luc reporter plasmid (see below and FIG. 1 for a representation of a portion of the plasmid), 50 ng of pCMV comprising endogenous receptor or non-endogenous receptor or pCMV alone, and 10 ng of a GPRS expression plasmid (GPRS in pcDNA3 (Invitrogen)). The 8×CRE-Luc reporter plasmid was prepared as follows: vector SRIF-β-gal was obtained by cloning the rat somatostatin promoter (−71/+51) at BglV-HindIII site in the pβgal-Basic Vector (Clontech). Eight (8) copies of cAMP response element were obtained by PCR from an adenovirus template AdpCF126CCRE8 (see, 7 *Human Gene Therapy* 1883 (1996)) and cloned into the SRIF-β-gal vector at the Kpn-BglV site, resulting in the 8×CRE-β-gal reporter vector. The 8×CRE-Luc reporter plasmid was generated by replacing the beta-galactosidase gene in the 8×CRE-β-gal reporter vector with the luciferase gene obtained from the pGL3-basic vector (Promega) at the HindIII-BamHI site. Following 30 min. incubation at room temperature, the DNA/lipid mixture was diluted with 400 µl of DMEM and 100 µl of the diluted mixture was added to each well. 100 µl of DMEM with 10% FCS were added to each well after a 4 hr incubation in a cell culture incubator. The following day the transfected cells were changed with 200 µl/well of DMEM with 10% FCS. Eight (8) hours later, the wells were changed to 100 µl/well of DMEM without phenol red, after one wash with PBS. Luciferase activity were measured the next day using the LucLite™ reporter gene assay kit (Packard) following manufacturer instructions and read on a 1450 MicroBeta™ scintillation and luminescence counter (Wallac).

4. SRF-LUC Reporter Assay

One method to detect Gq stimulation depends on the known property of Gq-dependent phospholipase C to cause the activation of genes containing serum response factors in their promoter. A Pathdetect™ SRF-Luc-Reporting System (Stratagene) can be utilized to assay for Gq coupled activity in, e.g., COS7 cells. Cells are transfected with the plasmid components of the system and the indicated expression plasmid encoding endogenous or non-endogenous GPCR using a Mammalian Transfection™ Kit (Stratagene, Catalogue #200285) according to the manufacturer's instructions. Briefly, 410 ng SRF-Luc, 80 ng pCMV-receptor expression plasmid and 20 ng CMV-SEAP (secreted alkaline phosphatase expression plasmid; alkaline phosphatase activity is measured in the media of transfected cells to control for variations in transfection efficiency between samples) are combined in a calcium phosphate precipitate as per the manufacturer's instructions. Half of the precipitate is equally distributed over 3 wells in a 96-well plate, kept on the cells in a serum free media for 24 hours. The last 5 hours the cells are incubated with 1 µM Angiotensin, where indicated. Cells are then lysed and assayed for luciferase activity using a Luclite™ Kit (Packard, Cat. #6016911) and "Trilux 1450 Microbeta" liquid scintillation and luminescence counter (Wallac) as per the manufacturer's instructions. The data can be analyzed using GraphPad Prism™ 2.0a (GraphPad Software Inc.).

5. Intracellular $IP_3$ Accumulation Assay

On day 1, cells comprising the receptors (endogenous and/or non-endogenous) can be plated onto 24 well plates, usually $1 \times 10^5$ cells/well (although his umber can be optimized. On day 2 cells can be transfected by firstly mixing 0.25 ug DNA in 50 ul serum free DMEM/well and 2 ul lipofectamine in 50 µl serumfree DMEM/well. The solutions are gently mixed and incubated for 15-30 min at room temperature. Cells are washed with 0.5 ml PBS and 400 µl of serum free media is mixed with the transfection media and added to the cells. The cells are then incubated for 3-4 hrs at 37° C./5% $CO_2$ and then the transfection media is removed and replaced with 1 ml/well of regular growth media. On day 3 the cells are labeled with $^3$H-myo-inositol. Briefly, the media is removed and the cells are washed with 0.5 ml PBS. Then 0.5 ml inositol-free/serum free media (GIBCO BRL) is added/well with 0.25 µCi of $^3$H-myo-inositol/well and the cells are incubated for 16-18 hrs o/n at 37° C./5% $CO_2$. On Day 4 the cells are washed with 0.5 ml PBS and 0.45 ml of assay medium is added containing inositol-free/serum free media 10 µM pargyline 10 mM lithium chloride or 0.4 ml of assay medium and 50 ul of 10× ketanserin (ket) to final concentration of 10 µM. The cells are then incubated for 30 min at 37° C. The cells are then washed with 0.5 ml PBSand 200 ul of fresh/icecold stop solution (1M KOH; 18 mM Na-borate; 3.8 mM EDTA) is added/well. The solution is kept on ice for 5-10 min or until cells were lysed and then neutralized by 200 μl of fresh/ice cold neutralization sol. (7.5% HCL). The lysate is then transferred into 1.5 ml eppendorf tubes and 1 ml of chloroform/methanol (1:2) is added/tube. The solution is vortexed for 15 sec and the upper phase is applied to a Biorad AG1-X8™ anion exchange resin (100-200 mesh). Firstly, the resin is washed with water at 1:1.25 W/V and 0.9 ml of upper phase is loaded onto the column. The column is washed with 10 mls of 5 mM myo-inositol and 10 ml of 5 mM Na-borate/60 mM Na-formate. The inositol tris phosphates are eluted into scintillation vials containing 10 ml of scintillation cocktail with 2 ml of 0.1 M formic acid/1 M ammonium formate. The columns are regenerated by washing with 10 ml of 0.1 M formic acid/3M ammonium formate and rinsed twice with dd $H_2O$ and stored at 4° C. in water.

Figure 5A:
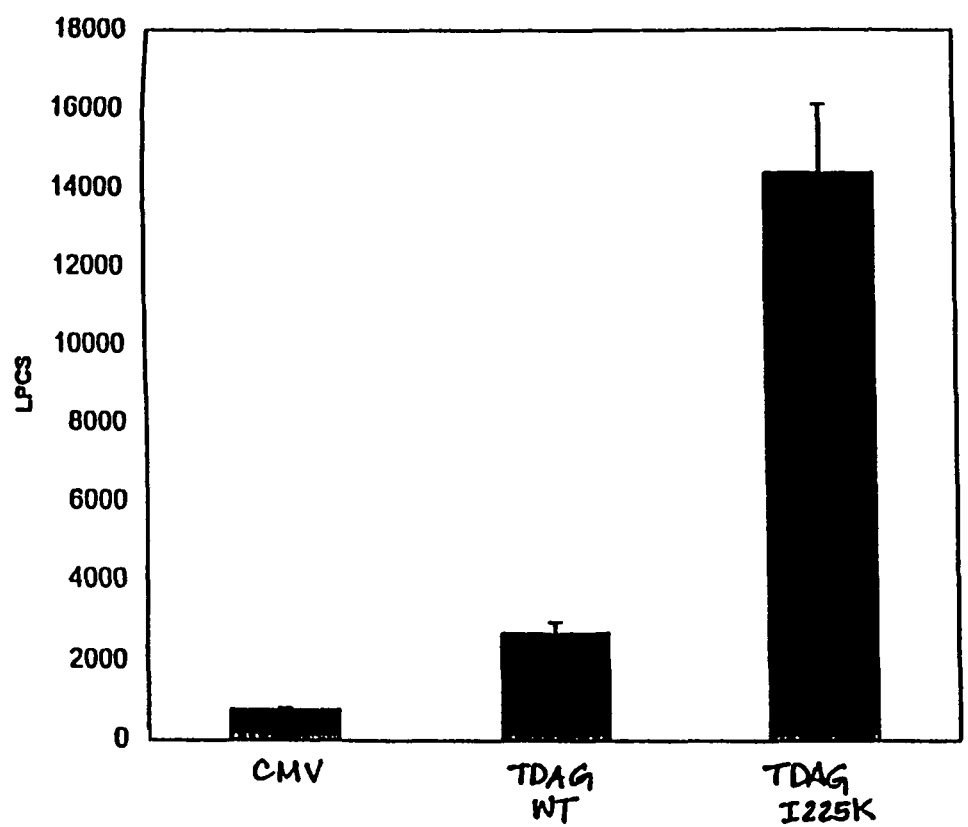
FIGS. 5A-5B provides graphic results of comparative analysis of endogenous TDAG8 ("WT") versus non-endogenous, constitutively active TDAG8 ("I225K") (control is designated "CMV") in 293 (5A) and 293T (5B) cells.
Figure 5B:
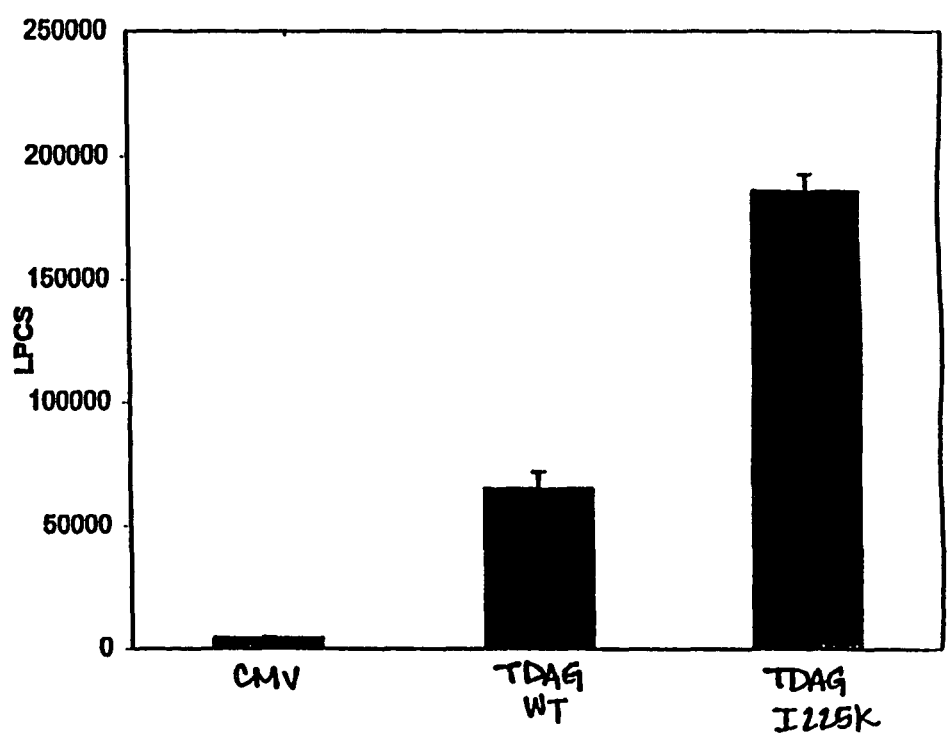

Exemplary results are presented below in Table I and, in the case of hTDAG8, also in histogram form in FIGS. 5A (293 cells) and 5B (293T cells).

TABLE I

| Receptor | Mutation | Assay Utilized | Signal Generated: Endogenous Version (Relative Light Units) | Signal Generated: Non-Endogenous Version (Relative Light Units) | Percent Difference |
|---|---|---|---|---|---|
| hAT1 | F239K | SRF-LUC | 34 | 137 | 300%↑ |
|  | AT2K255IC3 | SRF-LUC | 34 | 127 | 270%↑ |
| hTDAG8 | I225K | CRE-LUC (293 cells) | 2,715 | 14,440 | 430%↑ |
|  | I225K | CRE-LUC (293T cells) | 65,681 | 185,636 | 180%↑ |
| hH9 | F236K | CRE-LUC | 1,887 | 6,096 | 220%↑ |
| hCCKB | V332K | CRE-LUC | 785 | 3,223 | 310%↑ |

C. Cell-Based Detection Assay (Example-T$_{DAG}$8)

293 cells were plated-out on 150 mm plates at a density of $1.3 \times 10^7$ cells per plate, and were transfected using 12 ug of the respective DNA and 60 ul of Lipofectamine Reagent (BRL) per plate. The transfected cells were grown in media containing serum for an assay performed 24 hours post-transfection. For detection assay performed 48 hours post-transfection (assay comparing serum and serum-free media; see FIG. 3), the initial media was changed to either serum or serum-free media. The serum-free media was comprised solely of Dulbecco's Modified Eagle's (DME) High Glucose Medium (Irvine Scientific #9024). In addition to the above DME Medium, the media with serum contained the following: 10% Fetal Bovine Serum (Hyclone #SH30071.03), 1% of 100 mM Sodium Pyruvate (Irvine Scientific #9334), 1% of 20 mM L-Glutamine (Irvine Scientific #9317), and 1% of Penicillin-Streptomycin solution (Irvine Scientific #9366).

A 96-well Adenylyl Cyclase Activation Flashplate™ was used (NEN: #SMP004A). First, 50ul of the standards for the assay were added to the plate, in duplicate, ranging from concentrations of 50 pmol to zero pmol cAMP per well. The standard cAMP (NEN: #SMP004A) was reconstituted in water, and serial dilutions were made using 1×PBS (Irvine Scientific: #9240). Next, 50 ul of the stimulation buffer (NEN: #SMP004A) was added to all wells. In the case of using compounds to measure activation or inactivation of cAMP, 10 ul of each compound, diluted in water, was added to its respective well, in triplicate. Various final concentrations used range from 1 uM up to 1 mM. Adenosine 5'-triphosphate, ATP, (Research Biochemicals International: #A-141) and Adenosine 5'-diphosphate, ADP, (Sigma: #A2754) were used in the assay. Next, the 293 cells transfected with the respective cDNA (CMV or TDAG8) were harvested 24 (assay detection in serum media) or 48 hours post-transfection (assay detection comparing serum and serum-free media). The media was aspirated and the cells washed once with 1×PBS. Then 5 ml of 1×PBS was added to the cells along with 3 ml of cell dissociation buffer (Sigma: #C-1544). The detached cells were transferred to a centrifuge tube and centrifuged at room temperature for five minutes. The supernatant was removed and the cell pellet was resuspended in an appropriate amount of 1×PBS to obtain a final concentration of $2 \times 10^6$ cells per milliliter. To the wells containing the compound, 50 ul of the cells in 1×PBS ($1 \times 10^5$ cells/well) were added. The plate was incubated on a shaker for 15 minutes at room temperature. The detection buffer containing the tracer cAMP was prepared. In 11 ml of detection buffer (NEN: #SMP004A), 50 ul (equal to 1 uCi) of [$^{121}$I]cAMP (NEN: #SMP004A) was added. Following incubation, 50 ul of this detection buffer containing tracer cAMP was added to each well. The plate was placed on a shaker and incubated at room temperature for two hours. Finally, the solution from the wells of the plate were aspirated and the flashplate was counted using the Wallac MicroBeta™ scintillation counter.

Figure 2A:
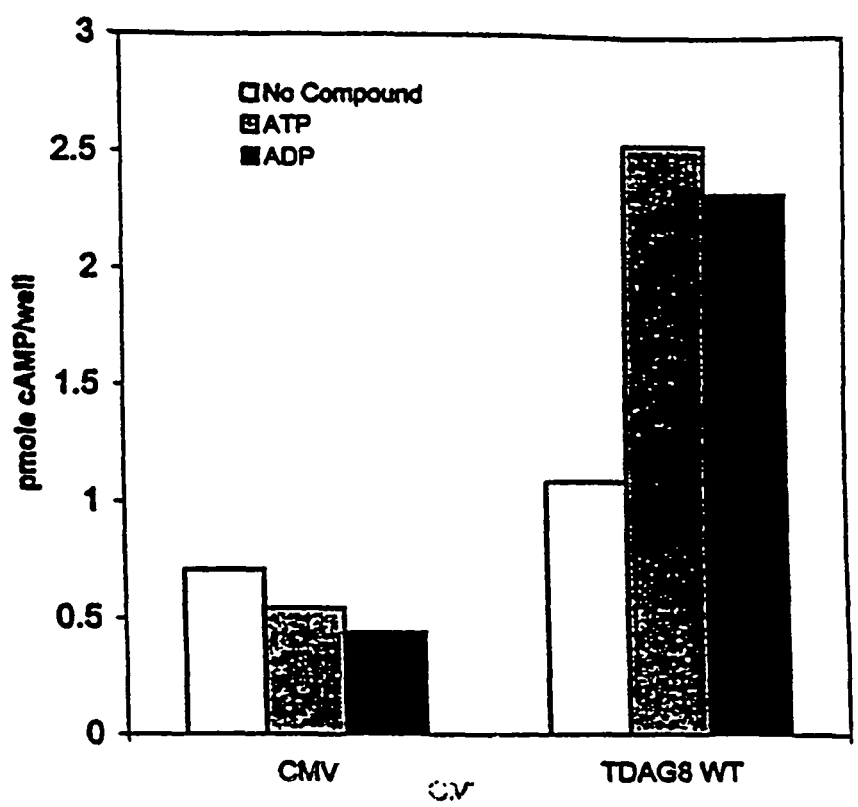
FIGS. 2A and 2B are graphic representations of the results of ATP and ADP binding to endogenous TDAG8 (2A) and comparisons in serum and serum free media (2B).
Figure 2B:
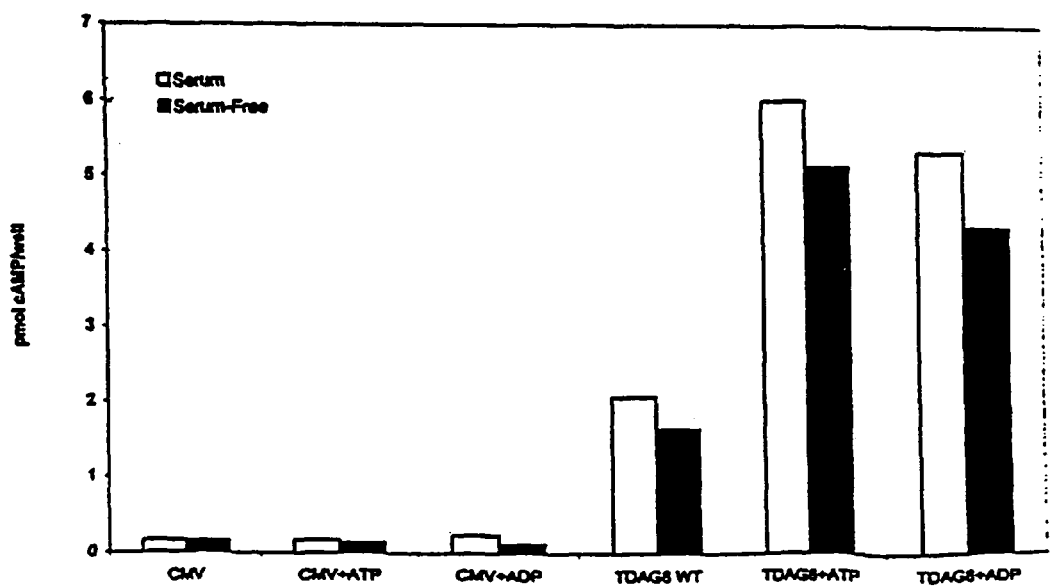
Figure 4A:
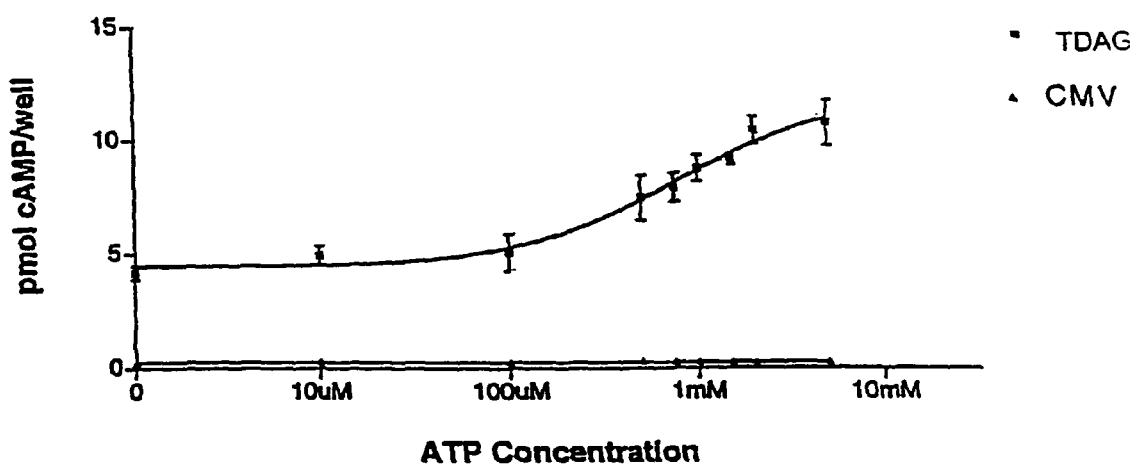
FIGS. 4A-4B is a representation of a dose response curve for endogenous, constitutively active TDAG8 ("TDAG8 WT") in 293 cell-based cAMP assay.
Figure 4B:
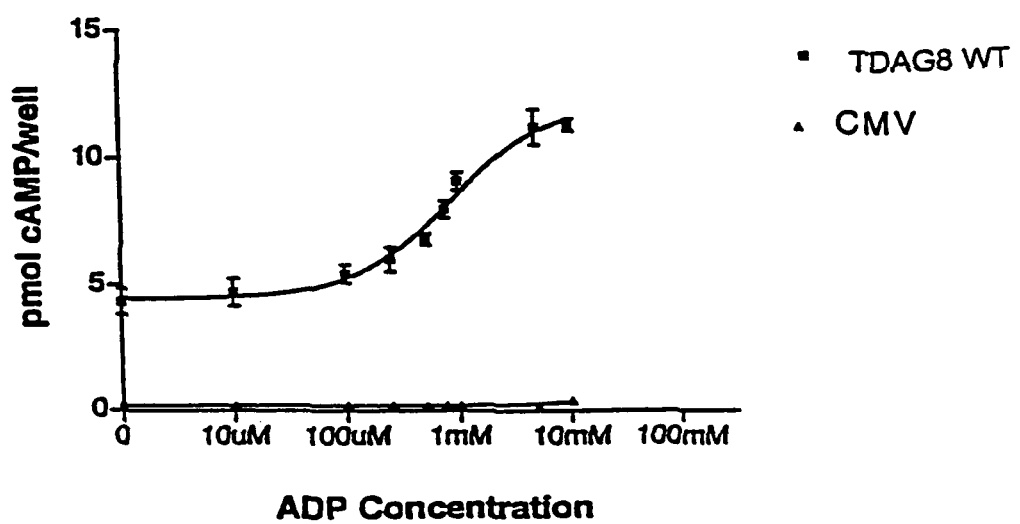

In FIG. 2A, ATP and ADP bind to endogenous TDAG8 resulting in an increase of cAMP of about 130% and about 110% respectively. FIG. 2B evidences ATP and ADP binding to endogenous TDAG8 where endogenous TDAG8 was transfected and grown in serum and serum-free medium. ATP binding to endogenous TDAG8 grown in serum media evidences an increase in cAMP of about 205%, compared to the endogenous TDAG8 with no compounds; in serum-free media there was an increase of about 220%. ADP binding to endogenous TDAG8 in serum evidences about a 165% increase, while in serum-free ADP binding evidences an increase of about 170% increase. ATP and ADP bind to endogenous TDAG8 with an EC50 value of 500 μM and 700 μM, respectively, as shown in FIGS. 4A and 4B.

Although the results presented in FIG. 2B indicate substantially the same results when serum and serum-free media were compared, our choice is to use a serum based media, although a serum-free media can also be utilized.

Example 6

GPCR Fusion Protein Preparation

The design of the constitutively activated GPCR-G protein fusion construct was accomplished as follows: both the 5' and 3' ends of the rat G protein Gsα (long form; Itoh, H. et al., 83 *PNAS* 3776 (1986)) were engineered to include a HindIII (5'-AAGCTT-3') sequence thereon. Following confirmation of the correct sequence (including the flanking HindIII sequences), the entire sequence was shuttled into pcDNA3.1 (−) (Invitrogen, cat. no. V795-20) by subcloning using the HindIII restriction site of that vector. The correct orientation for the Gsα sequence was determined after subcloning into pcDNA3.1(−). The modified pcDNA3.1(−) containing the rat Gsα gene at HindIII sequence was then verified; this vector was now available as a "universal" Gsα protein vector. The pcDNA3.1 (−) vector contains a variety of well-known restriction sites upstream of the HindIII site, thus beneficially providing the ability to insert, upstream of the Gs protein, the coding sequence of an endogenous, constitutively active GPCR. This same approach can be utilized to create other "universal" G protein vectors, and, of course, other commercially available or proprietary vectors known to the artisan can be utilized—the important criteria is that the sequence for the GPCR be upstream and in-frame with that of the G protein.

TDAG8 couples via Gs, while H9 couples via Gz. For the following exemplary GPCR Fusion Proteins, fusion to Gsα was accomplished.

A TDAG8(I225K)-Gsα Fusion Protein construct was made as follows: primers were designed as follows:
5'-TCTAGAATGAACAGCACATGTATTGAAG-3' (SEQ.ID.NO.:125; sense)
5'-GGTACCCGCTCAAGGACCTCTAATTCCATAG-3' (SEQ.ID.NO.:126; antisense).

Nucleotides in lower caps are included as spacers in the restriction sites between the G protein and TDAG8. The sense and anti-sense primers included the restriction sites for XbaI and KpnI, respectively.

PCR was then utilized to secure the respective receptor sequences for fusion within the Gsα universal vector disclosed above, using the following protocol for each: 100 ng cDNA for TDAG8 was added to separate tubes containing 2 ul of each primer (sense and anti-sense), 3 uL of 10 mM dNTPs, 10 uL of 10×TaqPlus™ Precision buffer, 1 uL of TaqPlus™ Precision polymerase (Stratagene: #600211), and 80 uL of water. Reaction temperatures and cycle times for TDAG8 were as follows: the initial denaturing step was done it 94° C. for five minutes, and a cycle of 94° C. for 30 seconds; 55° C. for 30 seconds; 72° C. for two minutes. A final extension time was done at 72° C. for ten minutes. PCR product for was run on a 1% agarose gel and then purified (data not shown). The purified product was digested with XbaI and KpnI (New England Biolabs) and the desired inserts purified and ligated into the Gs universal vector at the respective restriction site. The positive clones was isolated following transformation and determined by restriction enzyme digest; expression using 293 cells was accomplished following the protocol set forth infra. Each positive clone for TDAG8:Gs—Fusion Protein was sequenced to verify correctness.

GPCR Fusion Proteins comprising non-endogenous, constitutively activated TDAG8(I225K) were analyzed as above and verified for constitutive activation.

An H9(F236K)-Gsα Fusion Protein construct was made as follows: primers were designed as follows:
5'-TTAgatatcGGGGCCCACCCTAGCGGT-3' (SEQ.ID.NO.:145; sense)
5'-ggtaccCCCACAGCCATTTCATCAGGATC-3' (SEQ.ID.NO.:146; antisense).

Nucleotides in lower caps are included as spacers in the restriction sites between the G protein and H9. The sense and anti-sense primers included the restriction sites for EcoRV and KpnI, respectively such that spacers (attributed to the restriction sites) exists between the G protein and H9.

PCR was then utilized to secure the respective receptor sequences for fusion within the Gsα universal vector disclosed above, using the following protocol for each: 80 ng cDNA for H9 was added to separate tubes containing 100 ng of each primer (sense and anti-sense), and 45 uL of PCR Supermix™ (Gibco-Brl, LifeTech) (50 ul total reaction volume). Reaction temperatures and cycle times for H9 were as follows: the initial denaturing step was done it 94° C. for one, and a cycle of 94° C. for 30 seconds; 55° C. for 30 seconds; 72° C. for two minutes. A final extension time was done at 72° C. for seven minutes. PCR product for was run on a 1% agarose gel and then purified (data not shown). The purified product was cloned into pCRII-TOPO™ System followed by identification of positive clones. Positive clones were isolated, digested with EcoRV and KpnI (New England Biolabs) and the desired inserts were isolated, purified and ligated into the Gs universal vector at the respective restriction site. The positive clones was isolated following transformation and determined by restriction enzyme digest; expression using 293 cells was accomplished following the protocol set forth infra. Each positive clone for H9(F236K):Gs—Fusion Protein was sequenced to verify correctness. Membranes were frozen (−80° C.) until utilized.

To ascertain the ability of measuring a cAMP response mediated by the Gs protein (even though H9 couples with Gz), the following cAMP membrane assay was utilized, based upon an NEN Adenyl Cyclase Activation Flahplate™ Assay kit (96 well format). "Binding Buffer" consisted of 10 mM HEPES, 100 mM NaCl and 10 mM MgCl (ph 7.4). "Regeneration Buffer" was prepared in Binding Buffer and consisted of 20 mM phosphocreatine, 20U creatine phosphokinase, 20 uM GTP, 0.2 mM ATP, and 0.6 mM IBMX. "cAMP Standards" were prepared in Binding Buffer as follows:

| | cAMP Stock (5,000 pmol/ml in 2 ml H$_2$O) in ul | Added to indicted amount of Binding Buffer | Final Assay Concentration (50 ul into 100 ul) to achieve indicated pmol/well |
|---|---|---|---|
| A | 250 | 1 ml | 50 |
| B | 500 of A | 500 ul | 25 |
| C | 500 of B | 500 ul | 12.5 |
| D | 500 of C | 750 ul | 5.0 |
| E | 500 of D | 500 ul | 2.5 |
| F | 500 of E | 500 ul | 1.25 |
| G | 500 of F | 750 ul | 0.5 |

Frozen membranes (both pCMV as control and the non-endogenous H(—Gs Fusion Protein) were thawed (on ice at room temperature until in solution). Membranes were homogenized with a polytron until in suspension (2×15 seconds). Membrane protein concentration was determined using the Bradford Assay Protocol (see infra). Membrane concentration was diluted to 0.5 mg/ml in Regeneration Buffer (final assay concentration—25 ug/well). Thereafter, 50 ul of Binding Buffer was added to each well. For control, 50 ul/well of cAMP standard was added to wells 11 and 12 A-G, with Binding Buffer alone to 12H (on the 96-well format). Thereafter, 50 ul/well of protein was added to the wells and incubated at room temperature (on shaker) for 60 min. 100 ul[$^{125}$I]cAMP in Detection Buffer (see infra) was added to each well (final—50 ul[$^{125}$I]cAMP into 11 ml Detection Buffer). These were incubated for 2 hrs at room temperature. Plates were aspirated with an 8 channel manifold and sealed with plate covers. Results (pmoles cAMP bound) were read in a Wallac™ 1450 on "prot #15). Results are presented in FIG. 3.

Figure 3:
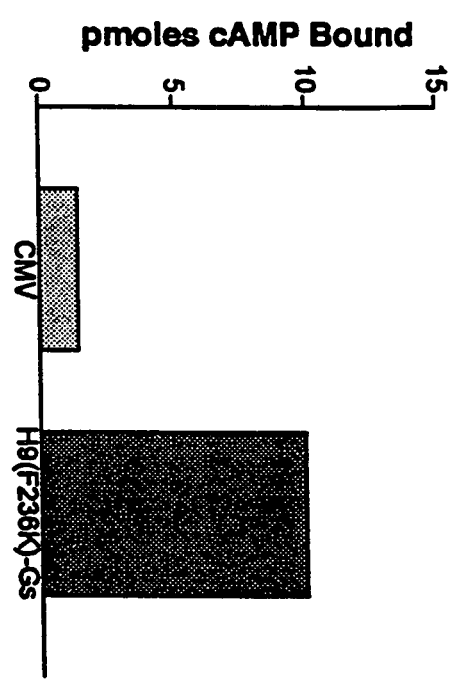
FIG. 3 is a graphic representation of the comparative signaling results of CMV versus the GPCR Fusion Protein H9(F236K):Gsα.

The reuslts presented in FIG. 3 indicate that the Gs coupled fusion was able to "drive" the cyclase reaction such that measurement of the consitutive activation of H9(F236K) was viable. Based upon these results, the direct identification of candidate compounds that are inverse agonists, agonists and partial agonists is possible using a cyclase-based assay.

Example 7

Protocol: Direct Identification of Inverse Agonists and Agonists Using [$^{35}$S]GTPγS Although we have utilized endogenous, constitutively active GPCRs for the direct identification of candidate compounds as, e.g., inverse agonists, for reasons that are not altogether understood, intra-assay variation can become exacerbated. Preferably, then, a GPCR Fusion Protein, as disclosed above, is also utilized with a non-endogenous, constitutively activated GPCR. We have determined that when such a protein is used, intra-assay variation appears to be substantially stabilized, whereby an effective signal-to-noise ratio is obtained. This has the beneficial result of allowing for a more robust identification of candidate compounds. Thus, it is preferred that for direct identification, a GPCR Fusion Protein be used and that when utilized, the following assay protocols be utilized.

Membrane Preparation

Membranes comprising the non-endogenous, constitutively active orphan GPCR Fusion Protein of interest and for use in the direct identification of candidate compounds as inverse agonists, agonists or partial agonists are preferably prepared as follows:

a. Materials

"Membrane Scrape Buffer" is comprised of 20 mM HEPES and 10 mM EDTA, pH 7.4; "Membrane Wash Buffer" is comprised of 20 mM HEPES and 0.1 mM EDTA, pH 7.4; "Binding Buffer" is comprised of 20 mM HEPES, 100 mM NaCl, and 10 mM $MgCl_2$, pH 7.4 b. Procedure

All materials are kept on ice throughout the procedure. Firstly, the media is aspirated from a confluent monolayer of cells, followed by rinse with 10 ml cold PBS, followed by aspiration. Thereafter, 5 ml of Membrane Scrape Buffer is added to scrape cells; this is followed by transfer of cellular extract into 50 ml centrifuge tubes (centrifuged at 20,000 rpm for 17 minutes at 4° C.). Thereafter, the supernatant is aspirated and the pellet is resuspended in 30 ml Membrane Wash Buffer followed by centrifuge at 20,000 rpm for 17 minutes at 4° C. The supernatant is then aspirated and the pellet resuspended in Binding Buffer. This is then homogenized using a Brinkman polytron™ homogenizer (15-20 second bursts until the all material is in suspension). This is referred to herein as "Membrane Protein".

Bradford Protein Assay

Following the homogenization, protein concentration of the membranes is determined using the Bradford Protein Assay (protein can be diluted to about 1.5 mg/ml, aliquoted and frozen (−80° C.) for later use; when frozen, protocol for use is as follows: on the day of the assay, frozen Membrane Protein is thawed at room temperature, followed by vortex and then homogenized with a polytron at about 12×1,000 rpm for about 5-10 seconds; it is noted that for multiple preparations, the homogenizor should be thoroughly cleaned between homoginezation of different preparations).

a. Materials

Binding Buffer (as per above); Bradford Dye Reagent; Bradford Protein Standard are utilized, following manufacturer instructions (Biorad, cat. no. 500-0006).

b. Procedure

Duplicate tubes are prepared, one including the membrane, and one as a control "blank". Each contained 800 ul Binding Buffer. Thereafter, 10 ul of Bradford Protein Standard (1 mg/ml) is added to each tube, and 10 ul of membrane Protein is then added to just one tube (not the blank). Thereafter, 200 ul of Bradford Dye Reagent is added to each tube, followed by vortex of each. After five (5) minutes, the tubes were re-vortexed and the material therein is transferred to cuvettes. The cuvettes are then read using a CECIL 3041 spectrophotometer, at wavelength 595.

Direct Identification Assay a. Materials

GDP Buffer consists of 37.5 ml Binding Buffer and 2 mg GDP (Sigma, cat. no. G-7127), followed by a series of dilutions in Binding Buffer to obtain 0.2 uM GDP (final concentration of GDP in each well was 0.1 uM GDP); each well comprising a candidate compound, has a final volume of 200 ul consisting of 100 ul GDP Buffer (final concentration, 0.1 uM GDP), 50 ul Membrane Protein in Binding Buffer, and 50 ul [$^{35}$S]GTPγS (0.6 nM) in Binding Buffer (2.5 ul [$^{35}$S]GTPγS per 10 ml Binding Buffer).

b. Procedure

Candidate compounds are preferably screened using a 96-well plate format (these can be frozen at −80° C). Membrane Protein (or membranes with expression vector excluding the GPCR Fusion Protein, as control), are homogenized briefly until in suspension. Protein concentration is then determined using the Bradford Protein Assay set forth above. Membrane Protein (and control) is then diluted to 0.25 mg/ml in Binding Buffer (final assay concentration, 12.5 ug/well). Thereafter, 100 ul GDP Buffer is added to each well of a Wallac Scintistrip™ (Wallac). A 5 ul pin-tool is then used to transfer 5 ul of a candidate compound into such well (i.e., 5 ul in total assay volume of 200 ul is a 1:40 ratio such that the final screening concentration of the candidate compound is 10 uM). Again, to avoid contamination, after each transfer step the pin tool should be rinsed in three reservoirs comprising water (1×), ethanol (1×) and water (2×)—excess liquid should be shaken from the tool after each rinse and dried with paper and kimwipes. Thereafter, 50 ul of Membrane Protein is added to each well (a control well comprising membranes without the GPCR Fusion Protein is also utilized), and pre-incubated for 5-10 minutes at room temperature. Thereafter, 50 ul of [$^{35}$S]GTPγS (0.6 nM) in Binding Buffer is added to each well, followed by incubation on a shaker for 60 minutes at room temperature (again, in this example, plates were covered with foil). The assay is then stopped by spinning of the plates at 4000 RPM for 15 minutes at 22° C. The plates are then aspirated with an 8 channel manifold and sealed with plate covers. The plates are then read on a Wallacc 1450 using setting "Prot. #37" (as per manufacturer instructions).

Example 8

Protocol: Confirmation Assay

Using an independent assay approach to provide confirmation of a directly identified candidate compound as set forth above, it is preferred that a confirmation assay then be utilized. In this case, the preferred confirmation assay is a cyclase-based assay.

A modified Flash Plate™ Adenylyl Cyclase kit (New England Nuclear; Cat. No. SMP004A) is preferably utilized for confirmation of candidate compounds directly identified as inverse agonists and agonists to non-endogenous, constitutively activated orphan GPCRs in accordance with the following protocol.

Transfected cells are harvested approximately three days after transfection. Membranes are prepared by homogenization of suspended cells in buffer containing 20 mM HEPES, pH 7.4 and 10 mM $MgCl_2$. Homogenization is performed on ice using a Brinkman Polytron™ for approximately 10 seconds. The resulting homogenate is centrifuged at 49,000×g for 15 minutes at 4° C. The resulting pellet is then resuspended in buffer containing 20 mM HEPES, pH 7.4 and 0.1 mM EDTA, homogenized for 10 seconds, followed by centrifugation at 49,000×g for 15 minutes at 4° C. The resulting pellet can be stored at −80° C. until utilized. On the day of direct identification screening, the membrane pellet is slowly thawed at room temperature, resuspended in buffer containing 20 mM HEPES, pH 7.4 and 10 mM MgCL2, to yield a final protein concentration of 0.60 mg/ml (the resuspended membranes are placed on ice until use).

cAMP standards and Detection Buffer (comprising 2 µCi of tracer [$^{125}$I] cAMP (100 µl] to 11 ml Detection Buffer) are prepared and maintained in accordance with the manufacturer's instructions. Assay Buffer is prepared fresh for screening and contained 20 mM HEPES, pH 7.4, 10 mM MgCl$_2$, 20 mM phosocreatine (Sigma), 0.1 units/ml creatine phosphokinase (Sigma), 50 µM GTP (Sigma), and 0.2 mM ATP (Sigma); Assay Buffer can be stored on ice until utilized.

Candidate compounds identified as per above (if frozen, thawed at room temperature) are added, preferably, to 96-well plate wells (3 µl/well; 12 µM final assay concentration), together with 40 µl Membrane Protein (30 µg/well) and 50 µl of Assay Buffer. This admixture is then incubated for 30 minutes at room temperature, with gentle shaking.

Following the incubation, 100 µl of Detection Buffer is added to each well, followed by incubation for 2-24 hours. Plates are then counted in a Wallac MicroBeta™ plate reader using "Prot. #31" (as per manufacturer instructions).

Example 9

Tissue Distribution of TDAG8

Before using a multiple tissue cDNA ("MTC") panel, two primers were designed from the TDAG8 open reading frame sequence. The oligonucleotides utilized were as follows:
5'-GCACTCATGGTCAGCCTGTCCATC-3' (SEQ.ID.NO.: 154; sense)
5'-GTACAGAATTGGATCAGCAACAC-3' (SEQ.ID.NO.: 155; antisense).

Figure 6:
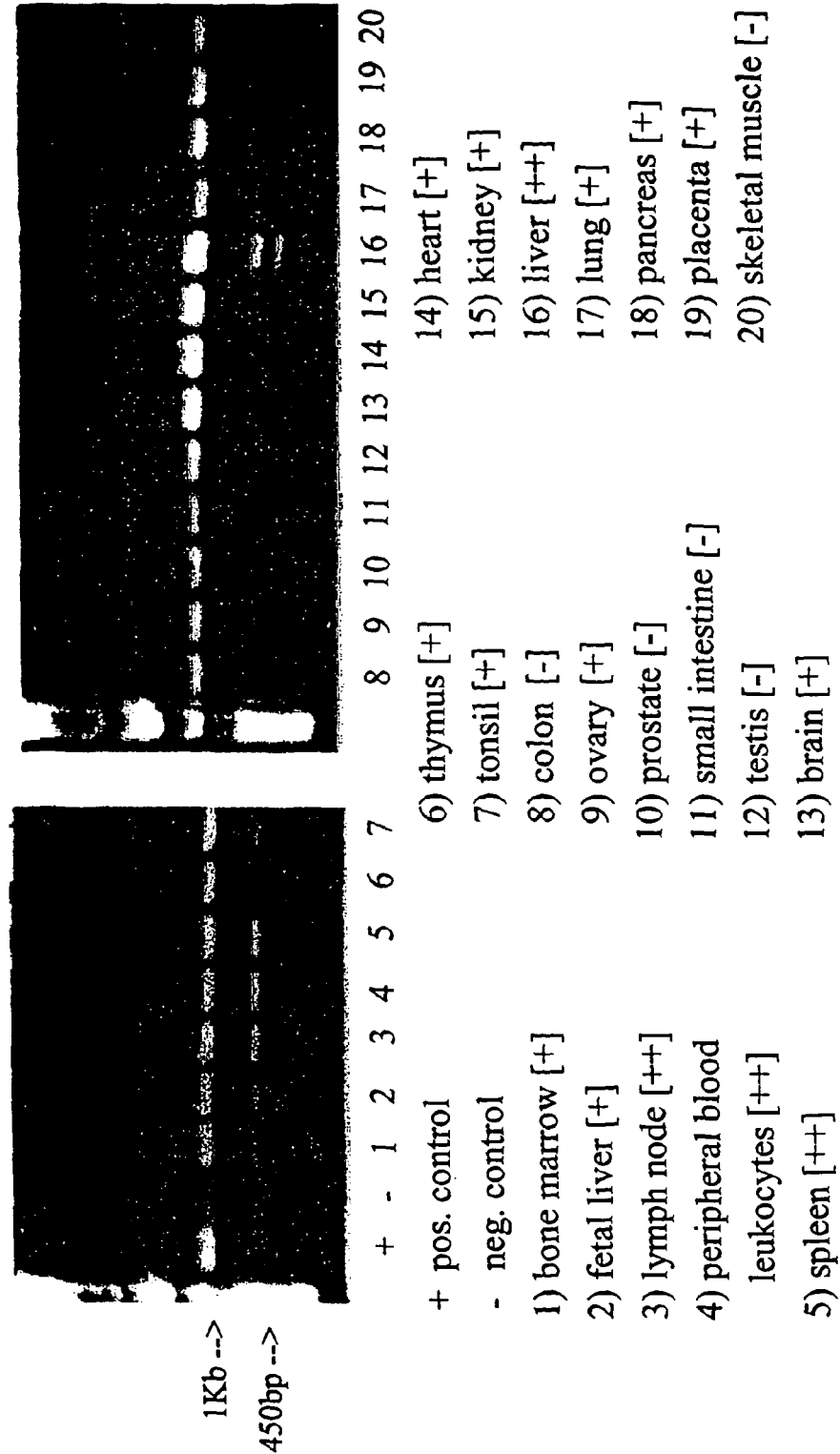
FIG. 6 is a reproduction of results of a tissue distribution of TDAG8 against various tissue-source mRNA's.

Once the two primers were made and purified for PCR use, the reaction mixes were made. Each tube contained the following master mix of reagents: 36 µl water, 1 µl 10 mM dNTP mix, 1 ul Taq Plus Precision DNA Polymerase (Stratagene: #600211), and 5 µl 10× Buffer for Taq Plus Precision Polymerase (Stratagene: #600211). A positive control tube containing the above solutions also contained 2 µl of the G3PDH positive control primers (Clontech: #K14261-1) and 5 µl of the control cDNA (Clontech: #K1426-1). A negative control tube was similar to the positive control; however, the control cDNA was replaced with 5 µl water. To determine gene distribution, the MTC Panels used included the Human Panel I (Clontech: #K1420-1), the Human Panel II (Clontech: #K1421-1), and the Human Immune System Panel (Clontech: #K1426-1). Each MTC Panel contained several tubes of cDNA from various human tissues. Using tubes containing the above master mix of reagents, 2 µl of the G3PDH positive control primers, 5 µl of the individual MTC Panel cDNA, and 1 µl of each primer designed above for the TDAG8 gene were all added to complete the reaction mixture. All of the tubes were then placed into a programmable thermal cycler (Perkin Elmer). The reactions were added at 94° C. for 30 seconds. A cycle of 94° C. for 30 seconds, 55° C. for 30 seconds, and 72° C. for two minutes was repeated 30 times. A final extension time of five minutes at 72° C. was run, and the cooling temperature of 4° C. was the final step. The reactions were added to a one percent agarose gel (FMC Bioproducts: #50004) and examined under ultraviolet light. For the positive control, an expected band of approximately 1 Kb should be seen. For the negative control, no band should appear. Finally, for all of the tubes containing various human tissue cDNA, a band should be seen at 1 Kb (for the control primers), and if expressed in that particular tissue, a band (varying in intensity) should be seen at 450 bp (for the TDAG8 primers). See FIG. 6.

Although a variety of expression vectors are available to those in the art, for purposes of utilization for the endogenous and non-endogenous human TDAG8, as well as the GPCR Fusion Protein comprising endogenous and non-endogenous TDAG8, it is most preferred that the vector utilized be pCMV. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be. The ATCC has assigned the following deposit number to pCMV: ATCC#203351.

What is claimed is:

1. A method of screening for a compound that increases cAMP levels in peripheral blood leukocytes, comprising:
   (a) contacting a candidate compound with a G protein-coupled receptor (GPCR) that is present on the surface of a recombinant host cell or isolated membrane thereof, wherein said GPCR comprises an amino acid sequence that is at least 80% identical to the amino acid sequence of SEQ ID NO:82; and
   (b) determining that said candidate compound is an agonist of said GPCR; and
   (c) determining if said agonist increases cAMP levels in a peripheral blood leukocyte.

2. The method of claim 1, wherein said determining step (b) comprises: determining if said candidate compound is a partial agonist of said GPCR.

3. The method of claim 1, wherein said determining step (b) and/or said determining step (c) comprises detecting cAMP.

4. The method of claim 3, wherein said detecting cAMP employs ELISA using an anti-cAMP antibody.

5. The method of claim 3, wherein the recombinant host cell comprises a reporter system comprising multiple cAMP responsive elements operably linked to a reporter gene.

6. The method of claim 3, wherein said detecting cAMP comprises detecting an increase in intracellular cAMP accumulation.

7. The method of claim 1, wherein said determining step (b) comprises using [35S]GTPγS to monitor G protein coupling to a membrane comprising said GPCR.

8. The method of claim 1, wherein said GPCR comprises an amino acid sequence that is at least 90% identical to the amino acid sequence of SEQ ID NO:82.

9. The method of claim 1, wherein said GPCR comprises an amino acid sequence that is at least 95% identical to the amino acid sequence of SEQ ID NO:82.

10. The method of claim 1, wherein said GPCR comprises an amino acid sequence that is at least 99% identical to the amino acid sequence of SEQ ID NO:82.

11. The method of claim 1, wherein the GPCR comprises one or more of the following amino acid substitutions: P43A, K97N or I130F, relative to SEQ ID NO:82.

12. The method of claim 1, wherein said GPCR is constitutively active.

13. The method of claim 1, wherein the GPCR comprises the following amino acid substitution: I225K, relative to SEQ ID NO:82.

14. The method of claim 1, wherein the method further comprises formulating said agonist as a pharmaceutical.

15. The method of claim 1, wherein the GPCR forms part of a fusion protein with a G protein.

16. The method of claim 1, wherein the host cell is a mammalian host cell.

17. The method of claim 1, wherein the host cell is a yeast host cell.

18. The method of claim 1, wherein the recombinant host cell comprises an expression vector which comprises a nucleic acid encoding said GPCR.

19. The method of claim 1, wherein said method further comprises determining whether said agonist increases cAMP levels in a peripheral blood leukocyte.

20. The method of claim 19, wherein the peripheral blood leukocyte is a human peripheral blood leukocyte.

* * * * *

UNITED STATES PATENT AND TRADEMARK OFFICE
CERTIFICATE OF CORRECTION

| | | |
|---|---|---|
| PATENT NO. | : 8,440,391 B2 | Page 1 of 1 |
| APPLICATION NO. | : 10/723955 | |
| DATED | : May 14, 2013 | |
| INVENTOR(S) | : Ruoping Chen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1992 days.

Signed and Sealed this
Second Day of December, 2014

Michelle K. Lee
*Deputy Director of the United States Patent and Trademark Office*

SEQUENCE LISTING

```
<160> NUMBER OF SEQ ID NOS: 148

<210> SEQ ID NO 1
<211> LENGTH: 1260
<212> TYPE: DNA
<213> ORGANISM: Homo sapiens

<400> SEQUENCE: 1
atggtcttct cggcagtgtt gactgcgttc cataccggga catccaacac aacatttgtc      60
gtgtatgaaa acacctacat gaatattaca ctccctccac cattccagca tcctgacctc     120
agtccattgc ttagatatag ttttgaaacc atggctccca ctggtttgag ttccttgacc     180
gtgaatagta cagctgtgcc cacaacacca gcagcattta agagcctaaa cttgcctctt     240
cagatcaccc tttctgctat aatgatattc attctgtttg tgtcttttct tgggaacttg     300
gttgtttgcc tcatggttta ccaaaaagct gccatgaggt ctgcaattaa catcctcctt     360
gccagcctag cttttgcaga catgttgctt gcagtgctga acatgccctt tgccctggta     420
actattctta ctacccgatg gattttttggg aaattcttct gtagggtatc tgctatgttt     480
ttctggttat ttgtgataga aggagtagcc atcctgctca tcattagcat agataggttc     540
```

```
cttattatag tccagaggca ggataagcta aacccatata gagctaaggt tctgattgca    600
gtttcttggg caacttcctt ttgtgtagct tttcctttag ccgtaggaaa ccccgacctg    660
cagatacctt cccgagctcc ccagtgtgtg tttgggtaca caaccaatcc aggctaccag    720
gcttatgtga ttttgatttc tctcatttct ttcttcatac ccttcctggt aatactgtac    780
tcatttatgg gcatactcaa cacccttcgg cacaatgcct tgaggatcca tagctaccct    840
gaaggtatat gcctcagcca ggccagcaaa ctgggtctca tgagtctgca gagacctttc    900
cagatgagca ttgacatggg ctttaaaaca cgtgccttca ccactatttt gattctcttt    960
gctgtcttca ttgtctgctg ggccccattc accacttaca gccttgtggc aacattcagt   1020
aagcactttt actatcagca caactttttt gagattagca cctggctact gtggctctgc   1080
tacctcaagt ctgcattgaa tccgctgatc tactactgga ggattaagaa attccatgat   1140
gcttgcctgg acatgatgcc taagtccttc aagttttgc cgcagctccc tggtcacaca   1200
aagcgacgga tacgtcctag tgctgtctat gtgtgtgggg aacatcggac ggtggtgtga   1260
```

<210> SEQ ID NO 2
<211> LENGTH: 419
<212> TYPE: PRT
<213> ORGANISM: Homo sapiens

<400> SEQUENCE: 2

```
Met Val Phe Ser Ala Val Leu Thr Ala Phe His Thr Gly Thr Ser Asn
1               5                   10                  15

Thr Thr Phe Val Val Tyr Glu Asn Thr Tyr Met Asn Ile Thr Leu Pro
            20                  25                  30

Pro Pro Phe Gln His Pro Asp Leu Ser Pro Leu Leu Arg Tyr Ser Phe
        35                  40                  45

Glu Thr Met Ala Pro Thr Gly Leu Ser Ser Leu Thr Val Asn Ser Thr
    50                  55                  60

Ala Val Pro Thr Thr Pro Ala Ala Phe Lys Ser Leu Asn Leu Pro Leu
65                  70                  75                  80

Gln Ile Thr Leu Ser Ala Ile Met Ile Phe Ile Leu Phe Val Ser Phe
                85                  90                  95

Leu Gly Asn Leu Val Val Cys Leu Met Val Tyr Gln Lys Ala Ala Met
            100                 105                 110

Arg Ser Ala Ile Asn Ile Leu Leu Ala Ser Leu Ala Phe Ala Asp Met
        115                 120                 125

Leu Leu Ala Val Leu Asn Met Pro Phe Ala Leu Val Thr Ile Leu Thr
    130                 135                 140

Thr Arg Trp Ile Phe Gly Lys Phe Phe Cys Arg Val Ser Ala Met Phe
145                 150                 155                 160

Phe Trp Leu Phe Val Ile Glu Gly Val Ala Ile Leu Leu Ile Ile Ser
                165                 170                 175

Ile Asp Arg Phe Leu Ile Ile Val Gln Arg Gln Asp Lys Leu Asn Pro
            180                 185                 190

Tyr Arg Ala Lys Val Leu Ile Ala Val Ser Trp Ala Thr Ser Phe Cys
        195                 200                 205

Val Ala Phe Pro Leu Ala Val Gly Asn Pro Asp Leu Gln Ile Pro Ser
    210                 215                 220

Arg Ala Pro Gln Cys Val Phe Gly Tyr Thr Thr Asn Pro Gly Tyr Gln
225                 230                 235                 240

Ala Tyr Val Ile Leu Ile Ser Leu Ile Ser Phe Phe Ile Pro Phe Leu
                245                 250                 255
```

| | | | | | | | | | | | | |
|---|---|---|---|---|---|---|---|---|---|---|---|---|
|Val|Ile|Leu|Tyr|Ser|Phe|Met|Gly|Ile|Leu|Asn|Thr|Leu|Arg|His|Asn|
| | | |260| | | |265| | | |270| | | | |

Val Ile Leu Tyr Ser Phe Met Gly Ile Leu Asn Thr Leu Arg His Asn
           260                 265             270

Ala Leu Arg Ile His Ser Tyr Pro Glu Gly Ile Cys Leu Ser Gln Ala
       275              280             285

Ser Lys Leu Gly Leu Met Ser Leu Gln Arg Pro Phe Gln Met Ser Ile
290              295             300

Asp Met Gly Phe Lys Thr Arg Ala Phe Thr Thr Ile Leu Ile Leu Phe
305             310              315           320

Ala Val Phe Ile Val Cys Trp Ala Pro Phe Thr Thr Tyr Ser Leu Val
           325              330           335

Ala Thr Phe Ser Lys His Phe Tyr Tyr Gln His Asn Phe Phe Glu Ile
           340              345           350

Ser Thr Trp Leu Leu Trp Leu Cys Tyr Leu Lys Ser Ala Leu Asn Pro
       355              360             365

Leu Ile Tyr Tyr Trp Arg Ile Lys Lys Phe His Asp Ala Cys Leu Asp
    370               375            380

Met Met Pro Lys Ser Phe Lys Phe Leu Pro Gln Leu Pro Gly His Thr
385              390             395           400

Lys Arg Arg Ile Arg Pro Ser Ala Val Tyr Val Cys Gly Glu His Arg
           405              410           415

Thr Val Val

<210> SEQ ID NO 3
<211> LENGTH: 1119
<212> TYPE: DNA
<213> ORGANISM: Homo sapiens

<400> SEQUENCE: 3

```
atgttagcca acagctcctc aaccaacagt tctgttctcc cgtgtcctga ctaccgacct      60
acccaccgcc tgcacttggt ggtctacagc ttggtgctgg ctgccgggct cccctcaac     120
gcgctagccc tctgggtctt cctgcgcgcg ctgcgcgtgc actcggtggt gagcgtgtac    180
atgtgtaacc tggcggccag cgacctgctc ttcaccctct cgctgcccgt tcgtctctcc    240
tactacgcac tgcaccactg gcccttcccc gacctcctgt gccagacgac gggcgccatc    300
ttccagatga acatgtacgg cagctgcatc ttcctgatgc tcatcaacgt ggaccgctac    360
gccgccatcg tgcaccgct gcgactgcgc acctgcggc ggccccgcgt ggcgcggctg     420
ctctgcctgg gcgtgtgggc gctcatcctg gtgtttgccg tgcccgccgc ccgcgtgcac    480
aggccctcgc gttgccgcta ccgggacctc gaggtgcgcc tatgcttcga gagcttcagc    540
gacgagctgt ggaaaggcag gctgctgccc ctcgtgctgc tggccgaggc gctgggcttc    600
ctgctgcccc tggcggcgt ggtctactcg tcgggccgag tcttctggac gctggcgcgc     660
cccgacgcca cgcagagcca gcggcggcgg aagaccgtgc gcctcctgct ggctaacctc    720
gtcatcttcc tgctgtgctt cgtgccctac aacagcacgc tggcggtcta cgggctgctg    780
cggagcaagc tggtggcggc cagcgtgcct gccgcgatc gcgtgcgcgg ggtgctgatg     840
gtgatggtgc tgctggccgg cgccaactgc gtgctggacc gctggtgta ctactttagc     900
gccgagggct tccgcaacac cctgcgcggc ctgggcactc cgcaccgggc caggacctcg    960
gccaccaacg ggacgcgggc ggcgctcgcg caatccgaaa ggtccgccgt caccaccgac   1020
gccaccaggc cggatgccgc cagtcagggg ctgctccgac cctccgactc ccactctctg   1080
tcttccttca cacagtgtcc ccaggattcc gccctctga                          1119
```

<210> SEQ ID NO 4

<211> LENGTH: 372
<212> TYPE: PRT
<213> ORGANISM: Homo sapiens

<400> SEQUENCE: 4

```
Met Leu Ala Asn Ser Ser Thr Asn Ser Ser Val Leu Pro Cys Pro
1               5                   10                  15

Asp Tyr Arg Pro Thr His Arg Leu His Leu Val Val Tyr Ser Leu Val
            20                  25                  30

Leu Ala Ala Gly Leu Pro Leu Asn Ala Leu Ala Leu Trp Val Phe Leu
        35                  40                  45

Arg Ala Leu Arg Val His Ser Val Val Ser Val Tyr Met Cys Asn Leu
50                  55                  60

Ala Ala Ser Asp Leu Leu Phe Thr Leu Ser Leu Pro Val Arg Leu Ser
65                  70                  75                  80

Tyr Tyr Ala Leu His His Trp Pro Phe Pro Asp Leu Leu Cys Gln Thr
                85                  90                  95

Thr Gly Ala Ile Phe Gln Met Asn Met Tyr Gly Ser Cys Ile Phe Leu
            100                 105                 110

Met Leu Ile Asn Val Asp Arg Tyr Ala Ala Ile Val His Pro Leu Arg
        115                 120                 125

Leu Arg His Leu Arg Arg Pro Arg Val Ala Arg Leu Leu Cys Leu Gly
    130                 135                 140

Val Trp Ala Leu Ile Leu Val Phe Ala Val Pro Ala Ala Arg Val His
145                 150                 155                 160

Arg Pro Ser Arg Cys Arg Tyr Arg Asp Leu Glu Val Arg Leu Cys Phe
                165                 170                 175

Glu Ser Phe Ser Asp Glu Leu Trp Lys Gly Arg Leu Leu Pro Leu Val
            180                 185                 190

Leu Leu Ala Glu Ala Leu Gly Phe Leu Leu Pro Leu Ala Ala Val Val
        195                 200                 205

Tyr Ser Ser Gly Arg Val Phe Trp Thr Leu Ala Arg Pro Asp Ala Thr
    210                 215                 220

Gln Ser Gln Arg Arg Arg Lys Thr Val Arg Leu Leu Leu Ala Asn Leu
225                 230                 235                 240

Val Ile Phe Leu Leu Cys Phe Val Pro Tyr Asn Ser Thr Leu Ala Val
                245                 250                 255

Tyr Gly Leu Leu Arg Ser Lys Leu Val Ala Ala Ser Val Pro Ala Arg
            260                 265                 270

Asp Arg Val Arg Gly Val Leu Met Val Met Val Leu Leu Ala Gly Ala
        275                 280                 285

Asn Cys Val Leu Asp Pro Leu Val Tyr Tyr Phe Ser Ala Glu Gly Phe
    290                 295                 300

Arg Asn Thr Leu Arg Gly Leu Gly Thr Pro His Arg Ala Arg Thr Ser
305                 310                 315                 320

Ala Thr Asn Gly Thr Arg Ala Ala Leu Ala Gln Ser Glu Arg Ser Ala
                325                 330                 335

Val Thr Thr Asp Ala Thr Arg Pro Asp Ala Ala Ser Gln Gly Leu Leu
            340                 345                 350

Arg Pro Ser Asp Ser His Ser Leu Ser Ser Phe Thr Gln Cys Pro Gln
        355                 360                 365

Asp Ser Ala Leu
    370
```

<210> SEQ ID NO 5

```
<211> LENGTH: 1107
<212> TYPE: DNA
<213> ORGANISM: Homo sapiens

<400> SEQUENCE: 5
atggccaact ccacagggct gaacgcctca gaagtcgcag gctcgttggg gttgatcctg      60
gcagctgtcg tggaggtggg ggcactgctg gcaacggcg cgctgctggt cgtggtgctg     120
cgcacgccgg gactgcgcga cgcgctctac ctggcgcacc tgtgcgtcgt ggacctgctg     180
gcggccgcct ccatcatgcc gctgggcctg ctggccgcac cgccgccggg ctgggccgc     240 gtgcgcctgg gccccgcgcc atgccgcgcc gctcgcttcc tctccgccgc tctgctgccg     300
gcctgcacgc tcggggtggc cgcacttggc ctggcacgct accgcctcat cgtgcacccg     360
ctgcggccag gctcgcggcc gccgcctgtg ctcgtgctca ccgccgtgtg ggccgcggcg     420
ggactgctgg gcgcgctctc cctgctcggc ccgccgcccg caccgccccc tgctcctgct     480
cgctgctcgg tcctggctgg gggcctcggg cccttccggc cgctctgggc cctgctggcc     540
ttcgcgctgc ccgccctcct gctgctcggc gcctacggcg catcttcgt ggtggcgcgt     600 cgcgctgccc tgaggccccc acggccggcg cgcgggtccc gactccgctc ggactctctg     660
gatagccgcc tttccatctt gccgccgctc cggcctcgcc tgcccggggg caaggcggcc     720
ctggccccag cgctggccgt gggccaattt gcagcctgct ggctgcctta ggctgcgcg     780 tgcctggcgc ccgcagcgcg ggccgcggaa gccgaagcgg ctgtcacctg ggtcgcctac     840
tcggccttcg cggctcaccc cttcctgtac gggctgctgc agcgcccgt gcgcttggca     900 ctgggccgcc tctctcgccg tgcactgcct ggacctgtgc gggcctgcac tccgcaagcc     960
tggcacccgc gggcactctt gcaatgcctc cagagacccc cagagggccc tgccgtaggc    1020
ccttctgagg ctccagaaca gacccccgag ttggcaggag ggcggagccc cgcataccag    1080
gggccacctg agagttctct ctcctga                                       1107

<210> SEQ ID NO 6
<211> LENGTH: 368
<212> TYPE: PRT
<213> ORGANISM: Homo sapiens

<400> SEQUENCE: 6

Met Ala Asn Ser Thr Gly Leu Asn Ala Ser Glu Val Ala Gly Ser Leu
 1               5                  10                  15

Gly Leu Ile Leu Ala Ala Val Val Glu Val Gly Ala Leu Leu Gly Asn
                20                  25                  30

Gly Ala Leu Leu Val Val Val Leu Arg Thr Pro Gly Leu Arg Asp Ala
            35                  40                  45

Leu Tyr Leu Ala His Leu Cys Val Val Asp Leu Ala Ala Ala Ser
        50                  55                  60

Ile Met Pro Leu Gly Leu Leu Ala Ala Pro Pro Gly Leu Gly Arg
 65                  70                  75                  80

Val Arg Leu Gly Pro Ala Pro Cys Arg Ala Ala Arg Phe Leu Ser Ala
                85                  90                  95

Ala Leu Leu Pro Ala Cys Thr Leu Gly Val Ala Ala Leu Gly Leu Ala
            100                 105                 110

Arg Tyr Arg Leu Ile Val His Pro Leu Arg Pro Gly Ser Arg Pro Pro
        115                 120                 125

Pro Val Leu Val Leu Thr Ala Val Trp Ala Ala Gly Leu Leu Gly
    130                 135                 140

Ala Leu Ser Leu Leu Gly Pro Pro Pro Ala Pro Pro Pro Ala Pro Ala
```

```
                145                 150                 155                 160
Arg Cys Ser Val Leu Ala Gly Gly Leu Gly Pro Phe Arg Pro Leu Trp
                    165                 170                 175

Ala Leu Leu Ala Phe Ala Leu Pro Ala Leu Leu Leu Gly Ala Tyr
                180                 185                 190

Gly Gly Ile Phe Val Val Ala Arg Ala Ala Leu Arg Pro Pro Arg
            195                 200                 205

Pro Ala Arg Gly Ser Arg Leu Arg Ser Asp Ser Leu Asp Ser Arg Leu
        210                 215                 220

Ser Ile Leu Pro Pro Leu Arg Pro Arg Leu Pro Gly Gly Lys Ala Ala
225                 230                 235                 240

Leu Ala Pro Ala Leu Ala Val Gly Gln Phe Ala Ala Cys Trp Leu Pro
                245                 250                 255

Tyr Gly Cys Ala Cys Leu Ala Pro Ala Ala Arg Ala Ala Glu Ala Glu
                260                 265                 270

Ala Ala Val Thr Trp Val Ala Tyr Ser Ala Phe Ala Ala His Pro Phe
            275                 280                 285

Leu Tyr Gly Leu Leu Gln Arg Pro Val Arg Leu Ala Leu Gly Arg Leu
        290                 295                 300

Ser Arg Arg Ala Leu Pro Gly Pro Val Arg Ala Cys Thr Pro Gln Ala
305                 310                 315                 320

Trp His Pro Arg Ala Leu Leu Gln Cys Leu Gln Arg Pro Glu Gly
                325                 330                 335

Pro Ala Val Gly Pro Ser Glu Ala Pro Glu Gln Thr Pro Glu Leu Ala
            340                 345                 350

Gly Gly Arg Ser Pro Ala Tyr Gln Gly Pro Pro Glu Ser Ser Leu Ser
        355                 360                 365

<210> SEQ ID NO 7
<211> LENGTH: 1008
<212> TYPE: DNA
<213> ORGANISM: Homo sapiens

<400> SEQUENCE: 7
atggaatcat ctttctcatt tggagtgatc cttgctgtcc tggcctccct catcattgct      60
actaacacac tagtggctgt ggctgtgctg ctgttgatcc acaagaatga tggtgtcagt     120
ctctgcttca ccttgaatct ggctgtggct gacaccttga ttggtgtggc catctctggc     180
ctactcacag accagctctc cagcccttct cggcccacac agaagaccct gtgcagcctg     240
cggatggcat ttgtcacttc ctccgcagct gcctctgtcc tcacggtcat gctgatcacc     300
tttgacaggt accttgccat caagcagccc ttccgctact tgaagatcat gagtgggttc     360
gtggccgggg cctgcattgc cgggctgtgg ttagtgtctt acctcattgg cttcctccca     420
ctcggaatcc ccatgttcca gcagactgcc tacaaagggc agtgcagctt ctttgctgta     480
tttcaccctc acttcgtgct gacccctctc ctgcgttggc tcttcccagc catgctcctc     540
tttgtcttct ctactgcga catgctcaag attgcctcca tgcacagcca gcagattcga     600
aagatggaac atgcaggagc catggctgga ggttatcgat ccccacggac tcccagcgac     660
ttcaaagctc tccgtactgt gtctgttctc attgggagct tgctctatc ctggacccc      720 ttccttatca ctggcattgt gcaggtggcc tgccaggagt gtcacctcta cctagtgctg     780
gaacggtacc tgtggctgct cggcgtgggc aactccctgc tcaacccact catctatgcc     840
tattggcaga aggaggtgcg actgcagctc taccacatgg ccctaggagt gaagaaggtg     900
ctcacctcat tcctcctctt tctctcggcc aggaattgtg gcccagagag gcccagggaa     960
```
agttcctgtc acatcgtcac tatctccagc tcagagtttg atggctaa               1008

<210> SEQ ID NO 8
<211> LENGTH: 335
<212> TYPE: PRT
<213> ORGANISM: Homo sapiens

<400> SEQUENCE: 8

Met Glu Ser Ser Phe Ser Phe Gly Val Ile Leu Ala Val Leu Ala Ser
1               5                   10                  15

Leu Ile Ile Ala Thr Asn Thr Leu Val Ala Val Ala Val Leu Leu Leu
            20                  25                  30

Ile His Lys Asn Asp Gly Val Ser Leu Cys Phe Thr Leu Asn Leu Ala
        35                  40                  45

Val Ala Asp Thr Leu Ile Gly Val Ala Ile Ser Gly Leu Leu Thr Asp
    50                  55                  60

Gln Leu Ser Ser Pro Ser Arg Pro Thr Gln Lys Thr Leu Cys Ser Leu
65                  70                  75                  80

Arg Met Ala Phe Val Thr Ser Ser Ala Ala Ser Val Leu Thr Val
                85                  90                  95

Met Leu Ile Thr Phe Asp Arg Tyr Leu Ala Ile Lys Gln Pro Phe Arg
            100                 105                 110

Tyr Leu Lys Ile Met Ser Gly Phe Val Ala Gly Ala Cys Ile Ala Gly
        115                 120                 125

Leu Trp Leu Val Ser Tyr Leu Ile Gly Phe Leu Pro Leu Gly Ile Pro
    130                 135                 140

Met Phe Gln Gln Thr Ala Tyr Lys Gly Gln Cys Ser Phe Phe Ala Val
145                 150                 155                 160

Phe His Pro His Phe Val Leu Thr Leu Ser Cys Val Gly Phe Phe Pro
                165                 170                 175

Ala Met Leu Leu Phe Val Phe Tyr Cys Asp Met Leu Lys Ile Ala
            180                 185                 190

Ser Met His Ser Gln Gln Ile Arg Lys Met Glu His Ala Gly Ala Met
        195                 200                 205

Ala Gly Gly Tyr Arg Ser Pro Arg Thr Pro Ser Asp Phe Lys Ala Leu
    210                 215                 220

Arg Thr Val Ser Val Leu Ile Gly Ser Phe Ala Leu Ser Trp Thr Pro
225                 230                 235                 240

Phe Leu Ile Thr Gly Ile Val Gln Val Ala Cys Gln Glu Cys His Leu
                245                 250                 255

Tyr Leu Val Leu Glu Arg Tyr Leu Trp Leu Leu Gly Val Gly Asn Ser
            260                 265                 270

Leu Leu Asn Pro Leu Ile Tyr Ala Tyr Trp Gln Lys Glu Val Arg Leu
        275                 280                 285

Gln Leu Tyr His Met Ala Leu Gly Val Lys Lys Val Leu Thr Ser Phe
    290                 295                 300

Leu Leu Phe Leu Ser Ala Arg Asn Cys Gly Pro Glu Arg Pro Arg Glu
305                 310                 315                 320

Ser Ser Cys His Ile Val Thr Ile Ser Ser Glu Phe Asp Gly
                325                 330                 335

<210> SEQ ID NO 9
<211> LENGTH: 1413
<212> TYPE: DNA
<213> ORGANISM: Homo sapiens

<400> SEQUENCE: 9

```
atggacacta ccatggaagc tgacctgggt gccactggcc acaggccccg cacagagctt    60
gatgatgagg actcctaccc ccaaggtggc tgggacacgg tcttcctggt ggccctgctg   120
ctccttgggc tgccagccaa tgggttgatg gcgtggctgg ccggctccca ggcccggcat   180
ggagctggca cgcgtctggc gctgctcctg ctcagcctgg ccctctctga cttcttgttc   240
ctggcagcag cggccttcca gatcctagag atccggcatg ggggacactg gccgctgggg   300
acagctgcct gccgcttcta ctacttccta tggggcgtgt cctactcctc cggcctcttc   360
ctgctggccg ccctcagcct cgaccgctgc tgctggcgc tgtgcccaca ctggtaccct   420
gggcaccgcc cagtccgcct gcccctctgg gtctgcgccg tgtctgggt gctggccaca   480
ctcttcagcg tgcctggct ggtcttcccc gaggctgccg tctggtggta cgacctggtc   540
atctgcctgg acttctggga cagcgaggag ctgtcgctga ggatgctgga ggtcctgggg   600
ggcttcctgc ctttcctcct gctgctcgtc tgccacgtgc tcacccaggc cacagcctgt   660
cgcacctgcc accgccaaca gcagcccgca gcctgccggg gcttcgcccg tgtggccagg   720
accattctgt cagcctatgt ggtcctgagg ctgccctacc agctggccca gctgctctac   780
ctggccttcc tgtgggacgt ctactctggc tacctgctct ggggaggccct ggtctactcc   840
gactacctga tcctactcaa cagctgcctc agcccctttcc tctgcctcat ggccagtgcc   900
gacctccgga ccctgctgcg ctccgtgctc tcgtccttcg cggcagctct ctgcgaggag   960
cggccgggca gcttcacgcc cactgagcca cagacccagc tagattctga gggtccaact  1020
ctgccagagc cgatggcaga ggcccagtca cagatggatc ctgtggccca gcctcaggtg  1080
aaccccacac tccagccacg atcggatccc acagctcagc acagctgaa ccctacggcc  1140
cagccacagt cggatccac agcccagcca cagctgaacc tcatggccca gccacagtca  1200
gattctgtgg cccagccaca ggcagacact aacgtccaga ccctgcacc tgctgccagt  1260
tctgtgccca gtccctgtga tgaagcttcc ccaaccccat cctcgcatcc taccccaggg  1320
gcccttgagg acccagccac acctcctgcc tctgaaggag aaagccccag cagcaccccg  1380
ccagaggcgg ccccgggcgc aggccccacg tga                               1413
```

<210> SEQ ID NO 10
<211> LENGTH: 468
<212> TYPE: PRT
<213> ORGANISM: Homo sapiens

<400> SEQUENCE: 10

```
Met Asp Thr Thr Met Glu Ala Asp Leu Gly Ala Thr Gly His Arg Pro
1               5                   10                  15

Arg Thr Glu Leu Asp Asp Glu Asp Ser Tyr Pro Gln Gly Gly Trp Asp
                20                  25                  30

Thr Val Phe Leu Val Ala Leu Leu Leu Gly Leu Pro Ala Asn Gly
            35                  40                  45

Leu Met Ala Trp Leu Ala Gly Ser Gln Ala Arg His Gly Ala Gly Thr
        50                  55                  60

Arg Leu Ala Leu Leu Leu Ser Leu Ala Leu Ser Asp Phe Leu Phe
65                  70                  75                  80

Leu Ala Ala Ala Phe Gln Ile Leu Glu Ile Arg His Gly His
                85                  90                  95

Trp Pro Leu Gly Thr Ala Ala Cys Arg Phe Tyr Tyr Phe Leu Trp Gly
                100                 105                 110

Val Ser Tyr Ser Ser Gly Leu Phe Leu Leu Ala Ala Leu Ser Leu Asp
```

```
                115                 120                 125
Arg Cys Leu Leu Ala Leu Cys Pro His Trp Tyr Pro Gly His Arg Pro
        130                 135                 140

Val Arg Leu Pro Leu Trp Val Cys Ala Gly Val Trp Val Leu Ala Thr
145                 150                 155                 160

Leu Phe Ser Val Pro Trp Leu Val Phe Pro Glu Ala Ala Val Trp Trp
                165                 170                 175

Tyr Asp Leu Val Ile Cys Leu Asp Phe Trp Asp Ser Glu Glu Leu Ser
            180                 185                 190

Leu Arg Met Leu Glu Val Leu Gly Gly Phe Leu Pro Phe Leu Leu Leu
        195                 200                 205

Leu Val Cys His Val Leu Thr Gln Ala Thr Arg Thr Cys His Arg Gln
    210                 215                 220

Gln Gln Pro Ala Ala Cys Arg Gly Phe Ala Arg Val Ala Arg Thr Ile
225                 230                 235                 240

Leu Ser Ala Tyr Val Val Leu Arg Leu Pro Tyr Gln Leu Ala Gln Leu
                245                 250                 255

Leu Tyr Leu Ala Phe Leu Trp Asp Val Tyr Ser Gly Tyr Leu Leu Trp
            260                 265                 270

Glu Ala Leu Val Tyr Ser Asp Tyr Leu Ile Leu Leu Asn Ser Cys Leu
        275                 280                 285

Ser Pro Phe Leu Cys Leu Met Ala Ser Ala Asp Leu Arg Thr Leu Leu
    290                 295                 300

Arg Ser Val Leu Ser Ser Phe Ala Ala Ala Leu Cys Glu Glu Arg Pro
305                 310                 315                 320

Gly Ser Phe Thr Pro Thr Glu Pro Gln Thr Gln Leu Asp Ser Glu Gly
                325                 330                 335

Pro Thr Leu Pro Glu Pro Met Ala Glu Ala Gln Ser Gln Met Asp Pro
            340                 345                 350

Val Ala Gln Pro Gln Val Asn Pro Thr Leu Gln Pro Arg Ser Asp Pro
        355                 360                 365

Thr Ala Gln Pro Gln Leu Asn Pro Thr Ala Gln Pro Gln Ser Asp Pro
    370                 375                 380

Thr Ala Gln Pro Gln Leu Asn Leu Met Ala Gln Pro Gln Ser Asp Ser
385                 390                 395                 400

Val Ala Gln Pro Gln Ala Asp Thr Asn Val Gln Thr Pro Ala Pro Ala
                405                 410                 415

Ala Ser Ser Val Pro Ser Pro Cys Asp Glu Ala Ser Thr Pro Ser
            420                 425                 430

Ser His Pro Thr Pro Gly Ala Leu Glu Asp Pro Ala Thr Pro Pro Ala
        435                 440                 445

Ser Glu Gly Glu Ser Pro Ser Ser Thr Pro Pro Glu Ala Ala Pro Gly
    450                 455                 460

Ala Gly Pro Thr
465

<210> SEQ ID NO 11
<211> LENGTH: 1248
<212> TYPE: DNA
<213> ORGANISM: Homo sapiens

<400> SEQUENCE: 11
atgtcaggga tggaaaaact tcagaatgct tcctggatct accagcagaa actagaagat      60
ccattccaga aacacctgaa cagcaccgag gagtatctgg ccttcctctg cggacctcgg     120
```

```
cgcagccact tcttcctccc cgtgtctgtg gtgtatgtgc caattttgt ggtgggggtc      180 attggcaatg tcctggtgtg cctggtgatt ctgcagcacc aggctatgaa acgcccacc      240 aactactacc tcttcagcct ggcggtctct gacctcctgg tcctgctcct tggaatgccc      300
ctggaggtct atgagatgtg gcgcaactac cctttcttgt tcgggcccgt gggctgctac      360
ttcaagacgg ccctctttga gaccgtgtgc ttcgcctcca tcctcagcat caccaccgtc      420
agcgtggagc gctacgtggc catcctacac ccgttccgcg ccaaactgca gagcacccgg      480
cgccgggccc tcaggatcct cggcatcgtc tggggcttct ccgtgctctt ctccctgccc      540
aacaccagca tccatggcat caagttccac tactttccca tgggtccct ggtcccaggt       600 tcggccacct gtacggtcat caagcccatg tggatctaca atttcatcat ccaggtcacc      660
tccttcctat tctacctcct ccccatgact gtcatcagtg tcctctacta cctcatggca      720
ctcagactaa agaaagacaa atctcttgag gcagatgaag ggaatgcaaa tattcaaaga      780
ccctgcagaa atcagtcaa caagatgctg tttgtcttgg tcttagtgtt tgctatctgt        840
tgggccccgt ccacattga ccgactcttc ttcagctttg tggaggagtg gagtgaatcc        900
ctggctgctg tgttcaacct cgtccatgtg gtgtcaggtg tcttcttcta cctgagctca      960
gctgtcaacc ccattatcta taacctactg tctcgccgct ccaggcagc attccagaat      1020 gtgatctctt ctttccacaa acagtggcac tcccagcatg acccacagtt gccacctgcc      1080
cagcggaaca tcttcctgac agaatgccac tttgtggagc tgaccgaaga tataggtccc      1140
caattcccat gtcagtcatc catgcacaac tctcacctcc aacagccct ctctagtgaa       1200 cagatgtcaa gaacaaacta tcaaagcttc cactttaaca aaacctga                   1248
```

<210> SEQ ID NO 12
<211> LENGTH: 415
<212> TYPE: PRT
<213> ORGANISM: Homo sapiens

<400> SEQUENCE: 12

```
Met Ser Gly Met Glu Lys Leu Gln Asn Ala Ser Trp Ile Tyr Gln Gln
1               5                   10                  15

Lys Leu Glu Asp Pro Phe Gln Lys His Leu Asn Ser Thr Glu Glu Tyr
            20                  25                  30

Leu Ala Phe Leu Cys Gly Pro Arg Arg Ser His Phe Phe Leu Pro Val
        35                  40                  45

Ser Val Val Tyr Val Pro Ile Phe Val Gly Val Ile Gly Asn Val
    50                  55                  60

Leu Val Cys Leu Val Ile Leu Gln His Gln Ala Met Lys Thr Pro Thr
65                  70                  75                  80

Asn Tyr Tyr Leu Phe Ser Leu Ala Val Ser Asp Leu Leu Val Leu Leu
                85                  90                  95

Leu Gly Met Pro Leu Glu Val Tyr Glu Met Trp Arg Asn Tyr Pro Phe
            100                 105                 110

Leu Phe Gly Pro Val Gly Cys Tyr Phe Lys Thr Ala Leu Phe Glu Thr
        115                 120                 125

Val Cys Phe Ala Ser Ile Leu Ser Ile Thr Thr Val Ser Val Glu Arg
    130                 135                 140

Tyr Val Ala Ile Leu His Pro Phe Arg Ala Lys Leu Gln Ser Thr Arg
145                 150                 155                 160

Arg Arg Ala Leu Arg Ile Leu Gly Ile Val Trp Gly Phe Ser Val Leu
                165                 170                 175

Phe Ser Leu Pro Asn Thr Ser Ile His Gly Ile Lys Phe His Tyr Phe
```

```
                   180              185              190
Pro Asn Gly Ser Leu Val Pro Gly Ser Ala Thr Cys Thr Val Ile Lys
                195              200              205

Pro Met Trp Ile Tyr Asn Phe Ile Ile Gln Val Thr Ser Phe Leu Phe
    210              215              220

Tyr Leu Leu Pro Met Thr Val Ile Ser Val Leu Tyr Tyr Leu Met Ala
225              230              235              240

Leu Arg Leu Lys Lys Asp Lys Ser Leu Glu Ala Asp Glu Gly Asn Ala
                245              250              255

Asn Ile Gln Arg Pro Cys Arg Lys Ser Val Asn Lys Met Leu Phe Val
            260              265              270

Leu Val Leu Val Phe Ala Ile Cys Trp Ala Pro Phe His Ile Asp Arg
            275              280              285

Leu Phe Phe Ser Phe Val Glu Glu Trp Ser Glu Ser Leu Ala Ala Val
            290              295              300

Phe Asn Leu Val His Val Val Ser Gly Val Phe Phe Tyr Leu Ser Ser
305              310              315              320

Ala Val Asn Pro Ile Ile Tyr Asn Leu Leu Ser Arg Arg Phe Gln Ala
                325              330              335

Ala Phe Gln Asn Val Ile Ser Ser Phe His Lys Gln Trp His Ser Gln
            340              345              350

His Asp Pro Gln Leu Pro Pro Ala Gln Arg Asn Ile Phe Leu Thr Glu
            355              360              365

Cys His Phe Val Glu Leu Thr Glu Asp Ile Gly Pro Gln Phe Pro Cys
    370              375              380

Gln Ser Ser Met His Asn Ser His Leu Pro Thr Ala Leu Ser Ser Glu
385              390              395              400

Gln Met Ser Arg Thr Asn Tyr Gln Ser Phe His Phe Asn Lys Thr
                405              410              415

<210> SEQ ID NO 13
<211> LENGTH: 1173
<212> TYPE: DNA
<213> ORGANISM: Homo sapiens

<400> SEQUENCE: 13
atgccagata ctaatagcac aatcaattta tcactaagca ctcgtgttac tttagcattt      60
tttatgtcct tagtagcttt tgctataatg ctaggaaatg ctttggtcat tttagctttt     120
gtggtggaca aaaaccttag acatcgaagt agttattttt tcttaacttt ggccatctct     180
gacttctttg tgggtgtgat ctccattcct ttgtacatcc ctcacacgct gttcgaatgg     240
gattttggaa aggaaatctg tgtatttttgg ctcactactg actatctgtt atgtacagca     300
tctgtatata acattgtcct catcagctat gatcgatacc tgtcagtctc aaatgctgtg     360
tcttatagaa ctcaacatac tggggtcttg aagattgtta ctctgatggt ggccgtttgg     420
gtgctggcct tcttagtgaa tgggccaatg attctagttt cagagtcttg aaggatgaa      480 ggtagtgaat gtgaacctgg attttttttcg aatggtaca tccttgccat cacatcattc     540
ttggaattcg tgatcccagt catcttagtc gcttatttca acatgaatat ttattggagc     600
ctgtggaagc gtgatcatct cagtaggtgc caaagccatc ctggactgac tgctgtctct     660
tccaacatct gtggacactc attcagaggt agactatctt caaggagatc tctttctgca     720
tcgacagaag ttcctgcatc ctttcattca gagagacaga ggagaaagag tagtctcatg     780
ttttcctcaa gaaccaagat gaatagcaat acaattgctt ccaaaatggg ttccttctcc     840
```

-continued

```
caatcagatt ctgtagctct tcaccaaagg gaacatgttg aactgcttag agccaggaga    900
ttagccaagt cactggccat tctcttaggg gttttgctg tttgctgggc tccatattct    960
ctgttcacaa ttgtcctttc attttattcc tcagcaacag gtcctaaatc agtttggtat   1020
agaattgcat tttggcttca gtggttcaat tcctttgtca atcctctttt gtatccattg   1080
tgtcacaagc gctttcaaaa ggctttcttg aaaatatttt gtataaaaaa gcaacctcta   1140
ccatcacaac acagtcggtc agtatcttct taa                               1173
```

<210> SEQ ID NO 14
<211> LENGTH: 390
<212> TYPE: PRT
<213> ORGANISM: Homo sapiens

<400> SEQUENCE: 14

```
Met Pro Asp Thr Asn Ser Thr Ile Asn Leu Ser Leu Ser Thr Arg Val
1               5                   10                  15

Thr Leu Ala Phe Phe Met Ser Leu Val Ala Phe Ala Ile Met Leu Gly
            20                  25                  30

Asn Ala Leu Val Ile Leu Ala Phe Val Val Asp Lys Asn Leu Arg His
        35                  40                  45

Arg Ser Ser Tyr Phe Phe Leu Asn Leu Ala Ile Ser Asp Phe Phe Val
    50                  55                  60

Gly Val Ile Ser Ile Pro Leu Tyr Ile Pro His Thr Leu Phe Glu Trp
65                  70                  75                  80

Asp Phe Gly Lys Glu Ile Cys Val Phe Trp Leu Thr Thr Asp Tyr Leu
                85                  90                  95

Leu Cys Thr Ala Ser Val Tyr Asn Ile Val Leu Ile Ser Tyr Asp Arg
            100                 105                 110

Tyr Leu Ser Val Ser Asn Ala Val Ser Tyr Arg Thr Gln His Thr Gly
        115                 120                 125

Val Leu Lys Ile Val Thr Leu Met Val Ala Val Trp Val Leu Ala Phe
    130                 135                 140

Leu Val Asn Gly Pro Met Ile Leu Val Ser Glu Ser Trp Lys Asp Glu
145                 150                 155                 160

Gly Ser Glu Cys Glu Pro Gly Phe Phe Ser Glu Trp Tyr Ile Leu Ala
                165                 170                 175

Ile Thr Ser Phe Leu Glu Phe Val Ile Pro Val Ile Leu Val Ala Tyr
            180                 185                 190

Phe Asn Met Asn Ile Tyr Trp Ser Leu Trp Lys Arg Asp His Leu Ser
        195                 200                 205

Arg Cys Gln Ser His Pro Gly Leu Thr Ala Val Ser Ser Asn Ile Cys
    210                 215                 220

Gly His Ser Phe Arg Gly Arg Leu Ser Ser Arg Arg Ser Leu Ser Ala
225                 230                 235                 240

Ser Thr Glu Val Pro Ala Ser Phe His Ser Arg Gln Arg Lys
                245                 250                 255

Ser Ser Leu Met Phe Ser Ser Arg Thr Lys Met Asn Ser Asn Thr Ile
        260                 265                 270

Ala Ser Lys Met Gly Ser Phe Ser Gln Ser Asp Ser Val Ala Leu His
    275                 280                 285

Gln Arg Glu His Val Glu Leu Leu Arg Ala Arg Arg Leu Ala Lys Ser
290                 295                 300

Leu Ala Ile Leu Leu Gly Val Phe Ala Val Cys Trp Ala Pro Tyr Ser
305                 310                 315                 320
```

```
Leu Phe Thr Ile Val Leu Ser Phe Tyr Ser Ser Ala Thr Gly Pro Lys
                325                 330                 335

Ser Val Trp Tyr Arg Ile Ala Phe Trp Leu Gln Trp Phe Asn Ser Phe
        340                 345                 350

Val Asn Pro Leu Leu Tyr Pro Leu Cys His Lys Arg Phe Gln Lys Ala
            355                 360                 365

Phe Leu Lys Ile Phe Cys Ile Lys Lys Gln Pro Leu Pro Ser Gln His
        370                 375                 380

Ser Arg Ser Val Ser Ser
385                 390
```

<210> SEQ ID NO 15
<211> LENGTH: 30
<212> TYPE: DNA
<213> ORGANISM: Artificial Sequence
<220> FEATURE:
<223> OTHER INFORMATION: Novel Sequence

<400> SEQUENCE: 15
ggaaagctta acgatcccca ggagcaacat                                          30

<210> SEQ ID NO 16
<211> LENGTH: 31
<212> TYPE: DNA
<213> ORGANISM: Artificial Sequence
<220> FEATURE:
<223> OTHER INFORMATION: Novel Sequence

<400> SEQUENCE: 16
ctgggatcct acgagagcat ttttcacaca g                                        31

<210> SEQ ID NO 17
<211> LENGTH: 1128
<212> TYPE: DNA
<213> ORGANISM: Homo sapiens

<400> SEQUENCE: 17
atggcgaacg cgagcgagcc gggtggcagc ggcggcggcg aggcggccgc cctgggcctc          60
aagctggcca cgctcagcct gctgctgtgc gtgagcctag cgggcaacgt gctgttcgcg         120
ctgctgatcg tgcgggagcg cagcctgcac cgcgccccgt actacctgct gctcgacctg         180
tgcctggccg acgggctgcg cgcgctcgcc tgcctcccgg ccgtcatgct ggcggcgcgg         240
cgtgcggcgg ccgcggcggg ggcgccgccg gcgcgctgg gctgcaagct gctcgccttc          300
ctggccgcgc tcttctgctt ccacgccgcc ttcctgctgc tgggcgtggg cgtcacccgc         360
tacctggcca tcgcgcacca ccgcttctat gcagagcgcc tggccggctg gccgtgcgcc         420
gccatgctgg tgtgcgccgc ctgggcgctg gcgctggccg cggccttccc gccagtgctg         480
gacggcggtg cgacgacga ggacgcgccg tgcgccctgg agcagcggcc cgacggcgcc          540 cccgcgcgc tgggcttcct gctgctgctg ccgtggtgg tgggcgccac gcacctcgtc          600
tacctccgcc tgctcttctt catccacgac cgccgcaaga tgcggcccgc gcgcctggtg         660
cccgccgtca gccacgactg gaccttccac ggcccgggcg ccaccggcca ggcggccgcc         720
aactggacgg cgggcttcgg ccgcggggcc acgccgcccg cgcttgtggg catccggccc         780
gcagggccgg gccgcggcgc gcgccgcctc tcgtgctgtg aagaattcaa gacggagaag         840
aggctgtgca agatgttcta cgccgtcacg ctgctcttcc tgctcctctg ggggccctac         900
gtcgtggcca gctacctgcg ggtcctggtg cggcccggcg ccgtccccca ggcctacctg         960
acggcctccg tgtggctgac cttcgcgcag gccggcatca accccgtcgt gtgcttcctc        1020

```
ttcaacaggg agctgaggga ctgcttcagg gcccagttcc cctgctgcca gagccccggg   1080
accacccagg cgacccatcc ctgcgacctg aaaggcattg gtttatga               1128
```

<210> SEQ ID NO 18
<211> LENGTH: 375
<212> TYPE: PRT
<213> ORGANISM: Homo sapiens

<400> SEQUENCE: 18

```
Met Ala Asn Ala Ser Glu Pro Gly Gly Ser Gly Gly Gly Glu Ala Ala
1               5                   10                  15

Ala Leu Gly Leu Lys Leu Ala Thr Leu Ser Leu Leu Leu Cys Val Ser
            20                  25                  30

Leu Ala Gly Asn Val Leu Phe Ala Leu Leu Ile Val Arg Glu Arg Ser
        35                  40                  45

Leu His Arg Ala Pro Tyr Tyr Leu Leu Leu Asp Leu Cys Leu Ala Asp
    50                  55                  60

Gly Leu Arg Ala Leu Ala Cys Leu Pro Ala Val Met Leu Ala Ala Arg
65                  70                  75                  80

Arg Ala Ala Ala Ala Gly Ala Pro Gly Ala Leu Gly Cys Lys
                85                  90                  95

Leu Leu Ala Phe Leu Ala Ala Leu Phe Cys Phe His Ala Ala Phe Leu
            100                 105                 110

Leu Leu Gly Val Gly Val Thr Arg Tyr Leu Ala Ile Ala His His Arg
        115                 120                 125

Phe Tyr Ala Glu Arg Leu Ala Gly Trp Pro Cys Ala Ala Met Leu Val
    130                 135                 140

Cys Ala Ala Trp Ala Leu Ala Leu Ala Ala Ala Phe Pro Pro Val Leu
145                 150                 155                 160

Asp Gly Gly Gly Asp Asp Glu Asp Ala Pro Cys Ala Leu Glu Gln Arg
                165                 170                 175

Pro Asp Gly Ala Pro Gly Ala Leu Gly Phe Leu Leu Leu Leu Ala Val
            180                 185                 190

Val Val Gly Ala Thr His Leu Val Tyr Leu Arg Leu Leu Phe Phe Ile
        195                 200                 205

His Asp Arg Arg Lys Met Arg Pro Ala Arg Leu Val Pro Ala Val Ser
    210                 215                 220

His Asp Trp Thr Phe His Gly Pro Gly Ala Thr Gly Gln Ala Ala Ala
225                 230                 235                 240

Asn Trp Thr Ala Gly Phe Gly Arg Gly Pro Thr Pro Ala Leu Val
                245                 250                 255

Gly Ile Arg Pro Ala Gly Pro Gly Arg Gly Ala Arg Arg Leu Leu Val
            260                 265                 270

Leu Glu Glu Phe Lys Thr Glu Lys Arg Leu Cys Lys Met Phe Tyr Ala
        275                 280                 285

Val Thr Leu Leu Phe Leu Leu Leu Trp Gly Pro Tyr Val Val Ala Ser
    290                 295                 300

Tyr Leu Arg Val Leu Val Arg Pro Gly Ala Val Pro Gln Ala Tyr Leu
305                 310                 315                 320

Thr Ala Ser Val Trp Leu Thr Phe Ala Gln Ala Gly Ile Asn Pro Val
                325                 330                 335

Val Cys Phe Leu Phe Asn Arg Glu Leu Arg Asp Cys Phe Arg Ala Gln
            340                 345                 350

Phe Pro Cys Cys Gln Ser Pro Arg Thr Thr Gln Ala Thr His Pro Cys
```

```
                    355                 360                 365

Asp Leu Lys Gly Ile Gly Leu
    370                 375

<210> SEQ ID NO 19
<211> LENGTH: 1002
<212> TYPE: DNA
<213> ORGANISM: Homo sapiens

<400> SEQUENCE: 19
atgaacacca cagtgatgca aggcttcaac agatctgagc ggtgccccag agacactcgg      60
atagtacagc tggtattccc agccctctac acagtggttt tcttgaccgg catcctgctg     120
aatactttgg ctctgtgggt gtttgttcac atccccagct cctccacctt catcatctac     180
ctcaaaaaca cctttggtgg cgacttgata atgacactca tgcttccttt caaaatcctc     240
tctgactcac acctggcacc ctggcagctc agagcttttg tgtgtcgttt ttcttcggtg     300
atattttatg agaccatgta tgtgggcatc gtgctgttag ggctcatagc ctttgacaga     360
ttcctcaaga tcatcagacc tttgagaaat atttttctaa aaaaacctgt ttttgcaaaa     420
acggtctcaa tcttcatctg ttcttttttg ttcttcatct ccctgccaaa tacgatcttg     480
agcaacaagg aagcaacacc atcgtctgtg aaaaagtgtg cttccttaaa ggggcctctg     540
gggctgaaat ggcatcaaat ggtaaataac atatgccagt ttattttctg gactgttttt     600
atcctaatgc ttgtgtttta tgtggttatt gcaaaaaaag tatatgattc ttatagaaag     660
tccaaaagta aggacagaaa aaacaacaaa agctggaag gcaaagtatt tgttgtcgtg     720
gctgtcttct ttgtgtgttt tgctccattt catttttgcca gagttccata tactcacagt     780
caaaccaaca ataagactga ctgtagactg caaaatcaac tgtttattgc taaagaaaca     840
actctctttt tggcagcaac taacatttgt atggatccct aatatacat attcttatgt      900 aaaaaattca cagaaaagct accatgtatg caagggagaa agaccacagc atcaagccaa     960
gaaaatcata gcagtcagac agacaacata accttaggct ga                      1002

<210> SEQ ID NO 20
<211> LENGTH: 333
<212> TYPE: PRT
<213> ORGANISM: Homo sapiens

<400> SEQUENCE: 20

Met Asn Thr Thr Val Met Gln Gly Phe Asn Arg Ser Glu Arg Cys Pro
1               5                   10                  15

Arg Asp Thr Arg Ile Val Gln Leu Val Phe Pro Ala Leu Tyr Thr Val
            20                  25                  30

Val Phe Leu Thr Gly Ile Leu Leu Asn Thr Leu Ala Leu Trp Val Phe
        35                  40                  45

Val His Ile Pro Ser Ser Ser Thr Phe Ile Ile Tyr Leu Lys Asn Thr
    50                  55                  60

Leu Val Ala Asp Leu Ile Met Thr Leu Met Leu Pro Phe Lys Ile Leu
65                  70                  75                  80

Ser Asp Ser His Leu Ala Pro Trp Gln Leu Arg Ala Phe Val Cys Arg
                85                  90                  95

Phe Ser Ser Val Ile Phe Tyr Glu Thr Met Tyr Val Gly Ile Val Leu
            100                 105                 110

Leu Gly Leu Ile Ala Phe Asp Arg Phe Leu Lys Ile Ile Arg Pro Leu
        115                 120                 125

Arg Asn Ile Phe Leu Lys Lys Pro Val Phe Ala Lys Thr Val Ser Ile
```

```
              130                 135                 140
Phe Ile Trp Phe Phe Leu Phe Phe Ile Ser Leu Pro Asn Thr Ile Leu
145                 150                 155                 160

Ser Asn Lys Glu Ala Thr Pro Ser Ser Val Lys Lys Cys Ala Ser Leu
                165                 170                 175

Lys Gly Pro Leu Gly Leu Lys Trp His Gln Met Val Asn Asn Ile Cys
            180                 185                 190

Gln Phe Ile Phe Trp Thr Val Phe Ile Leu Met Leu Val Phe Tyr Val
        195                 200                 205

Val Ile Ala Lys Lys Val Tyr Asp Ser Tyr Arg Lys Ser Lys Ser Lys
    210                 215                 220

Asp Arg Lys Asn Asn Lys Lys Leu Glu Gly Lys Val Phe Val Val Val
225                 230                 235                 240

Ala Val Phe Phe Val Cys Phe Ala Pro Phe His Phe Ala Arg Val Pro
                245                 250                 255

Tyr Thr His Ser Gln Thr Asn Asn Lys Thr Asp Cys Arg Leu Gln Asn
            260                 265                 270

Gln Leu Phe Ile Ala Lys Glu Thr Thr Leu Phe Leu Ala Ala Thr Asn
        275                 280                 285

Ile Cys Met Asp Pro Leu Ile Tyr Ile Phe Leu Cys Lys Lys Phe Thr
    290                 295                 300

Glu Lys Leu Pro Cys Met Gln Gly Arg Lys Thr Thr Ala Ser Ser Gln
305                 310                 315                 320

Glu Asn His Ser Ser Gln Thr Asp Asn Ile Thr Leu Gly
                325                 330

<210> SEQ ID NO 21
<211> LENGTH: 1122
<212> TYPE: DNA
<213> ORGANISM: Homo sapiens

<400> SEQUENCE: 21
atggccaaca ctaccggaga gcctgaggag gtgagcggcg ctctgtcccc accgtccgca      60
tcagcttatg tgaagctggt actgctggga ctgattatgt gcgtgagcct ggcgggtaac     120
gccatcttgt ccctgctggt gctcaaggag cgtgccctgc acaaggctcc ttactacttc     180
ctgctggacc tgtgcctggc cgatggcata cgctctgccg tctgcttccc ctttgtgctg     240
gcttctgtgc ccacggctc ttcatggacc ttcagtgcac tcagctgcaa gattgtggcc     300 tttatgccg tgtctttttg cttccatgcg gccttcatgc tgttctgcat cagcgtcacc     360
cgctacatgg ccatcgccca ccaccgcttc tacgccaagc gcatgacact ctggacatgc     420
gcggctgtca tctgcatggc ctggaccctg tctgtggcca tggccttccc acctgtcttt     480
gacgtgggca cctacaagtt tattcgggag gaggaccagt gcatctttga gcatcgctac     540
ttcaaggcca atgacacgct gggcttcatg cttatgttgg ctgtgctcat ggcagctacc     600
catgctgtct acggcaagct gctcctcttc gagtatcgtc accgcaagat gaagccagtg     660
cagatggtgc cagccatcag ccagaactgg acattccatg gtcccgggc caccggccag     720 gctgctgcca actggatcgc cggctttggc cgtgggccca tgccaccaac cctgctgggt     780
atccggcaga tgggcatgc agccagccgg cggctactgg gcatggacga ggtcaagggt     840
gaaaagcagc tgggccgcat gttctacgcg atcacactgc tctttctgct cctctggtca     900
ccctacatcg tggcctgcta ctggcgagtg tttgtgaaag cctgtgctgt gcccaccgc      960 tacctggcca ctgctgtttg gatgagcttc gcccaggctg ccgtcaaccc aattgtctgc    1020
```

```
ttcctgctca acaaggacct caagaagtgc ctgaccactc acgcccctg  ctggggcaca    1080 ggaggtgccc cggctcccag agaaccctac tgtgtcatgt ga                       1122
```

<210> SEQ ID NO 22
<211> LENGTH: 373
<212> TYPE: PRT
<213> ORGANISM: Homo sapiens

<400> SEQUENCE: 22

```
Met Ala Asn Thr Thr Gly Glu Pro Glu Val Ser Gly Ala Leu Ser
1               5                   10                  15

Pro Pro Ser Ala Ser Ala Tyr Val Lys Leu Val Leu Gly Leu Ile
                20                  25                  30

Met Cys Val Ser Leu Ala Gly Asn Ala Ile Leu Ser Leu Val Leu
            35                  40                  45

Lys Glu Arg Ala Leu His Lys Ala Pro Tyr Tyr Phe Leu Leu Asp Leu
        50                  55                  60

Cys Leu Ala Asp Gly Ile Arg Ser Ala Val Cys Phe Pro Phe Val Leu
65                  70                  75                  80

Ala Ser Val Arg His Gly Ser Ser Trp Thr Phe Ser Ala Leu Ser Cys
                85                  90                  95

Lys Ile Val Ala Phe Met Ala Val Leu Phe Cys Phe His Ala Ala Phe
            100                 105                 110

Met Leu Phe Cys Ile Ser Val Thr Arg Tyr Met Ala Ile Ala His His
        115                 120                 125

Arg Phe Tyr Ala Lys Arg Met Thr Leu Trp Thr Cys Ala Ala Val Ile
    130                 135                 140

Cys Met Ala Trp Thr Leu Ser Val Ala Met Ala Phe Pro Pro Val Phe
145                 150                 155                 160

Asp Val Gly Thr Tyr Lys Phe Ile Arg Glu Glu Asp Gln Cys Ile Phe
                165                 170                 175

Glu His Arg Tyr Phe Lys Ala Asn Asp Thr Leu Gly Phe Met Leu Met
            180                 185                 190

Leu Ala Val Leu Met Ala Ala Thr His Ala Val Tyr Gly Lys Leu Leu
        195                 200                 205

Leu Phe Glu Tyr Arg His Arg Lys Met Lys Pro Val Gln Met Val Pro
    210                 215                 220

Ala Ile Ser Gln Asn Trp Thr Phe His Gly Pro Gly Ala Thr Gly Gln
225                 230                 235                 240

Ala Ala Ala Asn Trp Ile Ala Gly Phe Gly Arg Gly Pro Met Pro Pro
                245                 250                 255

Thr Leu Leu Gly Ile Arg Gln Asn Gly His Ala Ala Ser Arg Arg Leu
            260                 265                 270

Leu Gly Met Asp Glu Val Lys Gly Glu Lys Gln Leu Gly Arg Met Phe
        275                 280                 285

Tyr Ala Ile Thr Leu Leu Phe Leu Leu Leu Trp Ser Pro Tyr Ile Val
    290                 295                 300

Ala Cys Tyr Trp Arg Val Phe Val Lys Ala Cys Ala Val Pro His Arg
305                 310                 315                 320

Tyr Leu Ala Thr Ala Val Trp Met Ser Phe Ala Gln Ala Ala Val Asn
                325                 330                 335

Pro Ile Val Cys Phe Leu Leu Asn Lys Asp Leu Lys Lys Cys Leu Thr
            340                 345                 350

Thr His Ala Pro Cys Trp Gly Thr Gly Gly Ala Pro Ala Pro Arg Glu
        355                 360                 365
```

Pro Tyr Cys Val Met
    370

<210> SEQ ID NO 23
<211> LENGTH: 1053
<212> TYPE: DNA
<213> ORGANISM: Homo sapiens

<400> SEQUENCE: 23

```
atggctttgg aacagaacca gtcaacagat tattattatg aggaaaatga atgaatggc      60
acttatgact acagtcaata tgaattgatc tgtatcaaag aagatgtcag agaatttgca    120
aaagttttcc tccctgtatt cctcacaata gctttcgtca ttggacttgc aggcaattcc    180
atggtagtgg caattatgc ctattacaag aaacagagaa ccaaaacaga tgtgtacatc     240
ctgaatttgg ctgtagcaga tttactcctt ctattcactc tgccttttg ggctgttaat     300
gcagttcatg ggtgggtttt agggaaaata atgtgcaaaa taacttcagc cttgtacaca    360
ctaaactttg tctctggaat gcagtttctg gcttgcatca gcatagacag atatgtggca    420
gtaactaatg tccccagcca atcaggagtg gaaaaccat gctggatcat ctgtttctgt      480
gtctggatgg ctgccatctt gctgagcata ccccagctgg ttttttatac agtaaatgac    540
aatgctaggt gcattcccat tttcccccgc tacctaggaa catcaatgaa agcattgatt    600
caaatgctag agatctgcat tggatttgta gtacccttc ttattatggg ggtgtgctac     660
tttatcacgg caaggacact catgaagatg ccaaacatta aaatatctcg accccctaaaa   720
gttctgctca gtcgttat agttttcatt gtcactcaac tgccttataa cattgtcaag       780
ttctgccgag ccatagacat catctactcc ctgatcacca gctgcaacat gagcaaacgc    840
atggacatcg ccatccaagt cacagaaagc attgcactct tcacagctg cctcaaccca     900
atcctttatg ttttatggg agcatctttc aaaaactacg ttatgaaagt ggccaagaaa    960
tatgggtcct ggagaagaca gagacaaagt gtggaggagt tcctttga ttctgagggt    1020
cctacagagc caaccagtac ttttagcatt taa                                1053
```

<210> SEQ ID NO 24
<211> LENGTH: 350
<212> TYPE: PRT
<213> ORGANISM: Homo sapiens

<400> SEQUENCE: 24

```
Met Ala Leu Glu Gln Asn Gln Ser Thr Asp Tyr Tyr Tyr Glu Asn
1               5                   10                  15

Glu Met Asn Gly Thr Tyr Asp Tyr Ser Gln Tyr Glu Leu Ile Cys Ile
            20                  25                  30

Lys Glu Asp Val Arg Glu Phe Ala Lys Val Phe Leu Pro Val Phe Leu
        35                  40                  45

Thr Ile Ala Phe Val Ile Gly Leu Ala Gly Asn Ser Met Val Val Ala
    50                  55                  60

Ile Tyr Ala Tyr Tyr Lys Lys Gln Arg Thr Lys Thr Asp Val Tyr Ile
65                  70                  75                  80

Leu Asn Leu Ala Val Ala Asp Leu Leu Leu Phe Thr Leu Pro Phe
                85                  90                  95

Trp Ala Val Asn Ala Val His Gly Trp Val Leu Gly Lys Ile Met Cys
            100                 105                 110

Lys Ile Thr Ser Ala Leu Tyr Thr Leu Asn Phe Val Ser Gly Met Gln
        115                 120                 125
```

```
Phe Leu Ala Cys Ile Ser Ile Asp Arg Tyr Val Ala Val Thr Asn Val
            130                 135                 140

Pro Ser Gln Ser Gly Val Gly Lys Pro Cys Trp Ile Ile Cys Phe Cys
145                 150                 155                 160

Val Trp Met Ala Ala Ile Leu Leu Ser Ile Pro Gln Leu Val Phe Tyr
                165                 170                 175

Thr Val Asn Asp Asn Ala Arg Cys Ile Pro Ile Phe Pro Arg Tyr Leu
            180                 185                 190

Gly Thr Ser Met Lys Ala Leu Ile Gln Met Leu Glu Ile Cys Ile Gly
                195                 200                 205

Phe Val Val Pro Phe Leu Ile Met Gly Val Cys Tyr Phe Ile Thr Ala
            210                 215                 220

Arg Thr Leu Met Lys Met Pro Asn Ile Lys Ile Ser Arg Pro Leu Lys
225                 230                 235                 240

Val Leu Leu Thr Val Val Ile Val Phe Ile Val Thr Gln Leu Pro Tyr
                245                 250                 255

Asn Ile Val Lys Phe Cys Arg Ala Ile Asp Ile Ile Tyr Ser Leu Ile
            260                 265                 270

Thr Ser Cys Asn Met Ser Lys Arg Met Asp Ile Ala Ile Gln Val Thr
275                 280                 285

Glu Ser Ile Ala Leu Phe His Ser Cys Leu Asn Pro Ile Leu Tyr Val
290                 295                 300

Phe Met Gly Ala Ser Phe Lys Asn Tyr Val Met Lys Val Ala Lys Lys
305                 310                 315                 320

Tyr Gly Ser Trp Arg Arg Gln Arg Gln Ser Val Glu Glu Phe Pro Phe
                325                 330                 335

Asp Ser Glu Gly Pro Thr Glu Pro Thr Ser Thr Phe Ser Ile
            340                 345                 350

<210> SEQ ID NO 25
<211> LENGTH: 1116
<212> TYPE: DNA
<213> ORGANISM: Homo sapiens

<400> SEQUENCE: 25
atgccaggaa acgccacccc agtgaccacc actgccccgt gggcctccct gggcctctcc      60
gccaagacct gcaacaacgt gtccttcgaa gagagcagga tagtcctggt cgtggtgtac     120
agcgcggtgt gcacgctggg ggtgccggcc aactgcctga ctgcgtggct ggcgctgctg     180
caggtactgc agggcaacgt gctggccgtc tacctgctct gcctggcact ctgcgaactg     240
ctgtacacag gcacgctgcc actctgggtc atctatatcc gcaaccagca ccgctggacc     300
ctaggcctgc tggcctcgaa ggtgaccgcc tacatcttct tctgcaacat ctacgtcagc     360
atcctcttcc tgtgctgcat ctcctgcgac cgcttcgtgg ccgtggtgta cgcgctggag     420
agtcggggcc gccgccgccg gaggaccgcc atcctcatct ccgcctgcat cttcatcctc     480
gtcgggatcg ttcactaccc ggtgttccag acggaagaca aggagacctg ctttgacatg     540
ctgcagatgg acagcaggat tgccgggtac tactacgcca ggttcaccgt ggctttgcc      600 atccctctct ccatcatcgc cttcaccaac caccggattt tcaggagcat caagcagagc     660
atgggcttaa gcgctgccca gaaggccaag gtgaagcact cggccatcgc ggtggttgtc     720
atcttcctag tctgcttcgc cccgtaccac ctggttctcc tcgtcaaagc cgctgccttt     780
tcctactaca ggagagacag gaacgccatg tgcggcttgg aggaaaggct gtacacagcc     840
tctgtggtgt ttctgtgcct gtccacggtg aacggcgtgg ctgaccccat tatctacgtg     900
```

-continued

```
ctggccacgg accattcccg ccaagaagtg tccagaatcc ataaggggtg gaaagagtgg      960
tccatgaaga cagacgtcac caggctcacc cacagcaggg acaccgagga gctgcagtcg     1020
cccgtggccc ttgcagacca ctacaccttc tccaggcccg tgcacccacc agggtcacca     1080
tgccctgcaa agaggctgat tgaggagtcc tgctga                               1116
```

<210> SEQ ID NO 26
<211> LENGTH: 371
<212> TYPE: PRT
<213> ORGANISM: Homo sapiens

<400> SEQUENCE: 26

```
Met Pro Gly Asn Ala Thr Pro Val Thr Thr Thr Ala Pro Trp Ala Ser
1               5                   10                  15

Leu Gly Leu Ser Ala Lys Thr Cys Asn Asn Val Ser Phe Glu Glu Ser
            20                  25                  30

Arg Ile Val Leu Val Val Val Tyr Ser Ala Val Cys Thr Leu Gly Val
        35                  40                  45

Pro Ala Asn Cys Leu Thr Ala Trp Leu Ala Leu Leu Gln Val Leu Gln
    50                  55                  60

Gly Asn Val Leu Ala Val Tyr Leu Leu Cys Leu Ala Leu Cys Glu Leu
65                  70                  75                  80

Leu Tyr Thr Gly Thr Leu Pro Leu Trp Val Ile Tyr Ile Arg Asn Gln
                85                  90                  95

His Arg Trp Thr Leu Gly Leu Leu Ala Ser Lys Val Thr Ala Tyr Ile
            100                 105                 110

Phe Phe Cys Asn Ile Tyr Val Ser Ile Leu Phe Leu Cys Cys Ile Ser
        115                 120                 125

Cys Asp Arg Phe Val Ala Val Tyr Ala Leu Glu Ser Arg Gly Arg
    130                 135                 140

Arg Arg Arg Arg Thr Ala Ile Leu Ile Ser Ala Cys Ile Phe Ile Leu
145                 150                 155                 160

Val Gly Ile Val His Tyr Pro Val Phe Gln Thr Glu Asp Lys Glu Thr
                165                 170                 175

Cys Phe Asp Met Leu Gln Met Asp Ser Arg Ile Ala Gly Tyr Tyr Tyr
            180                 185                 190

Ala Arg Phe Thr Val Gly Phe Ala Ile Pro Leu Ser Ile Ile Ala Phe
        195                 200                 205

Thr Asn His Arg Ile Phe Arg Ser Ile Lys Gln Ser Met Gly Leu Ser
    210                 215                 220

Ala Ala Gln Lys Ala Lys Val Lys His Ser Ala Ile Ala Val Val Val
225                 230                 235                 240

Ile Phe Leu Val Cys Phe Ala Pro Tyr His Leu Val Leu Leu Val Lys
                245                 250                 255

Ala Ala Ala Phe Ser Tyr Tyr Arg Gly Asp Arg Asn Ala Met Cys Gly
            260                 265                 270

Leu Glu Glu Arg Leu Tyr Thr Ala Ser Val Val Phe Leu Cys Leu Ser
        275                 280                 285

Thr Val Asn Gly Val Ala Asp Pro Ile Ile Tyr Val Leu Ala Thr Asp
    290                 295                 300

His Ser Arg Gln Glu Val Ser Arg Ile His Lys Gly Trp Lys Glu Trp
305                 310                 315                 320

Ser Met Lys Thr Asp Val Thr Arg Leu Thr His Ser Arg Asp Thr Glu
                325                 330                 335

Glu Leu Gln Ser Pro Val Ala Leu Ala Asp His Tyr Thr Phe Ser Arg
```

```
                    340                 345                 350
Pro Val His Pro Pro Gly Ser Pro Cys Pro Ala Lys Arg Leu Ile Glu
        355                 360                 365

Glu Ser Cys
        370
```

<210> SEQ ID NO 27
<211> LENGTH: 1113
<212> TYPE: DNA
<213> ORGANISM: Homo sapiens

<400> SEQUENCE: 27

```
atggcgaact atagccatgc agctgacaac attttgcaaa atctctcgcc tctaacagcc    60
tttctgaaac tgacttcctt gggtttcata ataggagtca gcgtggtggg caacctcctg   120
atctccattt tgctagtgaa agataagacc ttgcatagag caccttacta cttcctgttg   180
gatctttgct gttcagatat cctcagatct gcaatttgtt tcccatttgt gttcaactct   240
gtcaaaaatg gctctacctg gacttatggg actctgactt gcaaagtgat tgcctttctg   300
ggggttttgt cctgtttcca cactgctttc atgctcttct gcatcagtgt caccagatac   360
ttagctatcg cccatcaccg cttctataca aagaggctga ccttttggac gtgtctggct   420
gtgatctgta tggtgtggac tctgtctgtg ccatggcatt tcccccggt tttagacgtg   480
ggcacttact cattcattag ggaggaagat caatgcacct tccaacaccg ctccttcagg   540
gctaatgatt ccttaggatt tatgctgctt cttgctctca tcctcctagc cacacagctt   600
gtctacctca agctgatatt tttcgtccac gatcgaagaa aaatgaagcc agtccagttt   660
gtagcagcag tcagccagaa ctggactttt catggtcctg agccagtggc caggcagct   720
gccaattggc tagcaggatt tggaagggt cccacaccac ccaccttgct gggcatcagg   780
caaaatgcaa acaccacagg cagaagaagg ctattggtct tagacgagtt caaaatggag   840
aaaagaatca gcagaatgtt ctatataatg acttttctgt ttctaacctt gtggggcccc   900
tacctggtgg cctgttattg agagtttt gcaagagggc ctgtagtacc aggggatt    960
ctaacagctg ctgtctggat gagttttgcc caagcaggaa tcaatccttt tgtctgcatt  1020
ttctcaaaca gggagctgag gcgctgtttc agcacaaccc ttctttactg cagaaaatcc  1080
aggttaccaa gggaacctta ctgtgttata tga                               1113
```

<210> SEQ ID NO 28
<211> LENGTH: 370
<212> TYPE: PRT
<213> ORGANISM: Homo sapiens

<400> SEQUENCE: 28

```
Met Ala Asn Tyr Ser His Ala Ala Asp Asn Ile Leu Gln Asn Leu Ser
1               5                   10                  15

Pro Leu Thr Ala Phe Leu Lys Leu Thr Ser Leu Gly Phe Ile Ile Gly
            20                  25                  30

Val Ser Val Val Gly Asn Leu Leu Ile Ser Ile Leu Leu Val Lys Asp
        35                  40                  45

Lys Thr Leu His Arg Ala Pro Tyr Tyr Phe Leu Leu Asp Leu Cys Cys
    50                  55                  60

Ser Asp Ile Leu Arg Ser Ala Ile Cys Phe Pro Phe Val Phe Asn Ser
65                  70                  75                  80

Val Lys Asn Gly Ser Thr Trp Thr Tyr Gly Thr Leu Thr Cys Lys Val
                85                  90                  95
```

```
Ile Ala Phe Leu Gly Val Leu Ser Cys Phe His Thr Ala Phe Met Leu
            100                 105                 110

Phe Cys Ile Ser Val Thr Arg Tyr Leu Ala Ile Ala His Arg Phe
        115                 120                 125

Tyr Thr Lys Arg Leu Thr Phe Trp Thr Cys Leu Ala Val Ile Cys Met
130                 135                 140

Val Trp Thr Leu Ser Val Ala Met Ala Phe Pro Pro Val Leu Asp Val
145                 150                 155                 160

Gly Thr Tyr Ser Phe Ile Arg Glu Glu Asp Gln Cys Thr Phe Gln His
                165                 170                 175

Arg Ser Phe Arg Ala Asn Asp Ser Leu Gly Phe Met Leu Leu Leu Ala
            180                 185                 190

Leu Ile Leu Leu Ala Thr Gln Leu Val Tyr Leu Lys Leu Ile Phe Phe
        195                 200                 205

Val His Asp Arg Arg Lys Met Lys Pro Val Gln Phe Val Ala Ala Val
210                 215                 220

Ser Gln Asn Trp Thr Phe His Gly Pro Gly Ala Ser Gly Gln Ala Ala
225                 230                 235                 240

Ala Asn Trp Leu Ala Gly Phe Gly Arg Gly Pro Thr Pro Thr Leu
                245                 250                 255

Leu Gly Ile Arg Gln Asn Ala Asn Thr Thr Gly Arg Arg Leu Leu
            260                 265                 270

Val Leu Asp Glu Phe Lys Met Glu Lys Arg Ile Ser Arg Met Phe Tyr
        275                 280                 285

Ile Met Thr Phe Leu Phe Leu Thr Leu Trp Gly Pro Tyr Leu Val Ala
290                 295                 300

Cys Tyr Trp Arg Val Phe Ala Arg Gly Pro Val Val Pro Gly Gly Phe
305                 310                 315                 320

Leu Thr Ala Ala Val Trp Met Ser Phe Ala Gln Ala Gly Ile Asn Pro
                325                 330                 335

Phe Val Cys Ile Phe Ser Asn Arg Glu Leu Arg Arg Cys Phe Ser Thr
            340                 345                 350

Thr Leu Leu Tyr Cys Arg Lys Ser Arg Leu Pro Arg Glu Pro Tyr Cys
        355                 360                 365

Val Ile
370

<210> SEQ ID NO 29
<211> LENGTH: 1080
<212> TYPE: DNA
<213> ORGANISM: Homo sapiens

<400> SEQUENCE: 29
atgcaggtcc cgaacagcac cggcccggac aacgcgacgc tgcagatgct gcggaacccg     60
gcgatcgcgg tggccctgcc cgtggtgtac tcgctggtgg cggcggtcag catcccgggc    120
aacctcttct ctctgtgggt gctgtgccgg cgcatggggc ccagatcccc gtcggtcatc    180
ttcatgatca acctgagcgt cacggacctg atgctggcca gcgtgttgcc tttccaaatc    240
tactaccatt gcaaccgcca ccactgggta ttcggggtgc tgctttgcaa cgtggtgacc    300
gtggcctttt acgcaaacat gtattccagc atcctcacca tgacctgtat cagcgtggag    360
cgcttcctgg gggtcctgta cccgctcagc tccaagcgct ggcgccgccg tcgttacgcg    420
gtggccgcgt gtgcagggac ctggctgctg ctcctgaccg ccctgtgccc gctgcgcgc    480 accgatctca cctacccggt gcacgccctg ggcatcatca cctgcttcga cgtcctcaag    540
```

```
tggacgatgc tccccagcgt ggccatgtgg gccgtgttcc tcttcaccat cttcatcctg    600
ctgttcctca tcccgttcgt gatcaccgtg gcttgttaca cggccaccat cctcaagctg    660
ttgcgcacgg aggaggcgca cggccgggag cagcggaggc gcgcggtggg cctggccgcg    720
gtggtcttgc tggcctttgt cacctgcttc gcccccaaca acttcgtgct cctggcgcac    780
atcgtgagcc gcctgttcta cggcaagagc tactaccacg tgtacaagct cacgctgtgt    840
ctcagctgcc tcaacaactg tctggacccg tttgtttatt actttgcgtc ccgggaattc    900
cagctgcgcc tgcgggaata tttgggctgc cgccgggtgc ccagagacac cctggacacg    960
cgccgcgaga gctcttctc cgccaggacc acgtccgtgc gctccgaggc cggtgcgcac      1020
cctgaaggga tggagggagc caccaggccc ggcctccaga ggcaggagag tgtgttctga    1080
```

<210> SEQ ID NO 30
<211> LENGTH: 359
<212> TYPE: PRT
<213> ORGANISM: Homo sapiens

<400> SEQUENCE: 30

```
Met Gln Val Pro Asn Ser Thr Gly Pro Asp Asn Ala Thr Leu Gln Met
1               5                   10                  15

Leu Arg Asn Pro Ala Ile Ala Val Ala Leu Pro Val Val Tyr Ser Leu
            20                  25                  30

Val Ala Val Ser Ile Pro Gly Asn Leu Phe Ser Leu Trp Val Leu
        35                  40                  45

Cys Arg Arg Met Gly Pro Arg Ser Pro Ser Val Ile Phe Met Ile Asn
    50                  55                  60

Leu Ser Val Thr Asp Leu Met Leu Ala Ser Val Leu Pro Phe Gln Ile
65                  70                  75                  80

Tyr Tyr His Cys Asn Arg His His Trp Val Phe Gly Val Leu Leu Cys
                85                  90                  95

Asn Val Val Thr Val Ala Phe Tyr Ala Asn Met Tyr Ser Ser Ile Leu
            100                 105                 110

Thr Met Thr Cys Ile Ser Val Glu Arg Phe Leu Gly Val Leu Tyr Pro
        115                 120                 125

Leu Ser Ser Lys Arg Trp Arg Arg Arg Tyr Ala Val Ala Ala Cys
    130                 135                 140

Ala Gly Thr Trp Leu Leu Leu Leu Thr Ala Leu Cys Pro Leu Ala Arg
145                 150                 155                 160

Thr Asp Leu Thr Tyr Pro Val His Ala Leu Gly Ile Ile Thr Cys Phe
                165                 170                 175

Asp Val Leu Lys Trp Thr Met Leu Pro Ser Val Ala Met Trp Ala Val
            180                 185                 190

Phe Leu Phe Thr Ile Phe Ile Leu Leu Phe Leu Ile Pro Phe Val Ile
        195                 200                 205

Thr Val Ala Cys Tyr Thr Ala Thr Ile Leu Lys Leu Leu Arg Thr Glu
    210                 215                 220

Glu Ala His Gly Arg Glu Gln Arg Arg Arg Ala Val Gly Leu Ala Ala
225                 230                 235                 240

Val Val Leu Leu Ala Phe Val Thr Cys Phe Ala Pro Asn Asn Phe Val
                245                 250                 255

Leu Leu Ala His Ile Val Ser Arg Leu Phe Tyr Gly Lys Ser Tyr Tyr
            260                 265                 270

His Val Tyr Lys Leu Thr Leu Cys Leu Ser Cys Leu Asn Asn Cys Leu
        275                 280                 285
```

```
Asp Pro Phe Val Tyr Tyr Phe Ala Ser Arg Glu Phe Gln Leu Arg Leu
    290                 295                 300

Arg Glu Tyr Leu Gly Cys Arg Arg Val Pro Arg Asp Thr Leu Asp Thr
305                 310                 315                 320

Arg Arg Glu Ser Leu Phe Ser Ala Arg Thr Thr Ser Val Arg Ser Glu
                325                 330                 335

Ala Gly Ala His Pro Glu Gly Met Gly Gly Ala Thr Arg Pro Gly Leu
                340                 345                 350

Gln Arg Gln Glu Ser Val Phe
                355

<210> SEQ ID NO 31
<211> LENGTH: 1503
<212> TYPE: DNA
<213> ORGANISM: Homo sapiens

<400> SEQUENCE: 31
atggagcgtc cctgggagga cagcccaggc ccggagggg cagctgaggg ctcgcctgtg      60
ccagtcgccg ccggggcgcg ctccggtgcc gcggcgagtg gcacaggctg gcagccatgg    120
gctgagtgcc cggggaccccaa ggggagggg caactgctgg cgaccgccgg cccttttgcgt  180 cgctggcccg cccctcgcc tgccagctcc agccccgccc cggagcggc gtccgctcac     240 tcggttcaag gcagcgcgac tgcgggtggc gcacgaccag ggcgcagacc ttggggcgcg    300
cggcccatgg agtcggggct gctgcggccg cgcgccggtga gcgaggtcat cgtcctgcat   360
tacaactaca ccggcaagct ccgcggtgcg agctaccagc cgggtgccgg cctgcgcgcc   420
gacgccgtgg tgtgcctggc ggtgtgcgcc ttcatcgtgc tagagaatct agccgtgttg   480
ttggtgctcg gacgccaccc gcgcttccac gctcccatgt cctgctcct gggcagcctc   540 acgttgtcgg atctgctggc aggcgccgcc tacgccgcca acatcctact gtcggggccg   600
ctcacgctga aactgtcccc cgcgctctgg ttcgcacggg agggaggcgt cttcgtggca   660
ctcactgcgt ccgtgctgag cctcctggcc atcgcgctgg agcgcagcct caccatggcg   720 cgcaggggggc ccgcgcccgt ctccagtcgg gggcgcacgc tggcgatggc agccgcggcc   780
tggggcgtgt cgctgctcct cgggctcctg ccagcgctgg gctggaattg cctgggtcgc   840
ctggacgctt gctccactgt cttgccgctc tacgccaagg cctacgtgct cttctgcgtg   900
ctcgccttcg tgggcatcct ggccgcgatc tgtgcactct acgcgcgcat ctactgccag   960
gtacgcgcca acgcgcggcg cctgcggca cggcccggga ctgcggggac cacctcgacc  1020
cgggcgcgtc gcaagccgcg ctctctggcc ttgctgcgca cgctcagcgt ggtgctcctg  1080
gcctttgtgg catgttgggg ccccctcttc ctgctgctgt tgctcgacgt ggcgtgcccg  1140
gcgcgcacct gtcctgtact cctgcaggcc gatcccttcc tgggactggc catggccaac  1200
tcacttctga ccccatcat ctacacgctc accaaccgcg acctgcgcca cgcgctcctg   1260
cgcctggtct gctgcggacg ccactcctgc ggcagagacc cgagtggctc ccagcagtcg   1320
gcgagcgcgg ctgaggcttc cgggggcctg cgccgctgcc tgcccccggg ccttgatggg   1380
agcttcagcg gctcggagcg ctcatcgccc cagcgcgacg gctggacac cagcggctcc   1440 acaggcagcc ccggtgcacc cacagccgcc cggactctgg tatcagaacc ggctgcagac   1500
tga                                                                   1503

<210> SEQ ID NO 32
<211> LENGTH: 500
<212> TYPE: PRT
<213> ORGANISM: Homo sapiens
```

<400> SEQUENCE: 32

```
Met Glu Arg Pro Trp Glu Asp Ser Pro Gly Pro Glu Gly Ala Ala Glu
1               5                   10                  15

Gly Ser Pro Val Pro Val Ala Ala Gly Ala Arg Ser Gly Ala Ala Ala
            20                  25                  30

Ser Gly Thr Gly Trp Gln Pro Trp Ala Glu Cys Pro Gly Pro Lys Gly
        35                  40                  45

Arg Gly Gln Leu Leu Ala Thr Ala Gly Pro Leu Arg Arg Trp Pro Ala
50                  55                  60

Pro Ser Pro Ala Ser Ser Pro Ala Pro Gly Ala Ala Ser Ala His
65                  70                  75                  80

Ser Val Gln Gly Ser Ala Thr Ala Gly Gly Ala Arg Pro Gly Arg Arg
                85                  90                  95

Pro Trp Gly Ala Arg Pro Met Glu Ser Gly Leu Leu Arg Pro Ala Pro
            100                 105                 110

Val Ser Glu Val Ile Val Leu His Tyr Asn Tyr Thr Gly Lys Leu Arg
        115                 120                 125

Gly Ala Ser Tyr Gln Pro Gly Ala Gly Leu Arg Ala Asp Ala Val Val
130                 135                 140

Cys Leu Ala Val Cys Ala Phe Ile Val Leu Glu Asn Leu Ala Val Leu
145                 150                 155                 160

Leu Val Leu Gly Arg His Pro Arg Phe His Ala Pro Met Phe Leu Leu
                165                 170                 175

Leu Gly Ser Leu Thr Leu Ser Asp Leu Leu Ala Gly Ala Ala Tyr Ala
            180                 185                 190

Ala Asn Ile Leu Leu Ser Gly Pro Leu Thr Leu Lys Leu Ser Pro Ala
        195                 200                 205

Leu Trp Phe Ala Arg Glu Gly Gly Val Phe Val Ala Leu Thr Ala Ser
210                 215                 220

Val Leu Ser Leu Leu Ala Ile Ala Leu Glu Arg Ser Leu Thr Met Ala
225                 230                 235                 240

Arg Arg Gly Pro Ala Pro Val Ser Ser Arg Gly Arg Thr Leu Ala Met
                245                 250                 255

Ala Ala Ala Ala Trp Gly Val Ser Leu Leu Leu Gly Leu Leu Pro Ala
            260                 265                 270

Leu Gly Trp Asn Cys Leu Gly Arg Leu Asp Ala Cys Ser Thr Val Leu
        275                 280                 285

Pro Leu Tyr Ala Lys Ala Tyr Val Leu Phe Cys Val Leu Ala Phe Val
290                 295                 300

Gly Ile Leu Ala Ala Ile Cys Ala Leu Tyr Ala Arg Ile Tyr Cys Gln
305                 310                 315                 320

Val Arg Ala Asn Ala Arg Arg Leu Pro Ala Arg Pro Gly Thr Ala Gly
                325                 330                 335

Thr Thr Ser Thr Arg Ala Arg Arg Lys Pro Arg Ser Leu Ala Leu Leu
            340                 345                 350

Arg Thr Leu Ser Val Val Leu Leu Ala Phe Val Ala Cys Trp Gly Pro
        355                 360                 365

Leu Phe Leu Leu Leu Leu Leu Asp Val Ala Cys Pro Ala Arg Thr Cys
370                 375                 380

Pro Val Leu Leu Gln Ala Asp Pro Phe Leu Gly Leu Ala Met Ala Asn
385                 390                 395                 400

Ser Leu Leu Asn Pro Ile Ile Tyr Thr Leu Thr Asn Arg Asp Leu Arg
                405                 410                 415
```

His Ala Leu Leu Arg Leu Val Cys Cys Gly Arg His Ser Cys Gly Arg
            420                 425                 430

Asp Pro Ser Gly Ser Gln Gln Ser Ala Ser Ala Glu Ala Ser Gly
        435                 440                 445

Gly Leu Arg Arg Cys Leu Pro Pro Gly Leu Asp Gly Ser Phe Ser Gly
        450                 455                 460

Ser Glu Arg Ser Ser Pro Gln Arg Asp Gly Leu Asp Thr Ser Gly Ser
465                 470                 475                 480

Thr Gly Ser Pro Gly Ala Pro Thr Ala Ala Arg Thr Leu Val Ser Glu
                485                 490                 495

Pro Ala Ala Asp
        500

<210> SEQ ID NO 33
<211> LENGTH: 1029
<212> TYPE: DNA
<213> ORGANISM: Homo sapiens

<400> SEQUENCE: 33

```
atgcaagccg tcgacaatct cacctctgcg cctgggaaca ccagtctgtg caccagagac    60
tacaaaatca cccaggtcct cttcccactg ctctacactg tcctgttttt tgttggactt   120
atcacaaatg gcctggcgat gaggattttc tttcaaatcc ggagtaaatc aaactttatt   180
attttcctta gaacacagt catttctgat cttctcatga ttctgacttt tccattcaaa   240
attcttagtg atgccaaact gggaacagga ccactgagaa cttttgtgtg tcaagttacc   300
tccgtcatat tttatttcac aatgtatatc agtatttcat tcctgggact gataactatc   360
gatcgctacc agaagaccac caggccattt aaaacatcca ccccaaaaa tctcttgggg   420
gctaagattc tctctgttgt catctgggca ttcatgttct tactctcttt gcctaacatg   480
attctgacca caggcagcc gagagacaag aatgtgaaga atgctctttt ccttaaatca   540
gagttcggtc tagtctggca tgaaatagta aattacatct gtcaagtcat tttctggatt   600
aatttcttaa ttgttattgt atgttataca ctcattacaa agaactgta ccggtcatac   660
gtaagaacga ggggtgtagg taaagtcccc aggaaaaagg tgaacgtcaa agttttcatt   720
atcattgctg tattctttat ttgttttgtt cctttccatt ttgcccgaat tcctacacc   780
ctgagccaaa cccgggatgt cttttgactgc actgctgaaa atactctgtt ctatgtgaaa   840
gagagcactc tgtggttaac ttccttaaat gcatgcctgg atccgttcat ctattttttc   900
ctttgcaagt ccttcagaaa ttccttgata agtatgctga agtgccccaa ttctgcaaca   960
tctctgtccc aggacaatag gaaaaagaa caggatggtg gtgacccaaa tgaagagact  1020
ccaatgtaa                                                          1029
```

<210> SEQ ID NO 34
<211> LENGTH: 342
<212> TYPE: PRT
<213> ORGANISM: Homo sapiens

<400> SEQUENCE: 34

Met Gln Ala Val Asp Asn Leu Thr Ser Ala Pro Gly Asn Thr Ser Leu
1               5                   10                  15

Cys Thr Arg Asp Tyr Lys Ile Thr Gln Val Leu Phe Pro Leu Leu Tyr
            20                  25                  30

Thr Val Leu Phe Phe Val Gly Leu Ile Thr Asn Gly Leu Ala Met Arg
        35                  40                  45

```
Ile Phe Phe Gln Ile Arg Ser Lys Ser Asn Phe Ile Ile Phe Leu Lys
 50                  55                  60

Asn Thr Val Ile Ser Asp Leu Leu Met Ile Leu Thr Phe Pro Phe Lys
 65                  70                  75                  80

Ile Leu Ser Asp Ala Lys Leu Gly Thr Gly Pro Leu Arg Thr Phe Val
                 85                  90                  95

Cys Gln Val Thr Ser Val Ile Phe Tyr Phe Thr Met Tyr Ile Ser Ile
                100                 105                 110

Ser Phe Leu Gly Leu Ile Thr Ile Asp Arg Tyr Gln Lys Thr Thr Arg
            115                 120                 125

Pro Phe Lys Thr Ser Asn Pro Lys Asn Leu Leu Gly Ala Lys Ile Leu
        130                 135                 140

Ser Val Val Ile Trp Ala Phe Met Phe Leu Leu Ser Leu Pro Asn Met
145                 150                 155                 160

Ile Leu Thr Asn Arg Gln Pro Arg Asp Lys Asn Val Lys Lys Cys Ser
                165                 170                 175

Phe Leu Lys Ser Glu Phe Gly Leu Val Trp His Glu Ile Val Asn Tyr
            180                 185                 190

Ile Cys Gln Val Ile Phe Trp Ile Asn Phe Leu Ile Val Ile Val Cys
        195                 200                 205

Tyr Thr Leu Ile Thr Lys Glu Leu Tyr Arg Ser Tyr Val Arg Thr Arg
210                 215                 220

Gly Val Gly Lys Val Pro Arg Lys Lys Val Asn Val Lys Val Phe Ile
225                 230                 235                 240

Ile Ile Ala Val Phe Phe Ile Cys Phe Val Pro Phe His Phe Ala Arg
                245                 250                 255

Ile Pro Tyr Thr Leu Ser Gln Thr Arg Asp Val Phe Asp Cys Thr Ala
            260                 265                 270

Glu Asn Thr Leu Phe Tyr Val Lys Glu Ser Thr Leu Trp Leu Thr Ser
        275                 280                 285

Leu Asn Ala Cys Leu Asp Pro Phe Ile Tyr Phe Phe Leu Cys Lys Ser
290                 295                 300

Phe Arg Asn Ser Leu Ile Ser Met Leu Lys Cys Pro Asn Ser Ala Thr
305                 310                 315                 320

Ser Leu Ser Gln Asp Asn Arg Lys Lys Glu Gln Asp Gly Gly Asp Pro
                325                 330                 335

Asn Glu Glu Thr Pro Met
            340

<210> SEQ ID NO 35
<211> LENGTH: 1077
<212> TYPE: DNA
<213> ORGANISM: Homo sapiens

<400> SEQUENCE: 35
atgtcggtct gctaccgtcc cccagggaac gagacactgc tgagctggaa gacttcgcgg      60
gccacaggca cagccttcct gctgctggcg gcgctgctgg ggctgcctgg caacggcttc     120
gtggtgtgga gcttggcggg ctggcggcct gcacgggggc gaccgctggc ggccacgctt     180
gtgctgcacc tggcgctggc cgacggcgcg gtgctgctgc tcacgccgct ctttgtggcc     240
ttcctgaccc ggcaggcctg gccgctgggc caggcgggct gcaaggcggt gtactacgtg     300
tgcgcgctca gcatgtacgc cagcgtgctg ctcaccggcc tgctcagcct gcagcgctgc     360
ctcgcagtca cccgcccctt cctggcgcct ggctgcgca gcccgccct ggcccgccgc      420 ctgctgctgg cggtctggct ggccgccctg ttgctcgccg tcccggccgc cgtctaccgc     480
```

```
cacctgtgga gggaccgcgt atgccagctg tgccacccgt cgccggtcca cgccgccgcc   540
cacctgagcc tggagactct gaccgctttc gtgcttcctt tcgggctgat gctcggctgc   600
tacagcgtga cgctggcacg gctgcggggc gcccgctggg gctccgggcg cacggggcg    660
cgggtgggcc ggctggtgag cgccatcgtg cttgccttcg gcttgctctg gcccctac     720
cacgcagtca accttctgca ggcggtcgca gcgctggctc accggaagg  ggccttggcg   780
aagctgggcg gagccggcca ggcggcgcga gcgggaacta cggccttggc cttcttcagt   840
tctagcgtca acccggtgct ctacgtcttc accgctggag atctgctgcc ccgggcaggt   900
ccccgtttcc tcacgcggct cttcgaaggc tctggggagg cccgagggg  cggccgctct   960
agggaaggga ccatggagct ccgaactacc cctcagctga agtggtggg gcagggccgc   1020
ggcaatggag acccgggggg tgggatggag aaggacggtc cggaatggga cctttga      1077
```

```
<210> SEQ ID NO 36
<211> LENGTH: 358
<212> TYPE: PRT
<213> ORGANISM: Homo sapiens

<400> SEQUENCE: 36

Met Ser Val Cys Tyr Arg Pro Pro Gly Asn Glu Thr Leu Leu Ser Trp
1               5                   10                  15

Lys Thr Ser Arg Ala Thr Gly Thr Ala Phe Leu Leu Ala Ala Leu
            20                  25                  30

Leu Gly Leu Pro Gly Asn Gly Phe Val Val Trp Ser Leu Ala Gly Trp
        35                  40                  45

Arg Pro Ala Arg Gly Arg Pro Leu Ala Ala Thr Leu Val Leu His Leu
    50                  55                  60

Ala Leu Ala Asp Gly Ala Val Leu Leu Leu Thr Pro Leu Phe Val Ala
65                  70                  75                  80

Phe Leu Thr Arg Gln Ala Trp Pro Leu Gly Gln Ala Gly Cys Lys Ala
                85                  90                  95

Val Tyr Tyr Val Cys Ala Leu Ser Met Tyr Ala Ser Val Leu Leu Thr
            100                 105                 110

Gly Leu Leu Ser Leu Gln Arg Cys Leu Ala Val Thr Arg Pro Phe Leu
        115                 120                 125

Ala Pro Arg Leu Arg Ser Pro Ala Leu Ala Arg Arg Leu Leu Leu Ala
    130                 135                 140

Val Trp Leu Ala Ala Leu Leu Leu Ala Val Pro Ala Ala Val Tyr Arg
145                 150                 155                 160

His Leu Trp Arg Asp Arg Val Cys Gln Leu Cys His Pro Ser Pro Val
                165                 170                 175

His Ala Ala Ala His Leu Ser Leu Glu Thr Leu Thr Ala Phe Val Leu
            180                 185                 190

Pro Phe Gly Leu Met Leu Gly Cys Tyr Ser Val Thr Leu Ala Arg Leu
        195                 200                 205

Arg Gly Ala Arg Trp Gly Ser Gly Arg His Gly Ala Arg Val Gly Arg
    210                 215                 220

Leu Val Ser Ala Ile Val Leu Ala Phe Gly Leu Leu Trp Ala Pro Tyr
225                 230                 235                 240

His Ala Val Asn Leu Leu Gln Ala Val Ala Ala Leu Ala Pro Pro Glu
                245                 250                 255

Gly Ala Leu Ala Lys Leu Gly Gly Ala Gly Gln Ala Ala Arg Ala Gly
            260                 265                 270
```

```
Thr Thr Ala Leu Ala Phe Phe Ser Ser Val Asn Pro Val Leu Tyr
        275                 280                 285

Val Phe Thr Ala Gly Asp Leu Leu Pro Arg Ala Gly Pro Arg Phe Leu
290                 295                 300

Thr Arg Leu Phe Glu Gly Ser Gly Glu Ala Arg Gly Gly Gly Arg Ser
305                 310                 315                 320

Arg Glu Gly Thr Met Glu Leu Arg Thr Thr Pro Gln Leu Lys Val Val
                325                 330                 335

Gly Gln Gly Arg Gly Asn Gly Asp Pro Gly Gly Met Glu Lys Asp
            340                 345                 350

Gly Pro Glu Trp Asp Leu
        355

<210> SEQ ID NO 37
<211> LENGTH: 1005
<212> TYPE: DNA
<213> ORGANISM: Homo sapiens

<400> SEQUENCE: 37
atgctgggga tcatggcatg gaatgcaact tgcaaaaact ggctggcagc agaggctgcc      60
ctggaaaagt actacctttc cattttttat gggattgagt tcgttgtggg agtccttgga     120
aataccattg ttgtttacgg ctacatcttc tctctgaaga actggaacag cagtaatatt     180
tatctcttta acctctctgt tctgacttta gcttttctgt gcaccctccc catgctgata     240
aggagttatg ccaatggaaa ctggatatat ggagacgtgc tctgcataag caaccgatat     300
gtgcttcatg ccaacctcta taccagcatt ctctttctca cttttatcag catagatcga     360
tacttgataa ttaagtatcc tttccgagaa caccttctgc aaaagaaaga gtttgctatt     420
ttaatctcct tggccatttg ggttttagta acttagagt tactacccat acttcccctt      480
ataaatcctg ttataactga caatggcacc acctgtaatg attttgcaag ttctggagac     540
cccaactaca acctcattta cagcatgtgt ctaacactgt tgggttcct tattcctctt      600 tttgtgatgt gtttcttta ttacaagatt gctctcttcc taaagcagag gaataggcag     660
gttgctactg ctctgccct tgaaaagcct ctcaacttgg tcatcatggc agtggtaatc     720
ttctctgtgc ttttttacacc ctatcacgtc atgcggaatg tgaggatcgc ttcacgcctg     780
gggagttgga agcagtatca gtgcactcag gtcgtcatca actcctttta cattgtgaca     840
cggcctttgg cctttctgaa cagtgtcatc aaccctgtct ctatttctct tttgggagat     900
cacttcaggg acatgctgat gaatcaactg agacacaact tcaaatccct tacatccttt     960
agcagatggg ctcatgaact cctactttca ttcagagaaa agtga               1005

<210> SEQ ID NO 38
<211> LENGTH: 334
<212> TYPE: PRT
<213> ORGANISM: Homo sapiens

<400> SEQUENCE: 38

Met Leu Gly Ile Met Ala Trp Asn Ala Thr Cys Lys Asn Trp Leu Ala
1               5                   10                  15

Ala Glu Ala Ala Leu Glu Lys Tyr Tyr Leu Ser Ile Phe Tyr Gly Ile
            20                  25                  30

Glu Phe Val Val Gly Val Leu Gly Asn Thr Ile Val Val Tyr Gly Tyr
        35                  40                  45

Ile Phe Ser Leu Lys Asn Trp Asn Ser Ser Asn Ile Tyr Leu Phe Asn
    50                  55                  60
```

```
Leu Ser Val Ser Asp Leu Ala Phe Leu Cys Thr Leu Pro Met Leu Ile
 65                  70                  75                  80

Arg Ser Tyr Ala Asn Gly Asn Trp Ile Tyr Gly Asp Val Leu Cys Ile
                 85                  90                  95

Ser Asn Arg Tyr Val Leu His Ala Asn Leu Tyr Thr Ser Ile Leu Phe
            100                 105                 110

Leu Thr Phe Ile Ser Ile Asp Arg Tyr Leu Ile Ile Lys Tyr Pro Phe
        115                 120                 125

Arg Glu His Leu Leu Gln Lys Lys Glu Phe Ala Ile Leu Ile Ser Leu
    130                 135                 140

Ala Ile Trp Val Leu Val Thr Leu Glu Leu Leu Pro Ile Leu Pro Leu
145                 150                 155                 160

Ile Asn Pro Val Ile Thr Asp Asn Gly Thr Thr Cys Asn Asp Phe Ala
                165                 170                 175

Ser Ser Gly Asp Pro Asn Tyr Asn Leu Ile Tyr Ser Met Cys Leu Thr
            180                 185                 190

Leu Leu Gly Phe Leu Ile Pro Leu Phe Val Met Cys Phe Phe Tyr Tyr
        195                 200                 205

Lys Ile Ala Leu Phe Leu Lys Gln Arg Asn Arg Gln Val Ala Thr Ala
    210                 215                 220

Leu Pro Leu Glu Lys Pro Leu Asn Leu Val Ile Met Ala Val Val Ile
225                 230                 235                 240

Phe Ser Val Leu Phe Thr Pro Tyr His Val Met Arg Asn Val Arg Ile
                245                 250                 255

Ala Ser Arg Leu Gly Ser Trp Lys Gln Tyr Gln Cys Thr Gln Val Val
            260                 265                 270

Ile Asn Ser Phe Tyr Ile Val Thr Arg Pro Leu Ala Phe Leu Asn Ser
        275                 280                 285

Val Ile Asn Pro Val Phe Tyr Phe Leu Leu Gly Asp His Phe Arg Asp
    290                 295                 300

Met Leu Met Asn Gln Leu Arg His Asn Phe Lys Ser Leu Thr Ser Phe
305                 310                 315                 320

Ser Arg Trp Ala His Glu Leu Leu Leu Ser Phe Arg Glu Lys
                325                 330

<210> SEQ ID NO 39
<211> LENGTH: 1296
<212> TYPE: DNA
<213> ORGANISM: Homo sapiens

<400> SEQUENCE: 39
atgcaggcgc ttaacattac cccggagcag ttctctcggc tgctgcggga ccacaacctg      60
acgcgggagc agttcatcgc tctgtaccgg ctgcgaccgc tcgtctacac cccagagctg     120
ccgggacgcg ccaagctggc cctcgtgctc accggcgtgc tcatcttcgc cctggcgctc     180
tttggcaatg ctctggtgtt ctacgtggtg acccgcagca aggccatgcg caccgtcacc     240
aacatcttta tctgctccct ggcgctcagt gacctgctca tcaccttctt ctgcattccc     300
gtcaccatgc tccagaacat ttccgacaac tggctggggg tgctttcat ttgcaagatg     360 gtgccatttg tccagtctac cgctgttgtg acagaaatgc tcactatgac ctgcattgct     420
gtggaaaggc accagggact tgtgcatcct tttaaaatga gtggcaata caccaaccga     480 agggctttca caatgctagg tgtggtctgg ctggtggcag tcatcgtagg atcacccatg     540
tggcacgtgc aacaacttga gatcaaatat gacttcctat atgaaaagga acacatctgc     600
tgcttagaag agtggaccag ccctgtgcac cagaagatct acaccacctt catccttgtc     660
```

```
atcctcttcc tcctgcctct tatggtgatg cttattctgt acagtaaaat tggttatgaa    720
ctttggataa agaaaagagt tggggatggt tcagtgcttc gaactattca tggaaaagaa    780
atgtccaaaa tagccaggaa gaagaaacga gctgtcatta tgatggtgac agtggtggct    840
ctctttgctg tgtgctgggc accattccat gttgtccata tgatgattga atacagtaat    900
tttgaaaagg aatatgatga tgtcacaatc aagatgattt ttgctatcgt gcaaattatt    960
ggattttcca actccatctg taatcccatt gtctatgcat ttatgaatga aaacttcaaa   1020
aaaaatgttt tgtctgcagt ttgttattgc atagtaaaata aaaccttctc tccagcacaa   1080
aggcatggaa attcaggaat tacaatgatg cggaagaaag caaagttttc cctcagagag   1140
aatccagtgg aggaaaccaa aggagaagca ttcagtgatg caacattga agtcaaattg   1200 tgtgaacaga cagaggagaa gaaaaagctc aaacgacatc ttgctctctt taggtctgaa   1260
ctggctgaga attctccttt agacagtggg cattaa                              1296

<210> SEQ ID NO 40
<211> LENGTH: 431
<212> TYPE: PRT
<213> ORGANISM: Homo sapiens

<400> SEQUENCE: 40

Met Gln Ala Leu Asn Ile Thr Pro Glu Gln Phe Ser Arg Leu Leu Arg
 1               5                  10                  15

Asp His Asn Leu Thr Arg Glu Gln Phe Ile Ala Leu Tyr Arg Leu Arg
             20                  25                  30

Pro Leu Val Tyr Thr Pro Glu Leu Pro Gly Arg Ala Lys Leu Ala Leu
         35                  40                  45

Val Leu Thr Gly Val Leu Ile Phe Ala Leu Ala Leu Phe Gly Asn Ala
     50                  55                  60

Leu Val Phe Tyr Val Val Thr Arg Ser Lys Ala Met Arg Thr Val Thr
 65                  70                  75                  80

Asn Ile Phe Ile Cys Ser Leu Ala Leu Ser Asp Leu Leu Ile Thr Phe
                 85                  90                  95

Phe Cys Ile Pro Val Thr Met Leu Gln Asn Ile Ser Asp Asn Trp Leu
            100                 105                 110

Gly Gly Ala Phe Ile Cys Lys Met Val Pro Phe Val Gln Ser Thr Ala
        115                 120                 125

Val Val Thr Glu Met Leu Thr Met Thr Cys Ile Ala Val Glu Arg His
    130                 135                 140

Gln Gly Leu Val His Pro Phe Lys Met Lys Trp Gln Tyr Thr Asn Arg
145                 150                 155                 160

Arg Ala Phe Thr Met Leu Gly Val Val Trp Leu Val Ala Val Ile Val
                165                 170                 175

Gly Ser Pro Met Trp His Val Gln Gln Leu Glu Ile Lys Tyr Asp Phe
            180                 185                 190

Leu Tyr Glu Lys Glu His Ile Cys Cys Leu Glu Glu Trp Thr Ser Pro
        195                 200                 205

Val His Gln Lys Ile Tyr Thr Thr Phe Ile Leu Val Ile Leu Phe Leu
    210                 215                 220

Leu Pro Leu Met Val Met Leu Ile Leu Tyr Ser Lys Ile Gly Tyr Glu
225                 230                 235                 240

Leu Trp Ile Lys Lys Arg Val Gly Asp Gly Ser Val Leu Arg Thr Ile
                245                 250                 255

His Gly Lys Glu Met Ser Lys Ile Ala Arg Lys Lys Lys Arg Ala Val
```

```
                260                 265                 270
Ile Met Met Val Thr Val Val Ala Leu Phe Ala Val Cys Trp Ala Pro
            275                 280                 285

Phe His Val Val His Met Met Ile Glu Tyr Ser Asn Phe Glu Lys Glu
        290                 295                 300

Tyr Asp Asp Val Thr Ile Lys Met Ile Phe Ala Ile Val Gln Ile Ile
305                 310                 315                 320

Gly Phe Ser Asn Ser Ile Cys Asn Pro Ile Val Tyr Ala Phe Met Asn
                325                 330                 335

Glu Asn Phe Lys Lys Asn Val Leu Ser Ala Val Cys Tyr Cys Ile Val
            340                 345                 350

Asn Lys Thr Phe Ser Pro Ala Gln Arg His Gly Asn Ser Gly Ile Thr
        355                 360                 365

Met Met Arg Lys Lys Ala Lys Phe Ser Leu Arg Glu Asn Pro Val Glu
    370                 375                 380

Glu Thr Lys Gly Glu Ala Phe Ser Asp Gly Asn Ile Glu Val Lys Leu
385                 390                 395                 400

Cys Glu Gln Thr Glu Glu Lys Lys Leu Lys Arg His Leu Ala Leu
                405                 410                 415

Phe Arg Ser Glu Leu Ala Glu Asn Ser Pro Leu Asp Ser Gly His
            420                 425                 430

<210> SEQ ID NO 41
<211> LENGTH: 24
<212> TYPE: DNA
<213> ORGANISM: Artificial Sequence
<220> FEATURE:
<223> OTHER INFORMATION: Novel Sequence

<400> SEQUENCE: 41
ctgtgtacag cagttcgcag agtg                                      24

<210> SEQ ID NO 42
<211> LENGTH: 24
<212> TYPE: DNA
<213> ORGANISM: Artificial Sequence
<220> FEATURE:
<223> OTHER INFORMATION: Novel Sequence

<400> SEQUENCE: 42
gagtgccagg cagagcaggt agac                                      24

<210> SEQ ID NO 43
<211> LENGTH: 31
<212> TYPE: DNA
<213> ORGANISM: Artificial Sequence
<220> FEATURE:
<223> OTHER INFORMATION: Novel Sequence

<400> SEQUENCE: 43
cccgaattcc tgcttgctcc cagcttggcc c                              31

<210> SEQ ID NO 44
<211> LENGTH: 32
<212> TYPE: DNA
<213> ORGANISM: Artificial Sequence
<220> FEATURE:
<223> OTHER INFORMATION: Novel Sequence

<400> SEQUENCE: 44
tgtggatcct gctgtcaaag gtcccattcc gg                             32
```

```
<210> SEQ ID NO 45
<211> LENGTH: 20
<212> TYPE: DNA
<213> ORGANISM: Artificial Sequence
<220> FEATURE:
<223> OTHER INFORMATION: Novel Sequence

<400> SEQUENCE: 45
tcacaatgct aggtgtggtc                                                    20

<210> SEQ ID NO 46
<211> LENGTH: 22
<212> TYPE: DNA
<213> ORGANISM: Artificial Sequence
<220> FEATURE:
<223> OTHER INFORMATION: Novel Sequence

<400> SEQUENCE: 46
tgcatagaca atgggattac ag                                                 22

<210> SEQ ID NO 47
<211> LENGTH: 511
<212> TYPE: DNA
<213> ORGANISM: Homo sapiens

<400> SEQUENCE: 47
tcacaatgct aggtgtggtc tggctggtgg cagtcatcgt aggatcaccc atgtggcacg        60
tgcaacaact tgagatcaaa tatgacttcc tatatgaaaa ggaacacatc tgctgcttag       120
aagagtggac cagccctgtg caccagaaga tctacaccac cttcatcctt gtcatcctct       180
tcctcctgcc tcttatggtg atgcttattc tgtacgtaaa attggttatg aactttggat       240
aaagaaaaga gttggggatg gttcagtgct tcgaactatt catggaaaag aaatgtccaa       300
aatagccagg aagaagaaac gagctgtcat tatgatggtg acagtggtgg ctctcttgc        360 tgtgtgctgg gcaccattcc atgttgtcca tatgatgatt gaatacagta attttgaaaa       420
ggaatatgat gatgtcacaa tcaagatgat ttttgctatc gtgcaaatta ttggatttc        480 caactccatc tgtaatccca ttgtctatgc a                                      511

<210> SEQ ID NO 48
<211> LENGTH: 21
<212> TYPE: DNA
<213> ORGANISM: Artificial Sequence
<220> FEATURE:
<223> OTHER INFORMATION: Novel Sequence

<400> SEQUENCE: 48
ctgcttagaa gagtggacca g                                                  21

<210> SEQ ID NO 49
<211> LENGTH: 22
<212> TYPE: DNA
<213> ORGANISM: Artificial Sequence
<220> FEATURE:
<223> OTHER INFORMATION: Novel Sequence

<400> SEQUENCE: 49
ctgtgcacca gaagatctac ac                                                 22

<210> SEQ ID NO 50
<211> LENGTH: 21
<212> TYPE: DNA
<213> ORGANISM: Artificial Sequence
<220> FEATURE:
```

<223> OTHER INFORMATION: Novel Sequence

<400> SEQUENCE: 50
caaggatgaa ggtggtgtag a                                    21

<210> SEQ ID NO 51
<211> LENGTH: 23
<212> TYPE: DNA
<213> ORGANISM: Artificial Sequence
<220> FEATURE:
<223> OTHER INFORMATION: Novel Sequence

<400> SEQUENCE: 51
gtgtagatct tctggtgcac agg                                  23

<210> SEQ ID NO 52
<211> LENGTH: 21
<212> TYPE: DNA
<213> ORGANISM: Artificial Sequence
<220> FEATURE:
<223> OTHER INFORMATION: Novel Sequence

<400> SEQUENCE: 52
gcaatgcagg tcatagtgag c                                    21

<210> SEQ ID NO 53
<211> LENGTH: 27
<212> TYPE: DNA
<213> ORGANISM: Artificial Sequence
<220> FEATURE:
<223> OTHER INFORMATION: Novel Sequence

<400> SEQUENCE: 53
tggagcatgg tgacgggaat gcagaag                              27

<210> SEQ ID NO 54
<211> LENGTH: 27
<212> TYPE: DNA
<213> ORGANISM: Artificial Sequence
<220> FEATURE:
<223> OTHER INFORMATION: Novel Sequence

<400> SEQUENCE: 54
gtgatgagca ggtcactgag cgccaag                              27

<210> SEQ ID NO 55
<211> LENGTH: 23
<212> TYPE: DNA
<213> ORGANISM: Artificial Sequence
<220> FEATURE:
<223> OTHER INFORMATION: Novel Sequence

<400> SEQUENCE: 55
gcaatgcagg cgcttaacat tac                                  23

<210> SEQ ID NO 56
<211> LENGTH: 22
<212> TYPE: DNA
<213> ORGANISM: Artificial Sequence
<220> FEATURE:
<223> OTHER INFORMATION: Novel Sequence

<400> SEQUENCE: 56
ttgggttaca atctgaaggg ca                                   22

<210> SEQ ID NO 57

```
<211> LENGTH: 23
<212> TYPE: DNA
<213> ORGANISM: Artificial Sequence
<220> FEATURE:
<223> OTHER INFORMATION: Novel Sequence

<400> SEQUENCE: 57
actccgtgtc cagcaggact ctg                                        23

<210> SEQ ID NO 58
<211> LENGTH: 24
<212> TYPE: DNA
<213> ORGANISM: Artificial Sequence
<220> FEATURE:
<223> OTHER INFORMATION: Novel Sequence

<400> SEQUENCE: 58
tgcgtgttcc tggaccctca cgtg                                       24

<210> SEQ ID NO 59
<211> LENGTH: 29
<212> TYPE: DNA
<213> ORGANISM: Artificial Sequence
<220> FEATURE:
<223> OTHER INFORMATION: Novel Sequence

<400> SEQUENCE: 59
caggccttgg attttaatgt cagggatgg                                  29

<210> SEQ ID NO 60
<211> LENGTH: 27
<212> TYPE: DNA
<213> ORGANISM: Artificial Sequence
<220> FEATURE:
<223> OTHER INFORMATION: Novel Sequence

<400> SEQUENCE: 60
ggagagtcag ctctgaaaga attcagg                                    27

<210> SEQ ID NO 61
<211> LENGTH: 27
<212> TYPE: DNA
<213> ORGANISM: Artificial Sequence
<220> FEATURE:
<223> OTHER INFORMATION: Novel Sequence

<400> SEQUENCE: 61
tgatgtgatg ccagatacta atagcac                                    27

<210> SEQ ID NO 62
<211> LENGTH: 27
<212> TYPE: DNA
<213> ORGANISM: Artificial Sequence
<220> FEATURE:
<223> OTHER INFORMATION: Novel Sequence

<400> SEQUENCE: 62
cctgattcat ttaggtgaga ttgagac                                    27

<210> SEQ ID NO 63
<211> LENGTH: 26
<212> TYPE: DNA
<213> ORGANISM: Artificial Sequence
<220> FEATURE:
<223> OTHER INFORMATION: Novel Sequence

<400> SEQUENCE: 63
```

```
cccaagcttc cccaggtgta tttgat                                          26
```

<210> SEQ ID NO 64
<211> LENGTH: 26
<212> TYPE: DNA
<213> ORGANISM: Artificial Sequence
<220> FEATURE:
<223> OTHER INFORMATION: Novel Sequence

<400> SEQUENCE: 64

```
gttggatcca cataatgcat tttctc                                          26
```

<210> SEQ ID NO 65
<211> LENGTH: 1080
<212> TYPE: DNA
<213> ORGANISM: Homo sapiens

<400> SEQUENCE: 65

```
atgattctca actcttctac tgaagatggt attaaaagaa tccaagatga ttgtcccaaa     60
gctggaaggc ataattacat atttgtcatg attcctactt tatacagtat catctttgtg    120
gtgggaatat ttggaaacag cttggtggtg atagtcattt acttttatat gaagctgaag    180
actgtggcca gtgttttttct tttgaattta gcactggctg acttatgctt tttactgact   240
ttgccactat gggctgtcta cacagctatg gaataccgct ggcccttttgg caattaccta   300
tgtaagattg cttcagccag cgtcagtttc aacctgtacg ctagtgtgtt tctactcacg    360
tgtctcagca ttgatcgata cctggctatt gttcacccaa tgaagtcccg ccttcgacgc    420
acaatgcttg tagccaaagt cacctgcatc atcatttggc tgctggcagg cttggccagt   480
ttgccagcta taatccatcg aaatgtattt ttcattgaga acaccaatat tacagtttgt    540
gctttccatt atgagtccca aaattcaacc cttccgatag ggctgggcct gaccaaaaat    600
atactgggtt tcctgtttcc ttttctgatc attcttacaa gttatactct tatttggaag    660
gccctaaaga aggcttatga aattcagaag aacaaaccaa gaaatgatga tatttttaag   720
ataattatgg caattgtgct tttctttttc ttttcctgga ttccccacca aatattcact    780
tttctggatg tattgattca actaggcatc atacgtgact gtagaattgc agatattgtg    840
gacacggcca tgcctatcac catttgtata gcttatttta caattgcctt gaatcctctt   900
ttttatggct ttctggggaa aaaatttaaa agatattttc tccagcttct aaaatatatt    960
cccccaaaag ccaaatccca ctcaaacctt tcaacaaaaa tgagcacgct ttcctaccgc   1020
ccctcagata atgtaagctc atccaccaag aagcctgcac catgttttga ggttgagtga   1080
```

<210> SEQ ID NO 66
<211> LENGTH: 359
<212> TYPE: PRT
<213> ORGANISM: Homo sapiens

<400> SEQUENCE: 66

```
Met Ile Leu Asn Ser Ser Thr Glu Asp Gly Ile Lys Arg Ile Gln Asp
1               5                   10                  15

Asp Cys Pro Lys Ala Gly Arg His Asn Tyr Ile Phe Val Met Ile Pro
            20                  25                  30

Thr Leu Tyr Ser Ile Ile Phe Val Val Gly Ile Phe Gly Asn Ser Leu
        35                  40                  45

Val Val Ile Val Ile Tyr Phe Tyr Met Lys Leu Lys Thr Val Ala Ser
    50                  55                  60

Val Phe Leu Leu Asn Leu Ala Leu Ala Asp Leu Cys Phe Leu Leu Thr
65                  70                  75                  80
```

-continued

```
Leu Pro Leu Trp Ala Val Tyr Thr Ala Met Glu Tyr Arg Trp Pro Phe
                85                  90                  95
Gly Asn Tyr Leu Cys Lys Ile Ala Ser Ala Ser Val Ser Phe Asn Leu
            100                 105                 110
Tyr Ala Ser Val Phe Leu Leu Thr Cys Leu Ser Ile Asp Arg Tyr Leu
        115                 120                 125
Ala Ile Val His Pro Met Lys Ser Arg Leu Arg Arg Thr Met Leu Val
130                 135                 140
Ala Lys Val Thr Cys Ile Ile Trp Leu Leu Ala Gly Leu Ala Ser
145                 150                 155                 160
Leu Pro Ala Ile Ile His Arg Asn Val Phe Phe Ile Glu Asn Thr Asn
                165                 170                 175
Ile Thr Val Cys Ala Phe His Tyr Glu Ser Gln Asn Ser Thr Leu Pro
            180                 185                 190
Ile Gly Leu Gly Leu Thr Lys Asn Ile Leu Gly Phe Leu Phe Pro Phe
        195                 200                 205
Leu Ile Ile Leu Thr Ser Tyr Thr Leu Ile Trp Lys Ala Leu Lys Lys
210                 215                 220
Ala Tyr Glu Ile Gln Lys Asn Lys Pro Arg Asn Asp Asp Ile Phe Lys
225                 230                 235                 240
Ile Ile Met Ala Ile Val Leu Phe Phe Phe Ser Trp Ile Pro His
                245                 250                 255
Gln Ile Phe Thr Phe Leu Asp Val Leu Ile Gln Leu Gly Ile Ile Arg
            260                 265                 270
Asp Cys Arg Ile Ala Asp Ile Val Asp Thr Ala Met Pro Ile Thr Ile
        275                 280                 285
Cys Ile Ala Tyr Phe Asn Asn Cys Leu Asn Pro Leu Phe Tyr Gly Phe
290                 295                 300
Leu Gly Lys Lys Phe Lys Arg Tyr Phe Leu Gln Leu Leu Lys Tyr Ile
305                 310                 315                 320
Pro Pro Lys Ala Lys Ser His Ser Asn Leu Ser Thr Lys Met Ser Thr
                325                 330                 335
Leu Ser Tyr Arg Pro Ser Asp Asn Val Ser Ser Ser Thr Lys Lys Pro
            340                 345                 350
Ala Pro Cys Phe Glu Val Glu
        355

<210> SEQ ID NO 67
<211> LENGTH: 27
<212> TYPE: DNA
<213> ORGANISM: Artificial Sequence
<220> FEATURE:
<223> OTHER INFORMATION: Novel Sequence

<400> SEQUENCE: 67
accatgggca gcccctggaa cggcagc                                        27

<210> SEQ ID NO 68
<211> LENGTH: 39
<212> TYPE: DNA
<213> ORGANISM: Artificial Sequence
<220> FEATURE:
<223> OTHER INFORMATION: Novel Sequence

<400> SEQUENCE: 68
agaaccacca ccagcaggac gcggacggtc tgccggtgg                           39
```

```
<210> SEQ ID NO 69
<211> LENGTH: 39
<212> TYPE: DNA
<213> ORGANISM: Artificial Sequence
<220> FEATURE:
<223> OTHER INFORMATION: Novel Sequence

<400> SEQUENCE: 69
gtccgcgtcc tgctggtggt ggttctggca tttataatt                     39

<210> SEQ ID NO 70
<211> LENGTH: 33
<212> TYPE: DNA
<213> ORGANISM: Artificial Sequence
<220> FEATURE:
<223> OTHER INFORMATION: Novel Sequence

<400> SEQUENCE: 70
cctggatcct tatcccatcg tcttcacgtt agc                           33

<210> SEQ ID NO 71
<211> LENGTH: 26
<212> TYPE: DNA
<213> ORGANISM: Artificial Sequence
<220> FEATURE:
<223> OTHER INFORMATION: Novel Sequence

<400> SEQUENCE: 71
ctggaattct cctgccagca tggtga                                   26

<210> SEQ ID NO 72
<211> LENGTH: 30
<212> TYPE: DNA
<213> ORGANISM: Artificial Sequence
<220> FEATURE:
<223> OTHER INFORMATION: Novel Sequence

<400> SEQUENCE: 72
gcaggatcct atattgcgtg ctctgtcccc                               30

<210> SEQ ID NO 73
<211> LENGTH: 999
<212> TYPE: DNA
<213> ORGANISM: Homo sapiens

<400> SEQUENCE: 73
atggtgaact ccacccaccg tgggatgcac acttctctgc acctctggaa ccgcagcagt    60
tacagactgc acagcaatgc cagtgagtcc cttggaaaag ctactctga tggagggtgc    120 tacgagcaac tttttgtctc tcctgaggtg tttgtgactc tgggtgtcat cagcttgttg    180
gagaatatct tagtgattgt ggcaatagcc aagaacaaga atctgcattc acccatgtac    240
tttttcatct gcagcttggc tgtggctgat atgctggtga cgtttcaaa tggatcagaa    300 accattatca tcacccctat taaacagtaca gatacggatg cacagagttt cacagtgaat    360
attgataatg tcattgactc ggtgatctgt agctccttgc ttgcatccat ttgcagcctg    420
ctttcaattg cagtggacag gtactttact atcttctatg ctctccagta ccataacatt    480
atgacagtta agcgggttgg gatcagcata agttgtatct gggcagcttg cacggtttca    540 ggcatttttgt tcatcattta ctcagatagt agtgctgtca tcatctgcct catcaccatg    600
ttcttcacca tgctggctct catggcttct ctctatgtcc acatgttcct gatggccagg    660
cttcacatta gaggattgc tgtcctcccc ggcactggtg ccatccgcca aggtgccaat    720
atgaagggag cgattacctt gaccatcctg attggcgtct tgttgtctg ctgggcccca    780
```

```
ttcttcctcc acttaatatt ctacatctct tgtcctcaga atccatattg tgtgtgcttc    840
atgtctcact ttaacttgta tctcatactg atcatgtgta attcaatcat cgatcctctg    900
atttatgcac tccggagtca agaactgagg aaaaccttca aagagatcat ctgttgctat    960
cccctgggag gcctttgtga cttgtctagc agatattaa                           999
```

<210> SEQ ID NO 74
<211> LENGTH: 332
<212> TYPE: PRT
<213> ORGANISM: Homo sapiens

<400> SEQUENCE: 74

```
Met Val Asn Ser Thr His Arg Gly Met His Thr Ser Leu His Leu Trp
1               5                   10                  15

Asn Arg Ser Ser Tyr Arg Leu His Ser Asn Ala Ser Glu Ser Leu Gly
                20                  25                  30

Lys Gly Tyr Ser Asp Gly Gly Cys Tyr Glu Gln Leu Phe Val Ser Pro
            35                  40                  45

Glu Val Phe Val Thr Leu Gly Val Ile Ser Leu Leu Glu Asn Ile Leu
50                  55                  60

Val Ile Val Ala Ile Ala Lys Asn Lys Asn Leu His Ser Pro Met Tyr
65                  70                  75                  80

Phe Phe Ile Cys Ser Leu Ala Val Ala Asp Met Leu Val Ser Val Ser
                85                  90                  95

Asn Gly Ser Glu Thr Ile Ile Ile Thr Leu Leu Asn Ser Thr Asp Thr
            100                 105                 110

Asp Ala Gln Ser Phe Thr Val Asn Ile Asp Asn Val Ile Asp Ser Val
        115                 120                 125

Ile Cys Ser Ser Leu Leu Ala Ser Ile Cys Ser Leu Leu Ser Ile Ala
130                 135                 140

Val Asp Arg Tyr Phe Thr Ile Phe Tyr Ala Leu Gln Tyr His Asn Ile
145                 150                 155                 160

Met Thr Val Lys Arg Val Gly Ile Ser Ile Ser Cys Ile Trp Ala Ala
                165                 170                 175

Cys Thr Val Ser Gly Ile Leu Phe Ile Ile Tyr Ser Asp Ser Ser Ala
            180                 185                 190

Val Ile Ile Cys Leu Ile Thr Met Phe Phe Thr Met Leu Ala Leu Met
        195                 200                 205

Ala Ser Leu Tyr Val His Met Phe Leu Met Ala Arg Leu His Ile Lys
210                 215                 220

Arg Ile Ala Val Leu Pro Gly Thr Gly Ala Ile Arg Gln Gly Ala Asn
225                 230                 235                 240

Met Lys Gly Ala Ile Thr Leu Thr Ile Leu Ile Gly Val Phe Val Val
                245                 250                 255

Cys Trp Ala Pro Phe Phe Leu His Leu Ile Phe Tyr Ile Ser Cys Pro
            260                 265                 270

Gln Asn Pro Tyr Cys Val Cys Phe Met Ser His Phe Asn Leu Tyr Leu
        275                 280                 285

Ile Leu Ile Met Cys Asn Ser Ile Ile Asp Pro Leu Ile Tyr Ala Leu
290                 295                 300

Arg Ser Gln Glu Leu Arg Lys Thr Phe Lys Glu Ile Ile Cys Cys Tyr
305                 310                 315                 320

Pro Leu Gly Gly Leu Cys Asp Leu Ser Ser Arg Tyr
                325                 330
```

<210> SEQ ID NO 75
<211> LENGTH: 32
<212> TYPE: DNA
<213> ORGANISM: Artificial Sequence
<220> FEATURE:
<223> OTHER INFORMATION: Novel Sequence

<400> SEQUENCE: 75
ccgaagcttc gagctgagta aggcggcggg ct                                  32

<210> SEQ ID NO 76
<211> LENGTH: 31
<212> TYPE: DNA
<213> ORGANISM: Artificial Sequence
<220> FEATURE:
<223> OTHER INFORMATION: Novel Sequence

<400> SEQUENCE: 76
gtggaattca tttgccctgc ctcaaccccc a                                   31

<210> SEQ ID NO 77
<211> LENGTH: 1344
<212> TYPE: DNA
<213> ORGANISM: Homo sapiens

<400> SEQUENCE: 77
atggagctgc taaagctgaa ccggagcgtg cagggaaccg acccgggcc ggggcttcc       60 ctgtgccgcc cggggcgcc tctcctcaac agcagcagtg tgggcaacct cagctgcgag     120
ccccctcgca ttcgcggagc cgggacacga gaattggagc tggccattag aatcactctt   180
tacgcagtga tcttcctgat gagcgttgga ggaaatatgc tcatcatcgt ggtcctggga   240
ctgagccgcc gcctgaggac tgtcaccaat gccttcctcc tctcactggc agtcagcgac   300
ctcctgctgg ctgtggcttg catgcccttc accctcctgc caatctcat gggcacattc    360 atctttggca ccgtcatctg caaggcggtt tcctacctca tgggggtgtc tgtgagtgtg   420
tccacgctaa gcctcgtggc catcgcactg gagcgatata gcgccatctg ccgaccactg   480
caggcacgag tgtggcagac gcgctcccac gcggctcgcg tgattgtagc cacgtggctg   540
ctgtccggac tactcatggt gccctacccc gtgtacactg tcgtgcaacc agtgggcct    600 cgtgtgctgc agtgcgtgca tcgctggccc agtgcgcggg tccgccagac ctggtccgta   660
ctgctgcttc tgctcttgtt cttcatccca ggtgtggtta tggccgtggc ctacggcctt   720
atctctcgcg agctctactt agggcttcgc tttgacggcg acagtgacag cgacagccaa   780
agcagggtcc gaaaccaagg cggctgcca ggggctgttc accagaacgg gcgttgccgg   840
cctgagactg gcgcggttgg caaagacagc gatggctgct acgtgcaact tccacgttcc   900
cggcctgccc tggagctgac ggcgctgacg gctcctgggc cgggatccgg ctcccggccc   960
acccaggcca agctgctggc taagaagcgc gtggtgcgaa tgttgctggt gatcgttgtg  1020
cttttttttc tgtgttggtt gccagtttat agtgccaaca cgtggcgcgc ctttgatggc  1080
ccgggtgcac accagagcact ctcgggtgct cctatctcct tcattcactt gctgagctac  1140
gcctcggcct gtgtcaaccc cctggtctac tgcttcatgc accgtcgctt cgccaggcc   1200 tgcctggaaa cttgcgctcg ctgctgcccc cggcctccac gagctcgccc cagggctctt  1260
cccgatgagg accctcccac tccctccatt gcttcgctgt ccaggcttag ctacaccacc  1320
atcagcacac tgggccctgg ctga                                          1344

<210> SEQ ID NO 78

```
<211> LENGTH: 447
<212> TYPE: PRT
<213> ORGANISM: Homo sapiens

<400> SEQUENCE: 78

Met Glu Leu Leu Lys Leu Asn Arg Ser Val Gln Gly Thr Gly Pro Gly
1               5                   10                  15

Pro Gly Ala Ser Leu Cys Arg Pro Gly Ala Pro Leu Leu Asn Ser Ser
            20                  25                  30

Ser Val Gly Asn Leu Ser Cys Glu Pro Pro Arg Ile Arg Gly Ala Gly
        35                  40                  45

Thr Arg Glu Leu Glu Leu Ala Ile Arg Ile Thr Leu Tyr Ala Val Ile
50                  55                  60

Phe Leu Met Ser Val Gly Gly Asn Met Leu Ile Ile Val Val Leu Gly
65                  70                  75                  80

Leu Ser Arg Arg Leu Arg Thr Val Thr Asn Ala Phe Leu Leu Ser Leu
                85                  90                  95

Ala Val Ser Asp Leu Leu Leu Ala Val Ala Cys Met Pro Phe Thr Leu
            100                 105                 110

Leu Pro Asn Leu Met Gly Thr Phe Ile Phe Gly Thr Val Ile Cys Lys
        115                 120                 125

Ala Val Ser Tyr Leu Met Gly Val Ser Val Ser Val Ser Thr Leu Ser
130                 135                 140

Leu Val Ala Ile Ala Leu Glu Arg Tyr Ser Ala Ile Cys Arg Pro Leu
145                 150                 155                 160

Gln Ala Arg Val Trp Gln Thr Arg Ser His Ala Ala Arg Val Ile Val
                165                 170                 175

Ala Thr Trp Leu Leu Ser Gly Leu Leu Met Val Pro Tyr Pro Val Tyr
            180                 185                 190

Thr Val Val Gln Pro Val Gly Pro Arg Val Leu Gln Cys Val His Arg
        195                 200                 205

Trp Pro Ser Ala Arg Val Arg Gln Thr Trp Ser Val Leu Leu Leu Leu
210                 215                 220

Leu Leu Phe Phe Ile Pro Gly Val Val Met Ala Val Ala Tyr Gly Leu
225                 230                 235                 240

Ile Ser Arg Glu Leu Tyr Leu Gly Leu Arg Phe Asp Gly Asp Ser Asp
                245                 250                 255

Ser Asp Ser Gln Ser Arg Val Arg Asn Gln Gly Gly Leu Pro Gly Ala
            260                 265                 270

Val His Gln Asn Gly Arg Cys Arg Pro Glu Thr Gly Ala Val Gly Lys
        275                 280                 285

Asp Ser Asp Gly Cys Tyr Val Gln Leu Pro Arg Ser Arg Pro Ala Leu
290                 295                 300

Glu Leu Thr Ala Leu Thr Ala Pro Gly Pro Gly Ser Gly Ser Arg Pro
305                 310                 315                 320

Thr Gln Ala Lys Leu Leu Ala Lys Lys Arg Val Val Arg Met Leu Leu
                325                 330                 335

Val Ile Val Val Leu Phe Phe Leu Cys Trp Leu Pro Val Tyr Ser Ala
            340                 345                 350

Asn Thr Trp Arg Ala Phe Asp Gly Pro Gly Ala His Arg Ala Leu Ser
        355                 360                 365

Val Ala Pro Ile Ser Phe Ile His Leu Leu Ser Tyr Ala Ser Ala Cys
370                 375                 380

Val Asn Pro Leu Val Tyr Cys Phe Met His Arg Arg Phe Arg Gln Ala
385                 390                 395                 400
```

```
Cys Leu Glu Thr Cys Ala Arg Cys Cys Pro Arg Pro Arg Ala Arg
            405                 410                 415

Pro Arg Ala Leu Pro Asp Glu Asp Pro Pro Thr Pro Ser Ile Ala Ser
        420                 425                 430

Leu Ser Arg Leu Ser Tyr Thr Thr Ile Ser Thr Leu Gly Pro Gly
        435                 440                 445

<210> SEQ ID NO 79
<211> LENGTH: 30
<212> TYPE: DNA
<213> ORGANISM: Artificial Sequence
<220> FEATURE:
<223> OTHER INFORMATION: Novel Sequence

<400> SEQUENCE: 79
tgcaagctta aaaggaaaaa aatgaacagc                                       30

<210> SEQ ID NO 80
<211> LENGTH: 30
<212> TYPE: DNA
<213> ORGANISM: Artificial Sequence
<220> FEATURE:
<223> OTHER INFORMATION: Novel Sequence

<400> SEQUENCE: 80
taaggatccc ttcccttcaa acatccttg                                        30

<210> SEQ ID NO 81
<211> LENGTH: 1014
<212> TYPE: DNA
<213> ORGANISM: Homo sapiens

<400> SEQUENCE: 81
atgaacagca catgtattga agaacagcat gacctggatc actatttgtt tcccattgtt      60
tacatctttg tgattatagt cagcattcca gccaatattg gatctctgtg tgtgtctttc     120
ctgcaaccca agaaggaaag tgaactagga atttacctct tcagtttgtc actatcagat     180
ttactctatg cattaactct cccttttatgg attgattata cttggaataa agacaactgg    240
actttctctc ctgccttgtg caaagggagt gcttttctca tgtacatgaa gttttacagc     300
agcacagcat tcctcacctg cattgccgtt gatcggtatt ggctgttgt ctaccctttg      360 aagttttttt tcctaaggac aagaagaatt gcactcatgg tcagcctgtc catctggata     420
ttggaaacca tcttcaatgc tgtcatgttg tgggaagatg aaacagttgt tgaatattgc     480
gatgccgaaa agtctaattt tactttatgc tatgacaaat acccttaga gaaatggcaa     540 atcaacctca acttgttcag gacgtgtaca ggctatgcaa taccttggt caccatcctg      600 atctgtaacc ggaaagtcta ccaagctgtg cggcacaata agccacgga aacaaggaa       660 aagaagagaa tcataaaact acttgtcagc atcacagtta cttttgtctt atgctttact     720 cccttcatg tgatgttgct gattcgctgc attttagagc atgctgtgaa cttcgaagac      780
cacagcaatt ctgggaagcg aacttacaca atgtatagaa tcacggttgc attaacaagt     840
ttaaattgtg ttgctgatcc aattctgtac tgttttgtta ccgaaacagg aagatatgat     900
atgtggaata tattaaaatt ctgcactggg aggtgtaata catcacaaag acaagaaaa      960 cgcatacttt ctgtgtctac aaaagatact atggaattag aggtccttga gtag          1014

<210> SEQ ID NO 82
<211> LENGTH: 337
<212> TYPE: PRT
```

<213> ORGANISM: Homo sapiens

<400> SEQUENCE: 82

```
Met Asn Ser Thr Cys Ile Glu Glu Gln His Asp Leu Asp His Tyr Leu
1               5                   10                  15
Phe Pro Ile Val Tyr Ile Phe Val Ile Val Ser Ile Pro Ala Asn
            20                  25                  30
Ile Gly Ser Leu Cys Val Ser Phe Leu Gln Pro Lys Lys Glu Ser Glu
        35                  40                  45
Leu Gly Ile Tyr Leu Phe Ser Leu Ser Leu Ser Asp Leu Leu Tyr Ala
    50                  55                  60
Leu Thr Leu Pro Leu Trp Ile Asp Tyr Thr Trp Asn Lys Asp Asn Trp
65                  70                  75                  80
Thr Phe Ser Pro Ala Leu Cys Lys Gly Ser Ala Phe Leu Met Tyr Met
                85                  90                  95
Lys Phe Tyr Ser Ser Thr Ala Phe Leu Thr Cys Ile Ala Val Asp Arg
            100                 105                 110
Tyr Leu Ala Val Val Tyr Pro Leu Lys Phe Phe Leu Arg Thr Arg
        115                 120                 125
Arg Ile Ala Leu Met Val Ser Leu Ser Ile Trp Ile Leu Glu Thr Ile
    130                 135                 140
Phe Asn Ala Val Met Leu Trp Glu Asp Glu Thr Val Val Glu Tyr Cys
145                 150                 155                 160
Asp Ala Glu Lys Ser Asn Phe Thr Leu Cys Tyr Asp Lys Tyr Pro Leu
                165                 170                 175
Glu Lys Trp Gln Ile Asn Leu Asn Leu Phe Arg Thr Cys Thr Gly Tyr
            180                 185                 190
Ala Ile Pro Leu Val Thr Ile Leu Ile Cys Asn Arg Lys Val Tyr Gln
        195                 200                 205
Ala Val Arg His Asn Lys Ala Thr Glu Asn Lys Glu Lys Lys Arg Ile
    210                 215                 220
Ile Lys Leu Leu Val Ser Ile Thr Val Thr Phe Val Leu Cys Phe Thr
225                 230                 235                 240
Pro Phe His Val Met Leu Leu Ile Arg Cys Ile Leu Glu His Ala Val
                245                 250                 255
Asn Phe Gly Asp His Ser Asn Ser Gly Lys Arg Thr Tyr Thr Met Tyr
            260                 265                 270
Arg Ile Thr Val Ala Leu Thr Ser Leu Asn Cys Val Ala Asp Pro Ile
        275                 280                 285
Leu Tyr Cys Phe Val Thr Glu Thr Gly Arg Tyr Asp Met Trp Asn Ile
    290                 295                 300
Leu Lys Phe Cys Thr Gly Arg Cys Asn Thr Ser Gln Arg Gln Arg Lys
305                 310                 315                 320
Arg Ile Leu Ser Val Ser Thr Lys Asp Thr Met Glu Leu Glu Val Leu
                325                 330                 335
Glu
```

<210> SEQ ID NO 83
<211> LENGTH: 40
<212> TYPE: DNA
<213> ORGANISM: Artificial Sequence
<220> FEATURE:
<223> OTHER INFORMATION: Novel Sequence

<400> SEQUENCE: 83
caggaagaag aaacgagctg tcattatgat ggtgacagtg        40

<210> SEQ ID NO 84
<211> LENGTH: 40
<212> TYPE: DNA
<213> ORGANISM: Artificial Sequence
<220> FEATURE:
<223> OTHER INFORMATION: Novel Sequence

<400> SEQUENCE: 84
cactgtcacc atcataatga cagctcgttt cttcttcctg            40

<210> SEQ ID NO 85
<211> LENGTH: 30
<212> TYPE: DNA
<213> ORGANISM: Artificial Sequence
<220> FEATURE:
<223> OTHER INFORMATION: Novel Sequence

<400> SEQUENCE: 85
ggccaccggc agaccaaacg cgtcctgctg                       30

<210> SEQ ID NO 86
<211> LENGTH: 31
<212> TYPE: DNA
<213> ORGANISM: Artificial Sequence
<220> FEATURE:
<223> OTHER INFORMATION: Novel Sequence

<400> SEQUENCE: 86
ctccttcggt cctcctatcg ttgtcagaag t                     31

<210> SEQ ID NO 87
<211> LENGTH: 37
<212> TYPE: DNA
<213> ORGANISM: Artificial Sequence
<220> FEATURE:
<223> OTHER INFORMATION: Novel Sequence

<400> SEQUENCE: 87
ggaaaagaag agaatcaaaa aactacttgt cagcatc                37

<210> SEQ ID NO 88
<211> LENGTH: 31
<212> TYPE: DNA
<213> ORGANISM: Artificial Sequence
<220> FEATURE:
<223> OTHER INFORMATION: Novel Sequence

<400> SEQUENCE: 88
ctccttcggt cctcctatcg ttgtcagaag t                     31

<210> SEQ ID NO 89
<211> LENGTH: 1080
<212> TYPE: DNA
<213> ORGANISM: Homo sapiens

<400> SEQUENCE: 89
atgattctca actcttctac tgaagatggt attaaaagaa tccaagatga ttgtcccaaa      60
gctggaaggc ataattacat atttgtcatg attcctactt tatacagtat catctttgtg     120
gtgggaatat ttggaaacag cttggtggtg atagtcattt acttttatat gaagctgaag     180
actgtggcca gtgttttttct tttgaattta gcactggctg acttatgctt tttactgact    240
ttgccactat gggctgtcta cacagctatg gaataccgct ggccctttgg caattaccta    300
tgtaagattg cttcagccag cgtcagtttc aacctgtacg ctagtgtgtt tctactcacg     360

-continued

```
tgtctcagca ttgatcgata cctggctatt gttcacccaa tgaagtcccg ccttcgacgc    420
acaatgcttg tagccaaagt cacctgcatc atcatttggc tgctggcagg cttggccagt    480
ttgccagcta taatccatcg aaatgtattt tcattgaga caccaatat tacagtttgt      540 gctttccatt atgagtccca aaattcaacc cttccgatag ggctgggcct gaccaaaaat    600
atactgggtt cctgtttcc ttttctgatc attcttacaa gttatactct tatttggaag    660
gccctaaaga aggcttatga aattcagaag aacaaaccaa gaaatgatga tattaaaaag    720
ataattatgg caattgtgct tttcttttc ttttcctgga ttccccacca aatattcact     780
tttctggatg tattgattca actaggcatc atacgtgact gtagaattgc agatattgtg    840
gacacggcca tgcctatcac catttgtata gcttatttta caattgcct gaatcctctt     900 ttttatggct ttctggggaa aaaatttaaa agatattttc tccagcttct aaaatatatt    960
cccccaaaag ccaaatccca ctcaaacctt tcaacaaaaa tgagcacgct ttcctaccgc   1020
ccctcagata atgtaagctc atccaccaag aagcctgcac catgttttga ggttgagtga   1080
```

<210> SEQ ID NO 90
<211> LENGTH: 359
<212> TYPE: PRT
<213> ORGANISM: Homo sapiens

<400> SEQUENCE: 90

```
Met Ile Leu Asn Ser Ser Thr Glu Asp Gly Ile Lys Arg Ile Gln Asp
1               5                   10                  15

Asp Cys Pro Lys Ala Gly Arg His Asn Tyr Ile Phe Val Met Ile Pro
            20                  25                  30

Thr Leu Tyr Ser Ile Ile Phe Val Val Gly Ile Phe Gly Asn Ser Leu
        35                  40                  45

Val Val Ile Val Ile Tyr Phe Tyr Met Lys Leu Lys Thr Val Ala Ser
    50                  55                  60

Val Phe Leu Leu Asn Leu Ala Leu Ala Asp Leu Cys Phe Leu Leu Thr
65                  70                  75                  80

Leu Pro Leu Trp Ala Val Tyr Thr Ala Met Glu Tyr Arg Trp Pro Phe
                85                  90                  95

Gly Asn Tyr Leu Cys Lys Ile Ala Ser Ala Ser Val Ser Phe Asn Leu
            100                 105                 110

Tyr Ala Ser Val Phe Leu Leu Thr Cys Leu Ser Ile Asp Arg Tyr Leu
        115                 120                 125

Ala Ile Val His Pro Met Lys Ser Arg Leu Arg Arg Thr Met Leu Val
    130                 135                 140

Ala Lys Val Thr Cys Ile Ile Ile Trp Leu Leu Ala Gly Leu Ala Ser
145                 150                 155                 160

Leu Pro Ala Ile Ile His Arg Asn Val Phe Phe Ile Glu Asn Thr Asn
                165                 170                 175

Ile Thr Val Cys Ala Phe His Tyr Glu Ser Gln Asn Ser Thr Leu Pro
            180                 185                 190

Ile Gly Leu Gly Leu Thr Lys Asn Ile Leu Gly Phe Leu Phe Pro Phe
        195                 200                 205

Leu Ile Ile Leu Thr Ser Tyr Thr Leu Ile Trp Lys Ala Leu Lys Lys
    210                 215                 220

Ala Tyr Glu Ile Gln Lys Asn Lys Pro Arg Asn Asp Asp Ile Lys Lys
225                 230                 235                 240

Ile Ile Met Ala Ile Val Leu Phe Phe Phe Phe Ser Trp Ile Pro His
                245                 250                 255
```

Gln Ile Phe Thr Phe Leu Asp Val Leu Ile Gln Leu Gly Ile Ile Arg
            260                 265                 270

Asp Cys Arg Ile Ala Asp Ile Val Asp Thr Ala Met Pro Ile Thr Ile
        275                 280                 285

Cys Ile Ala Tyr Phe Asn Asn Cys Leu Asn Pro Leu Phe Tyr Gly Phe
    290                 295                 300

Leu Gly Lys Lys Phe Lys Arg Tyr Phe Leu Gln Leu Leu Lys Tyr Ile
305                 310                 315                 320

Pro Pro Lys Ala Lys Ser His Ser Asn Leu Ser Thr Lys Met Ser Thr
                325                 330                 335

Leu Ser Tyr Arg Pro Ser Asp Asn Val Ser Ser Thr Lys Lys Pro
            340                 345                 350

Ala Pro Cys Phe Glu Val Glu
        355

<210> SEQ ID NO 91
<211> LENGTH: 35
<212> TYPE: DNA
<213> ORGANISM: Artificial Sequence
<220> FEATURE:
<223> OTHER INFORMATION: Novel Sequence

<400> SEQUENCE: 91
ccaagaaatg atgatattaa aaagataatt atggc                                35

<210> SEQ ID NO 92
<211> LENGTH: 31
<212> TYPE: DNA
<213> ORGANISM: Artificial Sequence
<220> FEATURE:
<223> OTHER INFORMATION: Novel Sequence

<400> SEQUENCE: 92
ctccttcggt cctcctatcg ttgtcagaag t                                    31

<210> SEQ ID NO 93
<211> LENGTH: 1080
<212> TYPE: DNA
<213> ORGANISM: Homo sapiens

<400> SEQUENCE: 93
atgattctca actcttctac tgaagatggt attaaaagaa tccaagatga ttgtcccaaa      60
gctggaaggc ataattacat atttgtcatg attcctactt tatacagtat catctttgtg     120
gtgggaatat ttggaaacag cttggtggtg atagtcattt acttttatat gaagctgaag     180
actgtggcca gtgtttttct tttgaattta gcactggctg acttatgctt tttactgact     240
ttgccactat gggctgtcta cacagctatg aataccgct ggcccttggg caattaccta      300
tgtaagattg cttcagccag cgtcagtttc gccctgtacg ctagtgtgtt tctactcacg     360
tgtctcagca ttgatcgata cctggctatt gttcacccaa tgaagtcccg ccttcgacgc     420
acaatgcttg tagccaaagt cacctgcatc atcatttggc tgctggcagg cttggccagt     480
ttgccagcta taatccatcg aaatgtattt ttcattgaga acaccaatat tacagtttgt     540
gctttccatt atgagtccca aaattcaacc cttccgatag ggctgggcct gaccaaaaat     600
atactgggtt tcctgtttcc ttttctgatc attcttacaa gttatactct tatttggaag     660
gccctaaaga aggcttatga aattcagaag aacaaaccaa gaatgatga tatttttaag     720 ataattatgg caattgtgct tttctttttc ttttcctgga ttccccacca atattcact      780

-continued

```
tttctggatg tattgattca actaggcatc atacgtgact gtagaattgc agatattgtg    840
gacacggcca tgcctatcac catttgtata gcttatttta acaattgcct gaatcctctt    900
ttttatggct ttctggggaa aaatttaaa agatattttc tccagcttct aaaatatatt     960
cccccaaaag ccaaatccca ctcaaacctt tcaacaaaaa tgagcacgct ttcctaccgc   1020
ccctcagata atgtaagctc atccaccaag aagcctgcac catgttttga ggttgagtga   1080
```

<210> SEQ ID NO 94
<211> LENGTH: 359
<212> TYPE: PRT
<213> ORGANISM: Homo sapiens

<400> SEQUENCE: 94

```
Met Ile Leu Asn Ser Ser Thr Glu Asp Gly Ile Lys Arg Ile Gln Asp
1               5                  10                  15

Asp Cys Pro Lys Ala Gly Arg His Asn Tyr Ile Phe Val Met Ile Pro
                20                  25                  30

Thr Leu Tyr Ser Ile Ile Phe Val Gly Ile Phe Gly Asn Ser Leu
            35                  40                  45

Val Val Ile Val Ile Tyr Phe Tyr Met Lys Leu Lys Thr Val Ala Ser
50                  55                  60

Val Phe Leu Leu Asn Leu Ala Leu Ala Asp Leu Cys Phe Leu Leu Thr
65                  70                  75                  80

Leu Pro Leu Trp Ala Val Tyr Thr Ala Met Glu Tyr Arg Trp Pro Phe
                85                  90                  95

Gly Asn Tyr Leu Cys Lys Ile Ala Ser Ala Ser Val Ser Phe Ala Leu
            100                 105                 110

Tyr Ala Ser Val Phe Leu Leu Thr Cys Leu Ser Ile Asp Arg Tyr Leu
        115                 120                 125

Ala Ile Val His Pro Met Lys Ser Arg Leu Arg Arg Thr Met Leu Val
130                 135                 140

Ala Lys Val Thr Cys Ile Ile Ile Trp Leu Leu Ala Gly Leu Ala Ser
145                 150                 155                 160

Leu Pro Ala Ile Ile His Arg Asn Val Phe Phe Ile Glu Asn Thr Asn
                165                 170                 175

Ile Thr Val Cys Ala Phe His Tyr Glu Ser Gln Asn Ser Thr Leu Pro
            180                 185                 190

Ile Gly Leu Gly Leu Thr Lys Asn Ile Leu Gly Phe Leu Phe Pro Phe
        195                 200                 205

Leu Ile Ile Leu Thr Ser Tyr Thr Leu Ile Trp Lys Ala Leu Lys Lys
210                 215                 220

Ala Tyr Glu Ile Gln Lys Asn Lys Pro Arg Asn Asp Asp Ile Phe Lys
225                 230                 235                 240

Ile Ile Met Ala Ile Val Leu Phe Phe Phe Ser Trp Ile Pro His
                245                 250                 255

Gln Ile Phe Thr Phe Leu Asp Val Leu Ile Gln Leu Gly Ile Ile Arg
            260                 265                 270

Asp Cys Arg Ile Ala Asp Ile Val Asp Thr Ala Met Pro Ile Thr Ile
        275                 280                 285

Cys Ile Ala Tyr Phe Asn Asn Cys Leu Asn Pro Leu Phe Tyr Gly Phe
290                 295                 300

Leu Gly Lys Lys Phe Lys Arg Tyr Phe Leu Gln Leu Leu Lys Tyr Ile
305                 310                 315                 320

Pro Pro Lys Ala Lys Ser His Ser Asn Leu Ser Thr Lys Met Ser Thr
                325                 330                 335
```

Leu Ser Tyr Arg Pro Ser Asp Asn Val Ser Ser Ser Thr Lys Lys Pro
            340                 345                 350

Ala Pro Cys Phe Glu Val Glu
        355

<210> SEQ ID NO 95
<211> LENGTH: 26
<212> TYPE: DNA
<213> ORGANISM: Artificial Sequence
<220> FEATURE:
<223> OTHER INFORMATION: Novel Sequence

<400> SEQUENCE: 95
cccaagcttc cccaggtgta tttgat                                        26

<210> SEQ ID NO 96
<211> LENGTH: 29
<212> TYPE: DNA
<213> ORGANISM: Artificial Sequence
<220> FEATURE:
<223> OTHER INFORMATION: Novel Sequence

<400> SEQUENCE: 96
cctgcaggcg aaactgactc tggctgaag                                     29

<210> SEQ ID NO 97
<211> LENGTH: 42
<212> TYPE: DNA
<213> ORGANISM: Artificial Sequence
<220> FEATURE:
<223> OTHER INFORMATION: Novel Sequence

<400> SEQUENCE: 97
ctgtacgcta gtgtgtttct actcacgtgt ctcagcattg at                      42

<210> SEQ ID NO 98
<211> LENGTH: 26
<212> TYPE: DNA
<213> ORGANISM: Artificial Sequence
<220> FEATURE:
<223> OTHER INFORMATION: Novel Sequence

<400> SEQUENCE: 98
gttggatcca cataatgcat tttctc                                        26

<210> SEQ ID NO 99
<211> LENGTH: 1080
<212> TYPE: DNA
<213> ORGANISM: Homo sapiens

<400> SEQUENCE: 99
atgattctca actcttctac tgaagatggt attaaaagaa tccaagatga ttgtcccaaa    60
gctggaaggc ataattacat atttgtcatg attcctactt tatacagtat catctttgtg   120
gtgggaatat ttggaaacag cttggtggtg atagtcattt acttttatat gaagctgaag   180
actgtggcca gtgttttttct tttgaattta gcactggctg acttatgctt tttactgact   240
ttgccactat gggctgtcta cacagctatg gaataccgct ggcccttttgg caattaccta   300 tgtaagattg cttcagccag cgtcagtttc aacctgtacg ctagtgtgtt tctactcacg   360
tgtctcagca ttgatcgata cctggctatt gttcacccaa tgaagtcccg ccttcgacgc   420
acaatgcttg tagccaaagt cacctgcatc atcatttggc tgctggcagg cttggccagt   480
ttgccagcta taatccatcg aaatgtattt ttcattgaga acaccaatat tacagtttgt   540

```
gctttccatt atgagtccca aaattcaacc cttccgatag ggctgggcct gaccaaaaat    600
atactgggtt tcctgtttcc ttttctgatc attcttacaa gttattttgg aattcgaaaa    660
cacttactga agacgaatag ctatgggaag aacaggataa cccgtgacca agttaagaag    720
ataattatgg caattgtgct tttctttttc ttttcctgga ttccccacca aatattcact    780
tttctggatg tatgattca  actaggcatc atacgtgact gtagaattgc agatattgtg    840
gacacggcca tgcctatcac catttgtata gcttatttta caattgcctg aatcctctt     900 ttttatggct ttctggggaa aaatttaaa agatattttc tccagcttct aaaatatatt     960 ccccaaaag ccaaatccca ctcaaacctt tcaacaaaaa tgagcacgct ttcctaccgc    1020
ccctcagata atgtaagctc atccaccaag aagcctgcac catgttttga ggttgagtga  1080
```

<210> SEQ ID NO 100
<211> LENGTH: 359
<212> TYPE: PRT
<213> ORGANISM: Homo sapiens

<400> SEQUENCE: 100

```
Met Ile Leu Asn Ser Ser Thr Glu Asp Gly Ile Lys Arg Ile Gln Asp
1               5                   10                  15

Asp Cys Pro Lys Ala Gly Arg His Asn Tyr Ile Phe Val Met Ile Pro
            20                  25                  30

Thr Leu Tyr Ser Ile Ile Phe Val Gly Ile Phe Gly Asn Ser Leu
        35                  40                  45

Val Val Ile Val Ile Tyr Phe Tyr Met Lys Leu Lys Thr Val Ala Ser
50                  55                  60

Val Phe Leu Leu Asn Leu Ala Leu Ala Asp Leu Cys Phe Leu Leu Thr
65                  70                  75                  80

Leu Pro Leu Trp Ala Val Tyr Thr Ala Met Glu Tyr Arg Trp Pro Phe
                85                  90                  95

Gly Asn Tyr Leu Cys Lys Ile Ala Ser Ala Ser Val Ser Phe Asn Leu
            100                 105                 110

Tyr Ala Ser Val Phe Leu Leu Thr Cys Leu Ser Ile Asp Arg Tyr Leu
        115                 120                 125

Ala Ile Val His Pro Met Lys Ser Arg Leu Arg Arg Thr Met Leu Val
130                 135                 140

Ala Lys Val Thr Cys Ile Ile Ile Trp Leu Leu Ala Gly Leu Ala Ser
145                 150                 155                 160

Leu Pro Ala Ile Ile His Arg Asn Val Phe Phe Ile Glu Asn Thr Asn
                165                 170                 175

Ile Thr Val Cys Ala Phe His Tyr Glu Ser Gln Asn Ser Thr Leu Pro
            180                 185                 190

Ile Gly Leu Gly Leu Thr Lys Asn Ile Leu Gly Phe Leu Phe Pro Phe
        195                 200                 205

Leu Ile Ile Leu Thr Ser Tyr Phe Gly Ile Arg Lys His Leu Leu Lys
210                 215                 220

Thr Asn Ser Tyr Gly Lys Asn Arg Ile Thr Arg Asp Gln Val Lys Lys
225                 230                 235                 240

Ile Ile Met Ala Ile Val Leu Phe Phe Phe Ser Trp Ile Pro His
                245                 250                 255

Gln Ile Phe Thr Phe Leu Asp Val Leu Ile Gln Leu Gly Ile Ile Arg
            260                 265                 270

Asp Cys Arg Ile Ala Asp Ile Val Asp Thr Ala Met Pro Ile Thr Ile
        275                 280                 285
```

```
Cys Ile Ala Tyr Phe Asn Asn Cys Leu Asn Pro Leu Phe Tyr Gly Phe
    290                 295                 300

Leu Gly Lys Lys Phe Lys Arg Tyr Phe Leu Gln Leu Leu Lys Tyr Ile
305                 310                 315                 320

Pro Pro Lys Ala Lys Ser His Ser Asn Leu Ser Thr Lys Met Ser Thr
                325                 330                 335

Leu Ser Tyr Arg Pro Ser Asp Asn Val Ser Ser Thr Lys Lys Pro
            340                 345                 350

Ala Pro Cys Phe Glu Val Glu
        355

<210> SEQ ID NO 101
<211> LENGTH: 37
<212> TYPE: DNA
<213> ORGANISM: Artificial Sequence
<220> FEATURE:
<223> OTHER INFORMATION: Novel Sequence

<400> SEQUENCE: 101
tccgaattcc aaaataactt gtaagaatga tcagaaa                              37

<210> SEQ ID NO 102
<211> LENGTH: 33
<212> TYPE: DNA
<213> ORGANISM: Artificial Sequence
<220> FEATURE:
<223> OTHER INFORMATION: Novel Sequence

<400> SEQUENCE: 102
agatcttaag aagataatta tggcaattgt gct                                  33

<210> SEQ ID NO 103
<211> LENGTH: 62
<212> TYPE: DNA
<213> ORGANISM: Artificial Sequence
<220> FEATURE:
<223> OTHER INFORMATION: Novel Sequence

<400> SEQUENCE: 103
aattcgaaaa cacttactga agacgaatag ctatgggaag aacaggataa cccgtgacca    60
ag                                                                    62

<210> SEQ ID NO 104
<211> LENGTH: 62
<212> TYPE: DNA
<213> ORGANISM: Artificial Sequence
<220> FEATURE:
<223> OTHER INFORMATION: Novel Sequence

<400> SEQUENCE: 104
ttaacttggt cacgggttat cctgttcttc ccatagctat tcgtcttcag taagtgtttt    60
cg                                                                    62

<210> SEQ ID NO 105
<211> LENGTH: 1083
<212> TYPE: DNA
<213> ORGANISM: Homo sapiens

<400> SEQUENCE: 105
atgattctca actcttctac tgaagatggt attaaaagaa tccaagatga ttgtcccaaa    60
gctggaaggc ataattacat atttgtcatg attcctactt tatacagtat catctttgtg   120
```

-continued

```
gtgggaatat ttggaaacag cttggtggtg atagtcattt acttttatat gaagctgaag    180
actgtggcca gtgttttct  tttgaattta gcactggctg acttatgctt tttactgact    240
ttgccactat gggctgtcta cacagctatg aataccgct  ggcccttgg  caattaccta    300
tgtaagattg cttcagccag cgtcagtttc aacctgtacg ctagtgtgtt tctactcacg    360
tgtctcagca ttgatcgata cctggctatt gttcacccaa tgaagtcccg ccttcgacgc    420
acaatgcttg tagccaaagt cacctgcatc atcatttggc tgctggcagg cttggccagt    480
ttgccagcta taatccatcg aaatgtattt tcattgaga  acaccaatat tacagtttgt    540
gctttccatt atgagtccca aaattcaacc cttccgatag ggctgggcct gaccaaaaat    600
atactgggtt tcctgtttcc ttttctgatc attcttacaa gttatactct tatttggaag    660
gccctaaaga aggcttatga aattcagaag aacaaaccaa gaaatgatga tatttttaag    720
ataattatgg cagcaattgt gcttttcttt ttcttttcct ggattcccca ccaaatattc    780
acttttctgg atgtattgat tcaactaggc atcatacgtg actgtagaat tgcagatatt    840
gtggacacgg ccatgcctat caccatttgt atagcttatt ttaacaattg cctgaatcct    900
cttttttatg gctttctggg gaaaaaattt aaaagatatt ttctccagct tctaaaatat    960
attccccaa  aagccaaatc ccactcaaac ctttcaacaa aaatgagcac gctttcctac    1020
cgcccctcag ataatgtaag ctcatccacc aagaagcctg caccatgttt tgaggttgag    1080
tga                                                                  1083
```

<210> SEQ ID NO 106
<211> LENGTH: 360
<212> TYPE: PRT
<213> ORGANISM: Homo sapiens

<400> SEQUENCE: 106

```
Met Ile Leu Asn Ser Ser Thr Glu Asp Gly Ile Lys Arg Ile Gln Asp
1               5                   10                  15

Asp Cys Pro Lys Ala Gly Arg His Asn Tyr Ile Phe Val Met Ile Pro
                20                  25                  30

Thr Leu Tyr Ser Ile Ile Phe Val Val Gly Ile Phe Gly Asn Ser Leu
            35                  40                  45

Val Val Ile Val Ile Tyr Phe Tyr Met Lys Leu Lys Thr Val Ala Ser
        50                  55                  60

Val Phe Leu Leu Asn Leu Ala Leu Ala Asp Leu Cys Phe Leu Leu Thr
65                  70                  75                  80

Leu Pro Leu Trp Ala Val Tyr Thr Ala Met Glu Tyr Arg Trp Pro Phe
                85                  90                  95

Gly Asn Tyr Leu Cys Lys Ile Ala Ser Ala Ser Val Ser Phe Asn Leu
            100                 105                 110

Tyr Ala Ser Val Phe Leu Leu Thr Cys Leu Ser Ile Asp Arg Tyr Leu
        115                 120                 125

Ala Ile Val His Pro Met Lys Ser Arg Leu Arg Arg Thr Met Leu Val
    130                 135                 140

Ala Lys Val Thr Cys Ile Ile Ile Trp Leu Leu Ala Gly Leu Ala Ser
145                 150                 155                 160

Leu Pro Ala Ile Ile His Arg Asn Val Phe Phe Ile Glu Asn Thr Asn
                165                 170                 175

Ile Thr Val Cys Ala Phe His Tyr Glu Ser Gln Asn Ser Thr Leu Pro
            180                 185                 190

Ile Gly Leu Gly Leu Thr Lys Asn Ile Leu Gly Phe Leu Phe Pro Phe
        195                 200                 205
```

```
Leu Ile Ile Leu Thr Ser Tyr Thr Leu Ile Trp Lys Ala Leu Lys Lys
    210                 215                 220

Ala Tyr Glu Ile Gln Lys Asn Lys Pro Arg Asn Asp Asp Ile Phe Lys
225                 230                 235                 240

Ile Ile Met Ala Ala Ile Val Leu Phe Phe Phe Ser Trp Ile Pro
                245                 250                 255

His Gln Ile Phe Thr Phe Leu Asp Val Leu Ile Gln Leu Gly Ile Ile
        260                 265                 270

Arg Asp Cys Arg Ile Ala Asp Ile Val Asp Thr Ala Met Pro Ile Thr
            275                 280                 285

Ile Cys Ile Ala Tyr Phe Asn Asn Cys Leu Asn Pro Leu Phe Tyr Gly
        290                 295                 300

Phe Leu Gly Lys Lys Phe Lys Arg Tyr Phe Leu Gln Leu Leu Lys Tyr
305                 310                 315                 320

Ile Pro Pro Lys Ala Lys Ser His Ser Asn Leu Ser Thr Lys Met Ser
                325                 330                 335

Thr Leu Ser Tyr Arg Pro Ser Asp Asn Val Ser Ser Ser Thr Lys Lys
            340                 345                 350

Pro Ala Pro Cys Phe Glu Val Glu
            355                 360

<210> SEQ ID NO 107
<211> LENGTH: 26
<212> TYPE: DNA
<213> ORGANISM: Artificial Sequence
<220> FEATURE:
<223> OTHER INFORMATION: Novel Sequence

<400> SEQUENCE: 107
cccaagcttc cccaggtgta tttgat                                          26

<210> SEQ ID NO 108
<211> LENGTH: 38
<212> TYPE: DNA
<213> ORGANISM: Artificial Sequence
<220> FEATURE:
<223> OTHER INFORMATION: Novel Sequence

<400> SEQUENCE: 108
aagcacaatt gctgcataat tatcttaaaa atatcatc                             38

<210> SEQ ID NO 109
<211> LENGTH: 39
<212> TYPE: DNA
<213> ORGANISM: Artificial Sequence
<220> FEATURE:
<223> OTHER INFORMATION: Novel Sequence

<400> SEQUENCE: 109
aagataatta tggcagcaat tgtgcttttc ttttctttt                            39

<210> SEQ ID NO 110
<211> LENGTH: 26
<212> TYPE: DNA
<213> ORGANISM: Artificial Sequence
<220> FEATURE:
<223> OTHER INFORMATION: Novel Sequence

<400> SEQUENCE: 110
gttggatcca cataatgcat tttctc                                          26
```

<210> SEQ ID NO 111
<211> LENGTH: 1344
<212> TYPE: DNA
<213> ORGANISM: Homo sapiens

<400> SEQUENCE: 111

```
atggagctgc taaagctgaa ccggagcgtg cagggaaccg acccgggcc gggggcttcc      60
ctgtgccgcc cggggcgcc tctcctcaac agcagcagtg tgggcaacct cagctgcgag     120
cccctcgca ttcgcggagc cgggacacga gaattggagc tggccattag aatcactctt     180
tacgcagtga tcttcctgat gagcgttgga ggaaatatgc tcatcatcgt ggtcctggga     240
ctgagccgcc gcctgaggac tgtcaccaat gccttcctcc tctcactggc agtcagcgac     300
ctcctgctgg ctgtggcttg catgcccttc accctcctgc caatctcat gggcacattc      360
atctttggca ccgtcatctg caaggcggtt tcctacctca tggggtgtc tgtgagtgtg     420
tccacgctaa gcctcgtggc catcgcactg gagcgatata gcgccatctg ccgaccactg     480
caggcacgag tgtggcagac gcgctcccac gcggctcgcg tgattgtagc cacgtggctg     540
ctgtccggac tactcatggt gccctacccc gtgtacactg tcgtgcaacc agtggggcct     600
cgtgtgctgc agtgcgtgca tcgctggccc agtgcgcggg tccgccagac ctggtccgta     660
ctgctgcttc tgctcttgtt cttcatccca ggtgtggtta tggccgtggc ctacgggctt     720
atctctcgcg agctctactt agggcttcgc tttgacggcg acagtgacag cgacagccaa     780
agcagggtcc gaaaccaagg cggctgcca ggggctgttc accagaacgg cgttgccgg      840
cctgagactg cgcggttgg caaagacagc gatggctgct acgtgcaact tccacgttcc     900
cggcctgccc tggagctgac ggcgctgacg gctcctgggc cgggatccgg ctcccggccc     960
acccaggcca agctgctggc taagaagcgc gtgaaacgaa tgttgctggt gatcgttgtg    1020
cttttttttc tgtgttggtt gccagtttat agtgccaaca cgtggcgcgc ctttgatggc    1080
ccgggtgcac accgagcact ctcgggtgct cctatctcct tcattcactt gctgagctac    1140
gcctcggcct gtgtcaaccc cctggtctac tgcttcatgc accgtcgctt tcgccaggcc    1200
tgcctggaaa cttgcgctcg ctgctgcccc cggcctccac gagctcgccc cagggctctt    1260
cccgatgagg accctcccac tccctccatt gcttcgctgt ccaggcttag ctacaccacc    1320
atcagcacac tgggccctgg ctga                                           1344
```

<210> SEQ ID NO 112
<211> LENGTH: 447
<212> TYPE: PRT
<213> ORGANISM: Homo sapiens

<400> SEQUENCE: 112

```
Met Glu Leu Leu Lys Leu Asn Arg Ser Val Gln Gly Thr Gly Pro Gly
1               5                   10                  15

Pro Gly Ala Ser Leu Cys Arg Pro Gly Ala Pro Leu Leu Asn Ser Ser
            20                  25                  30

Ser Val Gly Asn Leu Ser Cys Glu Pro Pro Arg Ile Arg Gly Ala Gly
        35                  40                  45

Thr Arg Glu Leu Glu Leu Ala Ile Arg Ile Thr Leu Tyr Ala Val Ile
    50                  55                  60

Phe Leu Met Ser Val Gly Gly Asn Met Leu Ile Ile Val Val Leu Gly
65                  70                  75                  80

Leu Ser Arg Arg Leu Arg Thr Val Thr Asn Ala Phe Leu Leu Ser Leu
                85                  90                  95

Ala Val Ser Asp Leu Leu Leu Ala Val Ala Cys Met Pro Phe Thr Leu
```

```
            100                 105                 110
Leu Pro Asn Leu Met Gly Thr Phe Ile Phe Gly Thr Val Ile Cys Lys
        115                 120                 125

Ala Val Ser Tyr Leu Met Gly Val Ser Val Ser Val Ser Thr Leu Ser
    130                 135                 140

Leu Val Ala Ile Ala Leu Glu Arg Tyr Ser Ala Ile Cys Arg Pro Leu
145                 150                 155                 160

Gln Ala Arg Val Trp Gln Thr Arg Ser His Ala Ala Arg Val Ile Val
                165                 170                 175

Ala Thr Trp Leu Leu Ser Gly Leu Leu Met Val Pro Tyr Pro Val Tyr
            180                 185                 190

Thr Val Val Gln Pro Val Gly Pro Arg Val Leu Gln Cys Val His Arg
            195                 200                 205

Trp Pro Ser Ala Arg Val Arg Gln Thr Trp Ser Val Leu Leu Leu Leu
        210                 215                 220

Leu Leu Phe Phe Ile Pro Gly Val Val Met Ala Val Ala Tyr Gly Leu
225                 230                 235                 240

Ile Ser Arg Glu Leu Tyr Leu Gly Leu Arg Phe Asp Gly Asp Ser Asp
                245                 250                 255

Ser Asp Ser Gln Ser Arg Val Arg Asn Gln Gly Gly Leu Pro Gly Ala
            260                 265                 270

Val His Gln Asn Gly Arg Cys Arg Pro Glu Thr Gly Ala Val Gly Lys
            275                 280                 285

Asp Ser Asp Gly Cys Tyr Val Gln Leu Pro Arg Ser Arg Pro Ala Leu
        290                 295                 300

Glu Leu Thr Ala Leu Thr Ala Pro Gly Pro Gly Ser Gly Ser Arg Pro
305                 310                 315                 320

Thr Gln Ala Lys Leu Leu Ala Lys Lys Arg Val Lys Arg Met Leu Leu
                325                 330                 335

Val Ile Val Val Leu Phe Phe Leu Cys Trp Leu Pro Val Tyr Ser Ala
            340                 345                 350

Asn Thr Trp Arg Ala Phe Asp Gly Pro Gly Ala His Arg Ala Leu Ser
        355                 360                 365

Val Ala Pro Ile Ser Phe Ile His Leu Leu Ser Tyr Ala Ser Ala Cys
370                 375                 380

Val Asn Pro Leu Val Tyr Cys Phe Met His Arg Arg Phe Arg Gln Ala
385                 390                 395                 400

Cys Leu Glu Thr Cys Ala Arg Cys Cys Pro Arg Pro Pro Arg Ala Arg
                405                 410                 415

Pro Arg Ala Leu Pro Asp Glu Asp Pro Pro Thr Pro Ser Ile Ala Ser
            420                 425                 430

Leu Ser Arg Leu Ser Tyr Thr Thr Ile Ser Thr Leu Gly Pro Gly
        435                 440                 445

<210> SEQ ID NO 113
<211> LENGTH: 34
<212> TYPE: DNA
<213> ORGANISM: Artificial Sequence
<220> FEATURE:
<223> OTHER INFORMATION: Novel Sequence

<400> SEQUENCE: 113
cagcagcatg cgcttcacgc gcttcttagc ccag                            34

<210> SEQ ID NO 114
<211> LENGTH: 35
```

```
<212> TYPE: DNA
<213> ORGANISM: Artificial Sequence
<220> FEATURE:
<223> OTHER INFORMATION: Novel Sequence

<400> SEQUENCE: 114
agaagcgcgt gaagcgcatg ctgctggtga tcgtt                        35

<210> SEQ ID NO 115
<211> LENGTH: 33
<212> TYPE: DNA
<213> ORGANISM: Artificial Sequence
<220> FEATURE:
<223> OTHER INFORMATION: Novel Sequence

<400> SEQUENCE: 115
atggagaaaa gaatcaaaag aatgttctat ata                          33

<210> SEQ ID NO 116
<211> LENGTH: 33
<212> TYPE: DNA
<213> ORGANISM: Artificial Sequence
<220> FEATURE:
<223> OTHER INFORMATION: Novel Sequence

<400> SEQUENCE: 116
tatatagaac attcttttga ttcttttctc cat                          33

<210> SEQ ID NO 117
<211> LENGTH: 30
<212> TYPE: DNA
<213> ORGANISM: Artificial Sequence
<220> FEATURE:
<223> OTHER INFORMATION: Novel Sequence

<400> SEQUENCE: 117
cgctctctgg ccttgaagcg cacgctcagc                              30

<210> SEQ ID NO 118
<211> LENGTH: 30
<212> TYPE: DNA
<213> ORGANISM: Artificial Sequence
<220> FEATURE:
<223> OTHER INFORMATION: Novel Sequence

<400> SEQUENCE: 118
gctgagcgtg cgcttcaagg ccagagagcg                              30

<210> SEQ ID NO 119
<211> LENGTH: 30
<212> TYPE: DNA
<213> ORGANISM: Artificial Sequence
<220> FEATURE:
<223> OTHER INFORMATION: Novel Sequence

<400> SEQUENCE: 119
cccaggaaaa aggtgaaagt caaagttttc                              30

<210> SEQ ID NO 120
<211> LENGTH: 30
<212> TYPE: DNA
<213> ORGANISM: Artificial Sequence
<220> FEATURE:
<223> OTHER INFORMATION: Novel Sequence

<400> SEQUENCE: 120
gaaaactttg actttcacct ttttcctggg                              30
```

```
<210> SEQ ID NO 121
<211> LENGTH: 27
<212> TYPE: DNA
<213> ORGANISM: Artificial Sequence
<220> FEATURE:
<223> OTHER INFORMATION: Novel Sequence

<400> SEQUENCE: 121
ggggcgcggg tgaaacggct ggtgagc                                            27

<210> SEQ ID NO 122
<211> LENGTH: 27
<212> TYPE: DNA
<213> ORGANISM: Artificial Sequence
<220> FEATURE:
<223> OTHER INFORMATION: Novel Sequence

<400> SEQUENCE: 122
gctcaccagc cgtttcaccc gcgcccc                                            27

<210> SEQ ID NO 123
<211> LENGTH: 30
<212> TYPE: DNA
<213> ORGANISM: Artificial Sequence
<220> FEATURE:
<223> OTHER INFORMATION: Novel Sequence

<400> SEQUENCE: 123 cccccttgaaa agcctaagaa cttggtcatc                                        30

<210> SEQ ID NO 124
<211> LENGTH: 30
<212> TYPE: DNA
<213> ORGANISM: Artificial Sequence
<220> FEATURE:
<223> OTHER INFORMATION: Novel Sequence

<400> SEQUENCE: 124
gatgaccaag ttcttaggct tttcaagggg                                         30

<210> SEQ ID NO 125
<211> LENGTH: 32
<212> TYPE: DNA
<213> ORGANISM: Artificial Sequence
<220> FEATURE:
<223> OTHER INFORMATION: Novel Sequence

<400> SEQUENCE: 125
gatctctaga atgaacagca catgtattga ag                                      32

<210> SEQ ID NO 126
<211> LENGTH: 35
<212> TYPE: DNA
<213> ORGANISM: Artificial Sequence
<220> FEATURE:
<223> OTHER INFORMATION: Novel Sequence

<400> SEQUENCE: 126
ctagggtacc cgctcaagga cctctaattc catag                                   35

<210> SEQ ID NO 127
<211> LENGTH: 1296
<212> TYPE: DNA
<213> ORGANISM: Homo sapiens

<400> SEQUENCE: 127
```

-continued

```
atgcaggcgc ttaacattac cccggagcag ttctctcggc tgctgcggga ccacaacctg      60
acgcgggagc agttcatcgc tctgtaccgg ctgcgaccgc tcgtctacac cccagagctg     120
ccgggacgcg ccaagctggc cctcgtgctc accggcgtgc tcatcttcgc cctggcgctc     180
tttggcaatg ctctggtgtt ctacgtggtg acccgcagca aggccatgcg caccgtcacc     240
aacatcttta tctgctcctt ggcgctcagt gacctgctca tccttcttct ctgcattccc     300
gtcaccatgc tccagaacat ttccgacaac tggctggggg gtgctttcat ttgcaagatg     360
gtgccatttg tccagtctac cgctgttgtg acagaaatgc tcactatgac ctgcattgct     420
gtggaaaggc accagggact tgtgcatcct tttaaaatga agtggcaata caccaaccga     480
agggctttca caatgctagg tgtggtctgg ctggtggcag tcatcgtagg atcacccatg     540
tggcacgtgc aacaacttga gatcaaatat gacttcctat atgaaaagga acacatctgc     600
tgcttagaag agtggaccag ccctgtgcac cagaagatct acaccacctt catccttgtc     660
atcctcttcc tcctgcctct tatggtgatg cttattctgt acagtaaaat tggttatgaa     720
ctttggataa agaaaagagt tggggatggt tcagtgcttc gaactattca tggaaaagaa     780
atgtccaaaa tagccaggaa gaagaaacga gctaagatta tgatggtgac agtggtggct     840
ctctttgctg tgtgctgggc accattccat gttgtcccata tgatgattga atacagtaat     900
tttgaaaagg aatatgatga tgtcacaatc aagatgattt ttgctatcgt gcaaattatt     960
ggatttttcca actccatctg taatcccatt gtctatgcat ttatgaatga aacttcaaa    1020
aaaaatgttt tgtctgcagt ttgttattgc atagtaaata aaaccttctc tccagcacaa    1080
aggcatggaa attcaggaat acaatgatgc ggaagaaag caagttttc cctcagagag     1140
aatccagtgg aggaaaccaa aggagaagca ttcagtgatg caacattga agtcaaattg    1200
tgtgaacaga cagaggagaa gaaaaagctc aaacgacatc ttgctctctt taggtctgaa    1260
ctggctgaga attctccttt agacagtggg cattaa                             1296
```

<210> SEQ ID NO 128
<211> LENGTH: 431
<212> TYPE: PRT
<213> ORGANISM: Homo sapiens

<400> SEQUENCE: 128

Met Gln Ala Leu Asn Ile Thr Pro Glu Gln Phe Ser Arg Leu Leu Arg
1               5                   10                  15

Asp His Asn Leu Thr Arg Glu Gln Phe Ile Ala Leu Tyr Arg Leu Arg
            20                  25                  30

Pro Leu Val Tyr Thr Pro Glu Leu Pro Gly Arg Ala Lys Leu Ala Leu
        35                  40                  45

Val Leu Thr Gly Val Leu Ile Phe Ala Leu Ala Leu Phe Gly Asn Ala
    50                  55                  60

Leu Val Phe Tyr Val Val Thr Arg Ser Lys Ala Met Arg Thr Val Thr
65                  70                  75                  80

Asn Ile Phe Ile Cys Ser Leu Ala Leu Ser Asp Leu Leu Ile Thr Phe
                85                  90                  95

Phe Cys Ile Pro Val Thr Met Leu Gln Asn Ile Ser Asp Asn Trp Leu
            100                 105                 110

Gly Gly Ala Phe Ile Cys Lys Met Val Pro Phe Val Gln Ser Thr Ala
        115                 120                 125

Val Val Thr Glu Met Leu Thr Met Thr Cys Ile Ala Val Glu Arg His
    130                 135                 140

-continued

```
Gln Gly Leu Val His Pro Phe Lys Met Lys Trp Gln Tyr Thr Asn Arg
145                 150                 155                 160

Arg Ala Phe Thr Met Leu Gly Val Val Trp Leu Val Ala Val Ile Val
            165                 170                 175

Gly Ser Pro Met Trp His Val Gln Gln Leu Glu Ile Lys Tyr Asp Phe
            180                 185                 190

Leu Tyr Glu Lys Glu His Ile Cys Cys Leu Glu Glu Trp Thr Ser Pro
            195                 200                 205

Val His Gln Lys Ile Tyr Thr Thr Phe Ile Leu Val Ile Leu Phe Leu
            210                 215                 220

Leu Pro Leu Met Val Met Leu Ile Leu Tyr Ser Lys Ile Gly Tyr Glu
225                 230                 235                 240

Leu Trp Ile Lys Lys Arg Val Gly Asp Gly Ser Val Leu Arg Thr Ile
            245                 250                 255

His Gly Lys Glu Met Ser Lys Ile Ala Arg Lys Lys Arg Ala Lys
            260                 265                 270

Ile Met Met Val Thr Val Val Ala Leu Phe Ala Val Cys Trp Ala Pro
            275                 280                 285

Phe His Val Val His Met Met Ile Glu Tyr Ser Asn Phe Glu Lys Glu
            290                 295                 300

Tyr Asp Asp Val Thr Ile Lys Met Ile Phe Ala Ile Val Gln Ile Ile
305                 310                 315                 320

Gly Phe Ser Asn Ser Ile Cys Asn Pro Ile Val Tyr Ala Phe Met Asn
            325                 330                 335

Glu Asn Phe Lys Lys Asn Val Leu Ser Ala Val Cys Tyr Cys Ile Val
            340                 345                 350

Asn Lys Thr Phe Ser Pro Ala Gln Arg His Gly Asn Ser Gly Ile Thr
            355                 360                 365

Met Met Arg Lys Lys Ala Lys Phe Ser Leu Arg Glu Asn Pro Val Glu
            370                 375                 380

Glu Thr Lys Gly Glu Ala Phe Ser Asp Gly Asn Ile Glu Val Lys Leu
385                 390                 395                 400

Cys Glu Gln Thr Glu Lys Lys Lys Leu Lys Arg His Leu Ala Leu
            405                 410                 415

Phe Arg Ser Glu Leu Ala Glu Asn Ser Pro Leu Asp Ser Gly His
            420                 425                 430
```

<210> SEQ ID NO 129
<211> LENGTH: 2040
<212> TYPE: DNA
<213> ORGANISM: Homo sapiens

<400> SEQUENCE: 129

```
atgggcagcc cctggaacgg cagcgacggc cccgaggggg cgcgggagcc gccgtggccc      60
gcgctgccgc cttgcgacga gcgccgctgc tcgccctttc ccctgggggc gctggtgccg     120
gtgaccgctg tgtgcctgtg cctgttcgtc gtcggggtga gcggcaacgt ggtgaccgtg     180
atgctgatcg gcgctaccg ggacatgcgg accaccacca acttgtacct gggcagcatg     240
gccgtgtccg acctactcat cctgctcggg ctgccgttcg acctgtaccg cctctggcgc     300
tcgcggccct gggtgttcgg gccgctgctc tgccgcctgt ccctctacgt gggcgagggc     360
tgcacctacg ccacgctgct gcacatgacc gcgctcagcg tcgagcgcta cctggccatc     420
tgccgcccgc tccgcgcccg cgtcttggtc accggcgcc gcgtccgcgc gctcatcgct     480
gtgctctggg ccgtggcgct gctctctgcc ggtcccttct tgttcctggt gggcgtcgag     540
```

```
caggaccccg gcatctccgt agtcccgggc ctcaatggca ccgcgcggat cgcctcctcg    600
cctctcgcct cgtcgccgcc tctctggctc tcgcgggcgc caccgccgtc ccgccgtcg    660
gggcccgaga ccgcggaggc cgcggcgctg ttcagccgcg aatgccggcc gagccccgcg    720
cagctgggcg cgctgcgtgt catgctgtgg gtcaccaccg cctacttctt cctgcccttt    780
ctgtgcctca gcatcctcta cgggctcatc gggcgggagc tgtggagcag ccggcggccg    840
ctgcgaggcc cggccgcctc ggggcgggag agaggccacc ggcagaccaa acgcgtcctg    900
cgtaagtgga ccgccgtgg ttccaaagac gcctgcctgc agtccgcccc gccggggacc    960
gcgcaaacgc tgggtcccct tcccctgctc gcccagctct gggcgccgct tccagctccc   1020
tttcctattt cgattccagc ctccacccgc cggtacttcc catcccccga gaaaaccatg   1080
tcctgtcccc caggagctct gggggacccc agggcgcttt gagggtggga tccccggatc   1140
cgattcagta accagcagtg cttttccaga gcctctgaga ccagaaagga gagttggtaa   1200
ttcttaatcc aaccacctgt tagatgccac aaatgaggag tcctcacagt gctcttgaga   1260
agacgaggga gatttcatta agctaaaatt ttttatttaa tgttaagtga tgctgaaggc   1320
taaagtaaac cttgctcgta tcaaaaagta aagattgtgc agacctgttg tagaattctt   1380
ttcaacagag aacagaaaac ttgtctccga agtgggtttg tggaaggaag cctgccaagg   1440
cggcttgttc agagaaattg ctccttctgg tttatgtcca gccttgataa cacatatggg   1500
agcctactat gcagttttaa agcaagtatc catgcagcct gcagcctggt catttttct    1560
ggggtgagga tctgcctagg tagaagtttt ctctaattta ttttgctgtt acttgttatt   1620
gcagatggtt ccttgtcggg gtggggggtt tatttgcttc ccaatgcttt tgttaatccc   1680
ggtgctgtgt cttatgttgc agtggtggtg gttctggcat ttataatttg ctggttgccc   1740
ttccacgttg gcagaatcat ttacataaac acggaagatt cgcggatgat gtacttctct   1800
cagtacttta acatcgtcgc tctgcaactt ttctatctga gcgcatctat caacccaatc   1860
ctctacaacc tcatttcaaa gaagtacaga gcggcggcct taaactgct gctcgcaagg   1920
aagtccaggc cgagaggctt ccacagaagc agggacactg cggggggaagt tgcagggggac  1980
actggaggag cacggtggg ctacaccgag acaagcgcta acgtgaagac gatgggataa   2040
```

<210> SEQ ID NO 130
<211> LENGTH: 412
<212> TYPE: PRT
<213> ORGANISM: Homo sapiens

<400> SEQUENCE: 130

```
Met Gly Ser Pro Trp Asn Gly Ser Asp Gly Pro Glu Gly Ala Arg Glu
1               5                   10                  15

Pro Pro Trp Pro Ala Leu Pro Pro Cys Asp Glu Arg Arg Cys Ser Pro
            20                  25                  30

Phe Pro Leu Gly Ala Leu Val Pro Val Thr Ala Val Cys Leu Cys Leu
        35                  40                  45

Phe Val Val Gly Val Ser Gly Asn Val Thr Val Met Leu Ile Gly
    50                  55                  60

Arg Tyr Arg Asp Met Arg Thr Thr Thr Asn Leu Tyr Leu Gly Ser Met
65              70                  75                  80

Ala Val Ser Asp Leu Leu Ile Leu Leu Gly Leu Pro Phe Asp Leu Tyr
                85                  90                  95

Arg Leu Trp Arg Ser Arg Pro Trp Val Phe Gly Pro Leu Leu Cys Arg
            100                 105                 110

Leu Ser Leu Tyr Val Gly Glu Gly Cys Thr Tyr Ala Thr Leu Leu His
```

```
                115                 120                125
Met Thr Ala Leu Ser Val Glu Arg Tyr Leu Ala Ile Cys Arg Pro Leu
    130                 135                140

Arg Ala Arg Val Leu Val Thr Arg Arg Val Arg Ala Leu Ile Ala
145                 150                155                160

Val Leu Trp Ala Val Ala Leu Leu Ser Ala Gly Pro Phe Leu Phe Leu
                165                170                175

Val Gly Val Glu Gln Asp Pro Gly Ile Ser Val Val Pro Gly Leu Asn
                180                185                190

Gly Thr Ala Arg Ile Ala Ser Ser Pro Leu Ala Ser Ser Pro Pro Leu
                195                200                205

Trp Leu Ser Arg Ala Pro Pro Pro Ser Pro Pro Ser Gly Pro Glu Thr
                210                215                220

Ala Glu Ala Ala Ala Leu Phe Ser Arg Glu Cys Arg Pro Ser Pro Ala
225                 230                235                240

Gln Leu Gly Ala Leu Arg Val Met Leu Trp Val Thr Thr Ala Tyr Phe
                245                250                255

Phe Leu Pro Phe Leu Cys Leu Ser Ile Leu Tyr Gly Leu Ile Gly Arg
                260                265                270

Glu Leu Trp Ser Ser Arg Arg Pro Leu Arg Gly Pro Ala Ala Ser Gly
                275                280                285

Arg Glu Arg Gly His Arg Gln Thr Lys Arg Val Leu Leu Val Val Val
290                 295                300

Leu Ala Phe Ile Ile Cys Trp Leu Pro Phe His Val Gly Arg Ile Ile
305                 310                315                320

Tyr Ile Asn Thr Glu Asp Ser Arg Met Met Tyr Phe Ser Gln Tyr Phe
                325                330                335

Asn Ile Val Ala Leu Gln Leu Phe Tyr Leu Ser Ala Ser Ile Asn Pro
                340                345                350

Ile Leu Tyr Asn Leu Ile Ser Lys Lys Tyr Arg Ala Ala Ala Phe Lys
                355                360                365

Leu Leu Leu Ala Arg Lys Ser Arg Pro Arg Gly Phe His Arg Ser Arg
                370                375                380

Asp Thr Ala Gly Glu Val Ala Gly Asp Thr Gly Gly Asp Thr Val Gly
385                 390                395                400

Tyr Thr Glu Thr Ser Ala Asn Val Lys Thr Met Gly
                405                410

<210> SEQ ID NO 131
<211> LENGTH: 1344
<212> TYPE: DNA
<213> ORGANISM: Homo sapiens

<400> SEQUENCE: 131
atggagctgc taaagctgaa ccggagcgtg cagggaaccg gacccgggcc ggggggcttcc    60 ctgtgccgcc cggggggcgcc tctcctcaac agcagcagtg tgggcaaccct cagctgcgag   120 cccctcgca ttcgcggagc cgggacacga gaattggagc tggccattag aatcactctt    180
tacgcagtga tcttcctgat gagcgttgga ggaaatatgc tcatcatcgt ggtcctggga   240
ctgagccgcc gcctgaggac tgtcaccaat gccttcctcc tctcactggc agtcagcgac   300
ctcctgctgg ctgtggcttg catgcccttc accctcctgc ccaatctcat gggcacattc   360
atctttggca ccgtcatctg caaggcggtt cctacctca tggggggtgtc tgtgagtgtg   420 tccacgctaa gcctcgtggc catcgcactg gagcgatata cgccatctg ccgaccactg   480
```

-continued

```
caggcacgag tgtggcagac gcgctcccac gcggctcgcg tgattgtagc cacgtggctg      540
ctgtccggac tactcatggt gccctacccc gtgtacactg tcgtgcaacc agtggggcct      600
cgtgtgctgc agtgcgtgca tcgctggccc agtgcgcggg tccgccagac tggtccgta      660
ctgctgcttc tgctcttgtt cttcatccca ggtgtggtta tggccgtggc ctacgggctt      720
atctctcgcg agctctactt agggcttcgc tttgacggcg acagtgacag cgacagccaa      780
agcagggtcc gaaaccaagg cgggctgcca ggggctgttc accagaacgg cgttgccgg      840
cctgagactg gcgcggttgg caaagacagc gatggctgct acgtgcaact ccacgttcc      900
cggcctgccc tggagctgac ggcgctgacg gctcctgggc cgggatccgg ctcccggccc      960
acccaggcca agctgctggc taagaagcgc gtgaaacgaa tgttgctggt gatcgttgtg     1020
ctttttttc tgtgttggtt gccagtttat agtgccaaca cgtggcgcgc ctttgatggc     1080
ccgggtgcac accgagcact ctcgggtgct cctatctcct tcattcactt gctgagctac     1140
gcctcggcct gtgtcaaccc cctggtctac tgcttcatgc accgtcgctt cgccaggcc     1200
tgcctggaaa cttgcgctcg ctgctgcccc cggcctccac gagctcgccc cagggctctt     1260
cccgatgagg accctcccac tccctccatt gcttcgctgt ccaggcttag ctacaccacc     1320
atcagcacac tgggccctgg ctga                                            1344
```

<210> SEQ ID NO 132
<211> LENGTH: 447
<212> TYPE: PRT
<213> ORGANISM: Homo sapiens

<400> SEQUENCE: 132

```
Met Glu Leu Leu Lys Leu Asn Arg Ser Val Gln Gly Thr Gly Pro Gly
1               5                   10                  15

Pro Gly Ala Ser Leu Cys Arg Pro Gly Ala Pro Leu Leu Asn Ser Ser
            20                  25                  30

Ser Val Gly Asn Leu Ser Cys Glu Pro Pro Arg Ile Arg Gly Ala Gly
        35                  40                  45

Thr Arg Glu Leu Glu Leu Ala Ile Arg Ile Thr Leu Tyr Ala Val Ile
    50                  55                  60

Phe Leu Met Ser Val Gly Gly Asn Met Leu Ile Ile Val Val Leu Gly
65                  70                  75                  80

Leu Ser Arg Arg Leu Arg Thr Val Thr Asn Ala Phe Leu Leu Ser Leu
                85                  90                  95

Ala Val Ser Asp Leu Leu Leu Ala Val Ala Cys Met Pro Phe Thr Leu
            100                 105                 110

Leu Pro Asn Leu Met Gly Thr Phe Ile Phe Gly Thr Val Ile Cys Lys
        115                 120                 125

Ala Val Ser Tyr Leu Met Gly Val Ser Val Ser Val Ser Thr Leu Ser
    130                 135                 140

Leu Val Ala Ile Ala Leu Glu Arg Tyr Ser Ala Ile Cys Arg Pro Leu
145                 150                 155                 160

Gln Ala Arg Val Trp Gln Thr Arg Ser His Ala Ala Arg Val Ile Val
                165                 170                 175

Ala Thr Trp Leu Leu Ser Gly Leu Leu Met Val Pro Tyr Pro Val Tyr
            180                 185                 190

Thr Val Val Gln Pro Val Gly Pro Arg Val Leu Gln Cys Val His Arg
        195                 200                 205

Trp Pro Ser Ala Arg Val Arg Gln Thr Trp Ser Val Leu Leu Leu Leu
    210                 215                 220
```

| | | | | | | | | | | | | |
|---|---|---|---|---|---|---|---|---|---|---|---|---|
|Leu|Leu|Phe|Phe|Ile|Pro|Gly|Val|Val|Met|Ala|Val|Ala|Tyr|Gly|Leu|
|225| | | |230| | | |235| | | |240|

Ile Ser Arg Glu Leu Tyr Leu Gly Leu Arg Phe Asp Gly Asp Ser Asp
                  245                  250                  255

Ser Asp Ser Gln Ser Arg Val Arg Asn Gln Gly Gly Leu Pro Gly Ala
        260                  265                  270

Val His Gln Asn Gly Arg Cys Arg Pro Glu Thr Gly Ala Val Gly Lys
        275                  280                  285

Asp Ser Asp Gly Cys Tyr Val Gln Leu Pro Arg Ser Arg Pro Ala Leu
    290                  295                  300

Glu Leu Thr Ala Leu Thr Ala Pro Gly Pro Gly Ser Gly Ser Arg Pro
305                  310                  315                  320

Thr Gln Ala Lys Leu Leu Ala Lys Lys Arg Val Lys Arg Met Leu Leu
            325                  330                  335

Val Ile Val Val Leu Phe Phe Leu Cys Trp Leu Pro Val Tyr Ser Ala
        340                  345                  350

Asn Thr Trp Arg Ala Phe Asp Gly Pro Gly Ala His Arg Ala Leu Ser
            355                  360                  365

Val Ala Pro Ile Ser Phe Ile His Leu Leu Ser Tyr Ala Ser Ala Cys
    370                  375                  380

Val Asn Pro Leu Val Tyr Cys Phe Met His Arg Arg Phe Arg Gln Ala
385                  390                  395                  400

Cys Leu Glu Thr Cys Ala Arg Cys Cys Pro Arg Pro Arg Ala Arg
            405                  410                  415

Pro Arg Ala Leu Pro Asp Glu Asp Pro Pro Thr Pro Ser Ile Ala Ser
            420                  425                  430

Leu Ser Arg Leu Ser Tyr Thr Thr Ile Ser Thr Leu Gly Pro Gly
        435                  440                  445

<210> SEQ ID NO 133
<211> LENGTH: 1014
<212> TYPE: DNA
<213> ORGANISM: Homo sapiens

<400> SEQUENCE: 133

```
atgaacagca catgtattga agaacagcat gacctggatc actatttgtt tcccattgtt      60
tacatctttg tgattatagt cagcattcca gccaatattg gatctctgtg tgtgtctttc     120
ctgcaagcaa agaaggaaag tgaactagga atttacctct tcagtttgtc actatcagat     180
ttactctata cattaactct ccctttatgg attgattata cttggaataa agacaactgg     240
actttctctc ctgccttgtg caaagggagt gcttttctca tgtacatgaa tttttacagc     300
agcacagcat tcctcacctg cattgccgtt gatcggtatt ggctgttgt ctacccttg      360
aagtttttt tcctaaggac aagaagattt gcactcatgg tcagcctgtc catctggata     420
ttggaaacca tcttcaatgc tgtcatgttg tgggaagatg aaacagttgt tgaatattgc     480
gatgccgaaa agtctaattt tactttatgc tatgacaaat acccttaga gaaatggcaa     540
atcaacctca acttgttcag gacgtgtaca ggctatgcaa tacctttggt caccatcctg     600
atctgtaacc ggaaagtcta ccaagctgtg cggcacaata aagccacgga aacaaggaa      660
aagaagagaa tcaaaaaact acttgtcagc atcacagtta cttttgtctt atgctttact     720
cccttttcatg tgatgttgct gattcgctgc attttagagc atgctgtgaa cttcgaagac     780
cacagcaatt ctgggaagcg aacttacaca atgtatagaa tcacggttgc attaacaagt     840
ttaaattgtg ttgctgatcc aattctgtac tgttttgtta ccgaaacagg aagatatgat     900
```

```
atgtggaata tattaaaatt ctgcactggg aggtgtaata catcacaaag acaaagaaaa      960
cgcatacttt ctgtgtctac aaaagatact atggaattag aggtccttga gtag           1014
```

<210> SEQ ID NO 134
<211> LENGTH: 337
<212> TYPE: PRT
<213> ORGANISM: Homo sapiens

<400> SEQUENCE: 134

```
Met Asn Ser Thr Cys Ile Glu Glu Gln His Asp Leu Asp His Tyr Leu
1               5                   10                  15

Phe Pro Ile Val Tyr Ile Phe Val Ile Val Ser Ile Pro Ala Asn
                20                  25                  30

Ile Gly Ser Leu Cys Val Ser Phe Leu Gln Ala Lys Lys Glu Ser Glu
        35                  40                  45

Leu Gly Ile Tyr Leu Phe Ser Leu Ser Leu Ser Asp Leu Leu Tyr Ala
    50                  55                  60

Leu Thr Leu Pro Leu Trp Ile Asp Tyr Thr Trp Asn Lys Asp Asn Trp
65                  70                  75                  80

Thr Phe Ser Pro Ala Leu Cys Lys Gly Ser Ala Phe Leu Met Tyr Met
                85                  90                  95

Asn Phe Tyr Ser Ser Thr Ala Phe Leu Thr Cys Ile Ala Val Asp Arg
                100                 105                 110

Tyr Leu Ala Val Val Tyr Pro Leu Lys Phe Phe Leu Arg Thr Arg
        115                 120                 125

Arg Phe Ala Leu Met Val Ser Leu Ser Ile Trp Ile Leu Glu Thr Ile
130                 135                 140

Phe Asn Ala Val Met Leu Trp Glu Asp Glu Thr Val Val Glu Tyr Cys
145                 150                 155                 160

Asp Ala Glu Lys Ser Asn Phe Thr Leu Cys Tyr Asp Lys Tyr Pro Leu
                165                 170                 175

Glu Lys Trp Gln Ile Asn Leu Asn Leu Phe Arg Thr Cys Thr Gly Tyr
                180                 185                 190

Ala Ile Pro Leu Val Thr Ile Leu Ile Cys Asn Arg Lys Val Tyr Gln
        195                 200                 205

Ala Val Arg His Asn Lys Ala Thr Glu Asn Lys Glu Lys Lys Arg Ile
    210                 215                 220

Lys Lys Leu Leu Val Ser Ile Thr Val Thr Phe Val Leu Cys Phe Thr
225                 230                 235                 240

Pro Phe His Val Met Leu Leu Ile Arg Cys Ile Leu Glu His Ala Val
                245                 250                 255

Asn Phe Glu Asp His Ser Asn Ser Gly Lys Arg Thr Tyr Thr Met Tyr
                260                 265                 270

Arg Ile Thr Val Ala Leu Thr Ser Leu Asn Cys Val Ala Asp Pro Ile
        275                 280                 285

Leu Tyr Cys Phe Val Thr Glu Thr Gly Arg Tyr Asp Met Trp Asn Ile
    290                 295                 300

Leu Lys Phe Cys Thr Gly Arg Cys Asn Thr Ser Gln Arg Gln Arg Lys
305                 310                 315                 320

Arg Ile Leu Ser Val Ser Thr Lys Asp Thr Met Glu Leu Glu Val Leu
                325                 330                 335

Glu
```

<210> SEQ ID NO 135
<211> LENGTH: 999

<212> TYPE: DNA
<213> ORGANISM: Homo sapiens

<400> SEQUENCE: 135

```
atggtgaact ccacccaccg tgggatgcac acttctctgc acctctggaa ccgcagcagt      60
tacagactgc acagcaatgc cagtgagtcc cttggaaaag gctactctga tggagggtgc     120
tacgagcaac tttttgtctc tcctgaggtg tttgtgactc tgggtgtcat cagcttgttg     180
gagaatatct tagtgattgt ggcaatagcc aagaacaaga atctgcattc acccatgtac     240
tttttcatct gcagcttggc tgtggctgat atgctggtga cgtttcaaa tggatcagaa      300
accattatca tcaccctatt aaacagtaca gatacggatg cacagagttt cacagtgaat     360
attgataatg tcattgactc ggtgatctgt agctccttgc ttgcatccat ttgcagcctg     420
ctttcaattg cagtggacag gtactttact atcttctatg ctctccagta ccataacatt     480
atgacagtta agcgggttgg gatcagcata agttgtatct gggcagcttg cacggtttca     540
ggcatttttgt tcatcattta ctcagatagt agtgctgtca tcatctgcct catcaccatg     600
ttcttcacca tgctggctct catggcttct ctctatgtcc acatgttcct gatggccagg     660
cttcacatta gaggattgc tgtcctcccc ggcactggtg ccatccgcca aggtgccaat      720
atgaagggaa aaattacctt gaccatcctg attggcgtct tgttgtctg ctgggcccca     780
ttcttcctcc acttaatatt ctacatctct tgtcctcaga tccatattg tgtgcttc       840
atgtctcact ttaacttgta tctcatactg atcatgtgta attcaatcat cgatcctctg     900
atttatgcac tccggagtca agaactgagg aaaaccttca agagatcat ctgttgctat      960
cccctgggag gcctttgtga cttgtctagc agatattaa                            999
```

<210> SEQ ID NO 136
<211> LENGTH: 332
<212> TYPE: PRT
<213> ORGANISM: Homo sapiens

<400> SEQUENCE: 136

```
Met Val Asn Ser Thr His Arg Gly Met His Thr Ser Leu His Leu Trp
1               5                   10                  15

Asn Arg Ser Ser Tyr Arg Leu His Ser Asn Ala Ser Glu Ser Leu Gly
            20                  25                  30

Lys Gly Tyr Ser Asp Gly Gly Cys Tyr Glu Gln Leu Phe Val Ser Pro
        35                  40                  45

Glu Val Phe Val Thr Leu Gly Val Ile Ser Leu Leu Glu Asn Ile Leu
    50                  55                  60

Val Ile Val Ala Ile Ala Lys Asn Lys Asn Leu His Ser Pro Met Tyr
65                  70                  75                  80

Phe Phe Ile Cys Ser Leu Ala Val Ala Asp Met Leu Val Ser Val Ser
                85                  90                  95

Asn Gly Ser Glu Thr Ile Ile Ile Thr Leu Leu Asn Ser Thr Asp Thr
            100                 105                 110

Asp Ala Gln Ser Phe Thr Val Asn Ile Asp Asn Val Ile Asp Ser Val
        115                 120                 125

Ile Cys Ser Ser Leu Leu Ala Ser Ile Cys Ser Leu Leu Ser Ile Ala
    130                 135                 140

Val Asp Arg Tyr Phe Thr Ile Phe Tyr Ala Leu Gln Tyr His Asn Ile
145                 150                 155                 160

Met Thr Val Lys Arg Val Gly Ile Ser Ile Ser Cys Ile Trp Ala Ala
                165                 170                 175
```

-continued

```
Cys Thr Val Ser Gly Ile Leu Phe Ile Ile Tyr Ser Asp Ser Ser Ala
            180                 185                 190
Val Ile Ile Cys Leu Ile Thr Met Phe Phe Thr Met Leu Ala Leu Met
        195                 200                 205
Ala Ser Leu Tyr Val His Met Phe Leu Met Ala Arg Leu His Ile Lys
    210                 215                 220
Arg Ile Ala Val Leu Pro Gly Thr Gly Ala Ile Arg Gln Gly Ala Asn
225                 230                 235                 240
Met Lys Gly Lys Ile Thr Leu Thr Ile Leu Ile Gly Val Phe Val Val
                245                 250                 255
Cys Trp Ala Pro Phe Phe Leu His Leu Ile Phe Tyr Ile Ser Cys Pro
            260                 265                 270
Gln Asn Pro Tyr Cys Val Cys Phe Met Ser His Phe Asn Leu Tyr Leu
        275                 280                 285
Ile Leu Ile Met Cys Asn Ser Ile Ile Asp Pro Leu Ile Tyr Ala Leu
    290                 295                 300
Arg Ser Gln Glu Leu Arg Lys Thr Phe Lys Glu Ile Ile Cys Cys Tyr
305                 310                 315                 320
Pro Leu Gly Gly Leu Cys Asp Leu Ser Ser Arg Tyr
                325                 330
```

```
<210> SEQ ID NO 137
<211> LENGTH: 33
<212> TYPE: DNA
<213> ORGANISM: Artificial Sequence
<220> FEATURE:
<223> OTHER INFORMATION: Novel Sequence

<400> SEQUENCE: 137
gccaatatga agggaaaaat taccttgacc atc                              33

<210> SEQ ID NO 138
<211> LENGTH: 31
<212> TYPE: DNA
<213> ORGANISM: Artificial Sequence
<220> FEATURE:
<223> OTHER INFORMATION: Novel Sequence

<400> SEQUENCE: 138
ctccttcggt cctcctatcg ttgtcagaag t                                31

<210> SEQ ID NO 139
<211> LENGTH: 1842
<212> TYPE: DNA
<213> ORGANISM: Homo sapiens

<400> SEQUENCE: 139
atggggccca ccctagcggt tcccacccca tatggctgta ttggctgtaa gctaccccag      60
ccagaatacc caccggctct aatcatcttt atgttctgcg cgatggttat caccatcgtt     120
gtagacctaa tcggcaactc catggtcatt ttggctgtga cgaagaacaa gaagctccgg     180
aattctggca acatcttcgt ggtcagtctc tctgtggccg atatgctggt ggccatctac     240
ccatcccctt tgatgctgca tgccatgtcc attggggct gggatctgag ccagttacag     300
tgccagatgg tcgggttcat cacagggctg agtgtggtcg gctccatctt caacatcgtg     360
gcaatcgcta tcaaccgtta ctgctacatc tgccacagcc tccagtacga acggatcttc     420
agtgtgcgca atacctgcat ctacctggtc atcacctgga tcatgaccgt cctggctgtc     480
ctgcccaaca tgtacattgg caccatcgag tacgatccac gcacctacac ctgcatcttc     540
```

```
aactatctga caaccctgt cttcactgtt accatcgtct gcatccactt cgtcctccct    600
ctcctcatcg tgggtttctg ctacgtgagg atctggacca aagtgctggc ggcccgtgac    660
cctgcagggc agaatcctga caaccaactt gctgaggttc gcaattttct aaccatgttt    720
gtgatcttcc tcctctttgc agtgtgctgg tgcccatca acgtgctcac tgtcttggtg    780
gctgtcagtc cgaaggagat ggcaggcaag atccccaact ggctttatct tgcagcctac    840
ttcatagcct acttcaacag ctgcctcaac gctgtgatct acgggctcct caatgagaat    900
ttccgaagag aatactggac catcttccat gctatgcggc accctatcat attcttccct    960
ggcctcatca gtgatattcg tgagatgcag gaggcccgta ccctggcccg cgccgtgcc    1020
catgctcgcg accaagctcg tgaacaagac cgtgcccatg cctgtcctgc tgtggaggaa    1080
accccgatga atgtccggaa tgttccatta cctggtgatg ctgcagctgg ccaccccgac    1140
cgtgcctctg ccaccctaa gccccattcc agatcctcct ctgcctatcg caaatctgcc    1200
tctacccacc acaagtctgt ctttagccac tccaaggctg cctctggtca cctcaagcct    1260
gtctctggcc actccaagcc tgcctctggt caccccaagt ctgccactgt ctaccctaag    1320
cctgcctctg tccatttcaa gggtgactct gtccatttca agggtgactc tgtccatttc    1380
aagcctgact ctgttcattt caagcctgct tccagcaacc ccaagcccat cactggccac    1440
catgtctctg ctggcagcca ctccaagtct gccttcagtg ctgccaccag ccaccctaaa    1500
cccatcaagc cagctaccag ccatgctgag cccaccactg ctgactatcc caagcctgcc    1560
actaccagcc ccctaagcc cgctgctgct gacaaccctg agctctctgc ctcccattgc    1620
cccgagatcc ctgccattgc ccaccctgtg tctgacgaca gtgacctccc tgagtcggcc    1680
tctagccctg ccgctgggcc caccaagcct gctgccagcc agctggagtc tgacaccatc    1740
gctgaccttc ctgaccctac tgtagtcact accagtacca atgattacca tgatgtcgtg    1800
gttgttgatg ttgaagatga tcctgatgaa atggctgtgt ga                      1842

<210> SEQ ID NO 140
<211> LENGTH: 613
<212> TYPE: PRT
<213> ORGANISM: Homo sapiens

<400> SEQUENCE: 140

Met Gly Pro Thr Leu Ala Val Pro Thr Pro Tyr Gly Cys Ile Gly Cys
1               5                   10                  15

Lys Leu Pro Gln Pro Glu Tyr Pro Pro Ala Leu Ile Ile Phe Met Phe
            20                  25                  30

Cys Ala Met Val Ile Thr Ile Val Asp Leu Ile Gly Asn Ser Met
        35                  40                  45

Val Ile Leu Ala Val Thr Lys Asn Lys Lys Leu Arg Asn Ser Gly Asn
    50                  55                  60

Ile Phe Val Val Ser Leu Ser Val Ala Asp Met Leu Val Ala Ile Tyr
65                  70                  75                  80

Pro Tyr Pro Leu Met Leu His Ala Met Ser Ile Gly Gly Trp Asp Leu
                85                  90                  95

Ser Gln Leu Gln Cys Gln Met Val Gly Phe Ile Thr Gly Leu Ser Val
            100                 105                 110

Val Gly Ser Ile Phe Asn Ile Val Ala Ile Ala Ile Asn Arg Tyr Cys
        115                 120                 125

Tyr Ile Cys His Ser Leu Gln Tyr Glu Arg Ile Phe Ser Val Arg Asn
    130                 135                 140

Thr Cys Ile Tyr Leu Val Ile Thr Trp Ile Met Thr Val Leu Ala Val
```

```
            145                 150                 155                 160
Leu Pro Asn Met Tyr Ile Gly Thr Ile Glu Tyr Asp Pro Arg Thr Tyr
                165                 170                 175

Thr Cys Ile Phe Asn Tyr Leu Asn Asn Pro Val Phe Thr Val Thr Ile
                180                 185                 190

Val Cys Ile His Phe Val Leu Pro Leu Leu Ile Val Gly Phe Cys Tyr
                195                 200                 205

Val Arg Ile Trp Thr Lys Val Leu Ala Ala Arg Asp Pro Ala Gly Gln
            210                 215                 220

Asn Pro Asp Asn Gln Leu Ala Glu Val Arg Asn Phe Leu Thr Met Phe
225                 230                 235                 240

Val Ile Phe Leu Leu Phe Ala Val Cys Trp Cys Pro Ile Asn Val Leu
                245                 250                 255

Thr Val Leu Val Ala Val Ser Pro Lys Glu Met Ala Gly Lys Ile Pro
                260                 265                 270

Asn Trp Leu Tyr Leu Ala Ala Tyr Phe Ile Ala Tyr Phe Asn Ser Cys
            275                 280                 285

Leu Asn Ala Val Ile Tyr Gly Leu Leu Asn Glu Asn Phe Arg Arg Glu
            290                 295                 300

Tyr Trp Thr Ile Phe His Ala Met Arg His Pro Ile Ile Phe Phe Pro
305                 310                 315                 320

Gly Leu Ile Ser Asp Ile Arg Glu Met Gln Glu Ala Arg Thr Leu Ala
                325                 330                 335

Arg Ala Arg Ala His Ala Arg Asp Gln Ala Arg Glu Gln Asp Arg Ala
                340                 345                 350

His Ala Cys Pro Ala Val Glu Glu Thr Pro Met Asn Val Arg Asn Val
                355                 360                 365

Pro Leu Pro Gly Asp Ala Ala Ala Gly His Pro Asp Arg Ala Ser Gly
            370                 375                 380

His Pro Lys Pro His Ser Arg Ser Ser Ala Tyr Arg Lys Ser Ala
385                 390                 395                 400

Ser Thr His His Lys Ser Val Phe Ser His Ser Lys Ala Ala Ser Gly
                405                 410                 415

His Leu Lys Pro Val Ser Gly His Ser Lys Pro Ala Ser Gly His Pro
                420                 425                 430

Lys Ser Ala Thr Val Tyr Pro Lys Pro Ala Ser Val His Phe Lys Gly
            435                 440                 445

Asp Ser Val His Phe Lys Gly Asp Ser Val His Phe Lys Pro Asp Ser
450                 455                 460

Val His Phe Lys Pro Ala Ser Ser Asn Pro Lys Pro Ile Thr Gly His
465                 470                 475                 480

His Val Ser Ala Gly Ser His Ser Lys Ser Ala Phe Ser Ala Ala Thr
                485                 490                 495

Ser His Pro Lys Pro Ile Lys Pro Ala Thr Ser His Ala Glu Pro Thr
                500                 505                 510

Thr Ala Asp Tyr Pro Lys Pro Ala Thr Thr Ser His Pro Lys Pro Ala
                515                 520                 525

Ala Ala Asp Asn Pro Glu Leu Ser Ala Ser His Cys Pro Glu Ile Pro
            530                 535                 540

Ala Ile Ala His Pro Val Ser Asp Asp Ser Asp Leu Pro Glu Ser Ala
545                 550                 555                 560

Ser Ser Pro Ala Ala Gly Pro Thr Lys Pro Ala Ala Ser Gln Leu Glu
                565                 570                 575
```

```
Ser Asp Thr Ile Ala Asp Leu Pro Asp Pro Thr Val Thr Thr Ser
        580                 585                 590

Thr Asn Asp Tyr His Asp Val Val Val Asp Val Glu Asp Asp Pro
    595                 600                 605

Asp Glu Met Ala Val
    610

<210> SEQ ID NO 141
<211> LENGTH: 1842
<212> TYPE: DNA
<213> ORGANISM: Homo sapiens

<400> SEQUENCE: 141
atggggccca ccctagcggt tcccaccccc tatggctgta ttggctgtaa gctaccccag    60
ccagaatacc caccggctct aatcatcttt atgttctgcg cgatggttat caccatcgtt   120
gtagacctaa tcggcaactc catggtcatt ttggctgtga cgaagaacaa gaagctccgg   180
aattctggca acatcttcgt ggtcagtctc tctgtggccg atatgctggt ggccatctac   240
ccataccctt tgatgctgca tgccatgtcc attggggct gggatctgag ccagttacag   300
tgccagatgg tcgggttcat cacagggctg agtgtggtcg gctccatctt caacatcgtg   360
gcaatcgcta tcaaccgtta ctgctacatc tgccacagcc tccagtacga acggatcttc   420
agtgtgcgca taccctgcat ctacctggtc atccctggga tcatgaccgt cctggctgtc   480
ctgcccaaca tgtacattgg caccatcgag tacgatcctc gcacctacac ctgcatcttc   540
aactatctga caaccctgt cttcactgtt accatcgtct gcatccactt cgtcctccct   600
ctcctcatcg tgggtttctg ctacgtgagg atctggacca aagtgctggc ggcccgtgac   660
cctgcagggc agaatcctga caaccaactt gctgaggttc gcaataaact aaccatgttt   720
gtgatcttcc tcctctttgc agtgtgctgg tgccctatca acgtgctcac tgtcttggtg   780
gctgtcagtc cgaaggagat ggcaggcaag atccccaact ggctttatct tgcagcctac   840
ttcatagcct acttcaacag ctgcctcaac gctgtgatct acgggctcct caatgagaat   900
ttccgaagag aatactggac catcttccat gctatgcggc accctatcat attcttctct   960
ggcctcatca gtgatattcg tgagatgcag gaggcccgta ccctggcccg cgcccgtgcc  1020
catgctcgcg accaagctcg tgaacaagac cgtgccatg cctgtcctgc tgtggaggaa  1080
accccgatga atgtccggaa tgttccatta cctggtgatg ctgcagctgg ccacccgac  1140 cgtgcctctg gccacccctaa gcccattcc agatcctcct ctgcctatcg caaatctgcc  1200
tctacccacc acaagtctgt ctttagccac tccaaggctg cctctggtca cctcaagcct  1260
gtctctggcc actccaagcc tgcctctggt caccccaagt ctgccactgt ctaccctaag  1320
cctgcctctg tccatttcaa ggctgactct gtccatttca agggtgactc tgtccatttc  1380
aagcctgact ctgttcattt caagcctgct ccagcaacc caagcccat cactggccac  1440 catgtctctg ctggcagcca ctccaagtct gccttcaatg ctgccaccag ccaccctaaa  1500
cccatcaagc cagctaccag ccatgctgag cccaccactg ctgactatcc caagcctgcc  1560
actaccagcc accctaagcc cgctgctgct gacaaccctg agctctctgc ctcccattgc  1620
cccgagatcc ctgccattgc ccaccctgtg tctgacgaca gtgacctccc tgagtcggcc  1680
tctagccctg ccgctgggcc caccaagcct gctgccagc agctggagtc tgacaccatc  1740
gctgaccttc ctgaccctac tgtagtcact accagtacca atgattacca tgatgtcgtg  1800
gttgttgatg ttgaagatga tcctgatgaa atggctgtgt ga                    1842
```

-continued

```
<210> SEQ ID NO 142
<211> LENGTH: 613
<212> TYPE: PRT
<213> ORGANISM: Homo sapiens

<400> SEQUENCE: 142
```

| | | | | | | | | | | | | | | |
|---|---|---|---|---|---|---|---|---|---|---|---|---|---|---|
| Met | Gly | Pro | Thr | Leu | Ala | Val | Pro | Thr | Pro | Tyr | Gly | Cys | Ile | Gly | Cys |
| 1 | | | | 5 | | | | | 10 | | | | | 15 |
| Lys | Leu | Pro | Gln | Pro | Glu | Tyr | Pro | Pro | Ala | Leu | Ile | Ile | Phe | Met | Phe |
| | | | 20 | | | | | 25 | | | | | 30 | |
| Cys | Ala | Met | Val | Ile | Thr | Ile | Val | Val | Asp | Leu | Ile | Gly | Asn | Ser | Met |
| | | 35 | | | | | 40 | | | | | 45 | | |
| Val | Ile | Leu | Ala | Val | Thr | Lys | Asn | Lys | Lys | Leu | Arg | Asn | Ser | Gly | Asn |
| | 50 | | | | | 55 | | | | | 60 | | | |
| Ile | Phe | Val | Val | Ser | Leu | Ser | Val | Ala | Asp | Met | Leu | Val | Ala | Ile | Tyr |
| 65 | | | | | 70 | | | | | 75 | | | | | 80 |
| Pro | Tyr | Pro | Leu | Met | Leu | His | Ala | Met | Ser | Ile | Gly | Gly | Trp | Asp | Leu |
| | | | | 85 | | | | | 90 | | | | | 95 | |
| Ser | Gln | Leu | Gln | Cys | Gln | Met | Val | Gly | Phe | Ile | Thr | Gly | Leu | Ser | Val |
| | | | 100 | | | | | 105 | | | | | 110 | |
| Val | Gly | Ser | Ile | Phe | Asn | Ile | Val | Ala | Ile | Ala | Ile | Asn | Arg | Tyr | Cys |
| | | | 115 | | | | | 120 | | | | | 125 | | |
| Tyr | Ile | Cys | His | Ser | Leu | Gln | Tyr | Glu | Arg | Ile | Phe | Ser | Val | Arg | Asn |
| | 130 | | | | | 135 | | | | | 140 | | | |
| Thr | Cys | Ile | Tyr | Leu | Val | Ile | Thr | Trp | Ile | Met | Thr | Val | Leu | Ala | Val |
| 145 | | | | | 150 | | | | | 155 | | | | | 160 |
| Leu | Pro | Asn | Met | Tyr | Ile | Gly | Thr | Ile | Glu | Tyr | Asp | Pro | Arg | Thr | Tyr |
| | | | | 165 | | | | | 170 | | | | | 175 | |
| Thr | Cys | Ile | Phe | Asn | Tyr | Leu | Asn | Asn | Pro | Val | Phe | Thr | Val | Thr | Ile |
| | | | 180 | | | | | 185 | | | | | 190 | | |
| Val | Cys | Ile | His | Phe | Val | Leu | Pro | Leu | Leu | Ile | Val | Gly | Phe | Cys | Tyr |
| | | | 195 | | | | | 200 | | | | | 205 | | |
| Val | Arg | Ile | Trp | Thr | Lys | Val | Leu | Ala | Ala | Arg | Asp | Pro | Ala | Gly | Gln |
| | 210 | | | | | 215 | | | | | 220 | | | |
| Asn | Pro | Asp | Asn | Gln | Leu | Ala | Glu | Val | Arg | Asn | Lys | Leu | Thr | Met | Phe |
| 225 | | | | | 230 | | | | | 235 | | | | | 240 |
| Val | Ile | Phe | Leu | Leu | Phe | Ala | Val | Cys | Trp | Cys | Pro | Ile | Asn | Val | Leu |
| | | | | 245 | | | | | 250 | | | | | 255 | |
| Thr | Val | Leu | Val | Ala | Val | Ser | Pro | Lys | Glu | Met | Ala | Gly | Lys | Ile | Pro |
| | | | 260 | | | | | 265 | | | | | 270 | | |
| Asn | Trp | Leu | Tyr | Leu | Ala | Ala | Tyr | Phe | Ile | Ala | Tyr | Phe | Asn | Ser | Cys |
| | | 275 | | | | | 280 | | | | | 285 | | | |
| Leu | Asn | Ala | Val | Ile | Tyr | Gly | Leu | Leu | Asn | Glu | Asn | Phe | Arg | Arg | Glu |
| | 290 | | | | | 295 | | | | | 300 | | | |
| Tyr | Trp | Thr | Ile | Phe | His | Ala | Met | Arg | His | Pro | Ile | Ile | Phe | Phe | Ser |
| 305 | | | | | 310 | | | | | 315 | | | | | 320 |
| Gly | Leu | Ile | Ser | Asp | Ile | Arg | Glu | Met | Gln | Glu | Ala | Arg | Thr | Leu | Ala |
| | | | 325 | | | | | 330 | | | | | 335 | | |
| Arg | Ala | Arg | Ala | His | Ala | Arg | Asp | Gln | Ala | Arg | Glu | Gln | Asp | Arg | Ala |
| | | | 340 | | | | | 345 | | | | | 350 | | |
| His | Ala | Cys | Pro | Ala | Val | Glu | Glu | Thr | Pro | Met | Asn | Val | Arg | Asn | Val |
| | | | 355 | | | | | 360 | | | | | 365 | | |
| Pro | Leu | Pro | Gly | Asp | Ala | Ala | Ala | Gly | His | Pro | Asp | Arg | Ala | Ser | Gly |
| | | 370 | | | | | 375 | | | | | 380 | | | |
| His | Pro | Lys | Pro | His | Ser | Arg | Ser | Ser | Ser | Ala | Tyr | Arg | Lys | Ser | Ala |

```
                385                 390                 395                 400
Ser Thr His His Lys Ser Val Phe Ser His Ser Lys Ala Ala Ser Gly
                    405                 410                 415
His Leu Lys Pro Val Ser Gly His Ser Lys Pro Ala Ser Gly His Pro
                    420                 425                 430
Lys Ser Ala Thr Val Tyr Pro Lys Pro Ala Ser Val His Phe Lys Ala
                    435                 440                 445
Asp Ser Val His Phe Lys Gly Asp Ser Val His Phe Lys Pro Asp Ser
                450                 455                 460
Val His Phe Lys Pro Ala Ser Ser Asn Pro Lys Pro Ile Thr Gly His
465                 470                 475                 480
His Val Ser Ala Gly Ser His Ser Lys Ser Ala Phe Asn Ala Ala Thr
                    485                 490                 495
Ser His Pro Lys Pro Ile Lys Pro Ala Thr Ser His Ala Glu Pro Thr
                    500                 505                 510
Thr Ala Asp Tyr Pro Lys Pro Ala Thr Thr Ser His Pro Lys Pro Ala
                    515                 520                 525
Ala Ala Asp Asn Pro Glu Leu Ser Ala Ser His Cys Pro Glu Ile Pro
                530                 535                 540
Ala Ile Ala His Pro Val Ser Asp Asp Ser Asp Leu Pro Glu Ser Ala
545                 550                 555                 560
Ser Ser Pro Ala Ala Gly Pro Thr Lys Pro Ala Ala Ser Gln Leu Glu
                    565                 570                 575
Ser Asp Thr Ile Ala Asp Leu Pro Asp Pro Thr Val Val Thr Thr Ser
                580                 585                 590
Thr Asn Asp Tyr His Asp Val Val Val Val Asp Val Glu Asp Asp Pro
                    595                 600                 605
Asp Glu Met Ala Val
        610
```

<210> SEQ ID NO 143
<211> LENGTH: 33
<212> TYPE: DNA
<213> ORGANISM: Artificial Sequence
<220> FEATURE:
<223> OTHER INFORMATION: Novel Sequence

<400> SEQUENCE: 143
gctgaggttc gcaataaact aaccatgttt gtg        33

<210> SEQ ID NO 144
<211> LENGTH: 31
<212> TYPE: DNA
<213> ORGANISM: Artificial Sequence
<220> FEATURE:
<223> OTHER INFORMATION: Novel Sequence

<400> SEQUENCE: 144
ctccttcggt cctcctatcg ttgtcagaag t        31

<210> SEQ ID NO 145
<211> LENGTH: 27
<212> TYPE: DNA
<213> ORGANISM: Artificial Sequence
<220> FEATURE:
<223> OTHER INFORMATION: Novel Sequence

<400> SEQUENCE: 145
ttagatatcg gggcccaccc tagcggt        27

```
<210> SEQ ID NO 146
<211> LENGTH: 29
<212> TYPE: DNA
<213> ORGANISM: Artificial Sequence
<220> FEATURE:
<223> OTHER INFORMATION: Novel Sequence

<400> SEQUENCE: 146
ggtaccccca cagccatttc atcaggatc                                      29

<210> SEQ ID NO 147
<211> LENGTH: 31
<212> TYPE: DNA
<213> ORGANISM: Artificial Sequence
<220> FEATURE:
<223> OTHER INFORMATION: Novel Sequence

<400> SEQUENCE: 147
gatctggagt accccattga cgtcaatggg g                                   31

<210> SEQ ID NO 148
<211> LENGTH: 31
<212> TYPE: DNA
<213> ORGANISM: Artificial Sequence
<220> FEATURE:
<223> OTHER INFORMATION: Novel Sequence

<400> SEQUENCE: 148 gatccccat tgacgtcaat ggggtactcc a                                    31
```